US012090294B2

(12) United States Patent
Jung et al.

(10) Patent No.: US 12,090,294 B2
(45) Date of Patent: Sep. 17, 2024

(54) TARGETED DRUG DELIVERY METHODS USING A MICRONEEDLE

(71) Applicant: Georgia Tech Research Corporation, Atlanta, GA (US)

(72) Inventors: Jae Hwan Jung, Atlanta, GA (US); Mark R. Prausnitz, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 872 days.

(21) Appl. No.: 16/609,583

(22) PCT Filed: May 2, 2018

(86) PCT No.: PCT/US2018/030688
§ 371 (c)(1),
(2) Date: Oct. 30, 2019

(87) PCT Pub. No.: WO2018/204515
PCT Pub. Date: Nov. 8, 2018

(65) Prior Publication Data
US 2020/0061357 A1    Feb. 27, 2020

Related U.S. Application Data

(60) Provisional application No. 62/500,209, filed on May 2, 2017.

(51) Int. Cl.
*A61P 27/02*    (2006.01)
*A61K 9/00*    (2006.01)
(Continued)

(52) U.S. Cl.
CPC ....... *A61M 37/0015* (2013.01); *A61K 9/0009* (2013.01); *A61K 9/0019* (2013.01);
(Continued)

(58) Field of Classification Search
CPC ................................. A61M 37/0015
See application file for complete search history.

(56) References Cited

U.S. PATENT DOCUMENTS

| 2,187,259 A | 1/1940 | Barnhart |
| 2,841,145 A | 7/1958 | Epps |
| (Continued) | | |

FOREIGN PATENT DOCUMENTS

| CA | 2639322 | 3/2009 |
| CN | 1229679 A | 9/1999 |
| (Continued) | | |

OTHER PUBLICATIONS

Samirkumar R Patel. "Suprachoroidal Drug Delivery to the Eye Using Hollow Microneedles." Georgia Institute of Technology, Thesis, May 2011, pp. i-xxvii and 1-147. (Year: 2011).*
(Continued)

*Primary Examiner* — Isaac Shomer
(74) *Attorney, Agent, or Firm* — COOLEY LLP

(57) ABSTRACT

The present disclosure provides methods for administering formulations to the suprachoroidal space of the eye to achieve targeted drug delivery to a desired site of action within the eye. The methods include using a pushing formulation that includes a material such as a gel that expands due to physiochemical cues; or using an electric field to affect the movement of a formulation within the suprachoroidal space; or a combination of a pushing formulation with an electric field.

16 Claims, 36 Drawing Sheets

(51) Int. Cl.
   *A61K 9/16* (2006.01)
   *A61K 31/728* (2006.01)
   *A61M 37/00* (2006.01)

(52) U.S. Cl.
   CPC .......... *A61K 9/0048* (2013.01); *A61K 9/1652* (2013.01); *A61K 31/728* (2013.01); *A61P 27/02* (2018.01); *A61M 2037/0023* (2013.01); *A61M 2037/0061* (2013.01)

(56) References Cited

U.S. PATENT DOCUMENTS

| | | | |
|---|---|---|---|
| 2,939,459 A | 6/1960 | Lazarte et al. | |
| 3,376,999 A | 4/1968 | De Hart et al. | |
| 3,477,432 A | 11/1969 | Shaw | |
| 3,739,947 A | 6/1973 | Baumann et al. | |
| 3,762,540 A | 10/1973 | Baumann et al. | |
| 3,788,320 A | 1/1974 | Dye | |
| 3,838,690 A | 10/1974 | Friedman | |
| 3,892,311 A | 7/1975 | Sneider | |
| 3,962,430 A | 6/1976 | O'Neill | |
| 3,964,482 A | 6/1976 | Gerstel et al. | |
| 4,226,328 A | 10/1980 | Beddow | |
| 4,377,897 A | 3/1983 | Eichenbaum et al. | |
| 4,383,530 A | 5/1983 | Bruno | |
| 4,417,887 A | 11/1983 | Koshi | |
| 4,432,964 A | 2/1984 | Shell et al. | |
| 4,501,363 A | 2/1985 | Isbey, Jr. | |
| 4,525,346 A | 6/1985 | Stark | |
| 4,564,016 A | 1/1986 | Maurice et al. | |
| 4,601,708 A | 7/1986 | Jordan | |
| 4,615,331 A | 10/1986 | Kramann | |
| 4,689,040 A | 8/1987 | Thompson | |
| 4,708,147 A | 11/1987 | Haaga | |
| 4,717,383 A | 1/1988 | Phillips et al. | |
| 4,736,850 A | 4/1988 | Bowman et al. | |
| 4,755,169 A | 7/1988 | Sarnoff et al. | |
| 4,795,432 A | 1/1989 | Karczmer | |
| 4,804,371 A | 2/1989 | Vaillancourt | |
| 4,826,490 A | 5/1989 | Byrne et al. | |
| 4,826,871 A | 5/1989 | Gressel et al. | |
| 4,889,529 A | 12/1989 | Haindl | |
| 4,941,874 A | 7/1990 | Sandow et al. | |
| 4,966,773 A | 10/1990 | Gressel et al. | |
| 5,015,240 A | 5/1991 | Soproni et al. | |
| 5,024,662 A | 6/1991 | Menes et al. | |
| 5,066,276 A | 11/1991 | Wang | |
| 5,098,389 A | 3/1992 | Cappucci | |
| 5,137,447 A | 8/1992 | Hunter | |
| 5,164,188 A | 11/1992 | Wong | |
| 5,172,807 A | 12/1992 | Dragan et al. | |
| 5,181,909 A | 1/1993 | McFarlane | |
| 5,206,267 A | 4/1993 | Shulman | |
| 5,273,530 A | 12/1993 | del Cerro et al. | |
| 5,279,564 A | 1/1994 | Taylor | |
| 5,295,972 A | 3/1994 | Mischenko | |
| 5,300,084 A | 4/1994 | Johnson | |
| 5,312,361 A | 5/1994 | Zadini et al. | |
| 5,320,609 A | 6/1994 | Haber et al. | |
| 5,354,286 A | 10/1994 | Mesa et al. | |
| 5,358,489 A | 10/1994 | Wyrick | |
| 5,364,373 A | 11/1994 | Waskonig et al. | |
| 5,364,374 A | 11/1994 | Morrison et al. | |
| 5,364,734 A | 11/1994 | Morrison et al. | |
| 5,397,313 A | 3/1995 | Gross | |
| 5,399,159 A | 3/1995 | Chin et al. | |
| 5,407,070 A | 4/1995 | Bascos et al. | |
| 5,409,457 A | 4/1995 | del Cerro et al. | |
| 5,443,505 A | 8/1995 | Wong et al. | |
| 5,538,503 A | 7/1996 | Henley et al. | |
| 5,547,467 A | 8/1996 | Pliquett et al. | |
| 5,575,780 A | 11/1996 | Saito | |
| 5,632,740 A | 5/1997 | Koch et al. | |
| 5,658,256 A | 8/1997 | Shields | |
| D383,049 S | 9/1997 | Concari et al. | |
| 5,667,491 A | 9/1997 | Pliquett et al. | |
| 5,681,825 A | 10/1997 | Lindqvist et al. | |
| 5,766,198 A | 6/1998 | Li | |
| 5,766,242 A | 6/1998 | Wong et al. | |
| 5,767,079 A | 6/1998 | Glaser et al. | |
| 5,779,668 A | 7/1998 | Grabenkort | |
| 5,788,679 A | 8/1998 | Gravlee, Jr. | |
| 5,792,099 A | 8/1998 | DeCamp et al. | |
| 5,817,075 A | 10/1998 | Giungo | |
| 5,824,072 A | 10/1998 | Wong | |
| 5,911,223 A | 6/1999 | Weaver et al. | |
| 5,952,378 A | 9/1999 | Stjernschantz et al. | |
| 5,968,022 A | 10/1999 | Saito | |
| 6,059,111 A | 5/2000 | Davilla et al. | |
| 6,083,199 A | 7/2000 | Thorley et al. | |
| 6,143,329 A | 11/2000 | Kim | |
| 6,159,218 A | 12/2000 | Aramant et al. | |
| 6,280,470 B1 | 8/2001 | Peyman | |
| 6,299,603 B1 | 10/2001 | Hecker et al. | |
| 6,309,347 B1 | 10/2001 | Takahashi et al. | |
| 6,309,374 B1 | 10/2001 | Hecker et al. | |
| 6,319,225 B1 | 11/2001 | Sugita et al. | |
| 6,319,240 B1* | 11/2001 | Beck | A61N 1/044 604/521 |
| 6,334,856 B1 | 1/2002 | Allen et al. | |
| 6,378,526 B1 | 4/2002 | Bowman et al. | |
| 6,387,078 B1 | 5/2002 | Gillespie, III | |
| 6,397,849 B1 | 6/2002 | Bowman et al. | |
| 6,432,090 B1 | 8/2002 | Brunel | |
| 6,494,865 B1 | 12/2002 | Alchas | |
| 6,503,231 B1 | 1/2003 | Prausnitz et al. | |
| 6,524,581 B1 | 2/2003 | Adamis | |
| 6,530,904 B1 | 3/2003 | Edwards et al. | |
| 6,540,725 B1 | 4/2003 | Ponzi | |
| 6,551,299 B2 | 4/2003 | Miyoshi et al. | |
| 6,569,123 B2 | 5/2003 | Alchas et al. | |
| 6,611,707 B1 | 8/2003 | Prausnitz et al. | |
| 6,622,864 B1 | 9/2003 | Debbs et al. | |
| 6,743,211 B1 | 6/2004 | Prausnitz et al. | |
| 6,773,916 B1 | 8/2004 | Thiel et al. | |
| D499,153 S | 11/2004 | Kuo | |
| 6,883,222 B2 | 4/2005 | Landau | |
| 6,918,889 B1 | 7/2005 | Brunel | |
| 6,929,623 B2 | 8/2005 | Stone | |
| 6,936,053 B1 | 8/2005 | Weiss | |
| 6,979,316 B1 | 12/2005 | Rubin et al. | |
| 7,025,774 B2 | 4/2006 | Freeman et al. | |
| 7,150,735 B2 | 12/2006 | Hickle | |
| 7,207,965 B2 | 4/2007 | Simon | |
| 7,207,980 B2 | 4/2007 | Christian et al. | |
| 7,211,062 B2 | 5/2007 | Kwon | |
| 7,214,212 B2 | 5/2007 | Pommereau et al. | |
| 7,226,439 B2 | 6/2007 | Prausnitz et al. | |
| 7,316,676 B2 | 1/2008 | Peyman et al. | |
| 7,425,207 B2 | 9/2008 | Miller et al. | |
| 7,435,237 B2 | 10/2008 | Tan | |
| 7,468,057 B2 | 12/2008 | Ponzi | |
| D590,690 S | 4/2009 | Bertini | |
| D598,543 S | 8/2009 | Vogel et al. | |
| 7,569,035 B1 | 8/2009 | Wilmot et al. | |
| 7,615,041 B2 | 11/2009 | Sullivan et al. | |
| 7,648,482 B2 | 1/2010 | Edwards et al. | |
| 7,678,077 B2 | 3/2010 | Harris et al. | |
| 7,678,078 B1 | 3/2010 | Peyman et al. | |
| 7,722,581 B2 | 5/2010 | Peyman | |
| 7,914,803 B2 | 3/2011 | Chowhan et al. | |
| 7,918,814 B2 | 4/2011 | Prausnitz et al. | |
| 7,918,874 B2 | 4/2011 | Siegal | |
| 7,947,660 B2 | 5/2011 | Clark et al. | |
| 7,967,772 B2 | 6/2011 | McKenzie et al. | |
| 8,003,124 B2 | 8/2011 | Varner et al. | |
| 8,114,110 B2 | 2/2012 | Bednarek et al. | |
| 8,137,312 B2 | 3/2012 | Sundar et al. | |
| 8,172,830 B2 | 5/2012 | Christian et al. | |
| 8,173,617 B2 | 5/2012 | Clark et al. | |
| 8,192,408 B2 | 6/2012 | Nazzaro et al. | |
| 8,197,435 B2 | 6/2012 | Prausnitz et al. | |
| 8,197,443 B2 | 6/2012 | Sundar et al. | |
| 8,221,353 B2 | 7/2012 | Cormier et al. | |

(56) References Cited

U.S. PATENT DOCUMENTS

| | | |
|---|---|---|
| 8,235,967 B2 | 8/2012 | Chevallier et al. |
| D667,111 S | 9/2012 | Robinson |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,430,862 B2 | 4/2013 | Peyman et al. |
| 8,448,786 B2 | 5/2013 | Tomes et al. |
| 8,460,242 B2 | 6/2013 | Paques et al. |
| 8,506,515 B2 | 8/2013 | Burns et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,617,121 B2 | 12/2013 | Lanin et al. |
| 8,632,589 B2 | 1/2014 | Helmy |
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,770,361 B2 | 9/2017 | Andino et al. |
| 9,788,995 B2 | 10/2017 | Prausnitz et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 10,188,550 B2 | 1/2019 | Andino et al. |
| 10,390,901 B2 | 8/2019 | Godfrey et al. |
| 10,517,756 B2 | 12/2019 | Andino et al. |
| 2001/0008961 A1 | 7/2001 | Hecker et al. |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0142459 A1 | 10/2002 | Williams et al. |
| 2002/0156413 A1 | 10/2002 | Williams et al. |
| 2003/0009113 A1 | 1/2003 | Olson |
| 2003/0018295 A1* | 1/2003 | Henley .......... A61N 1/0428 604/20 |
| 2003/0050602 A1 | 3/2003 | Pettis et al. |
| 2003/0083645 A1 | 5/2003 | Angel et al. |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0049150 A1 | 3/2004 | Dalton et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0186084 A1 | 9/2004 | Alam et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0089545 A1 | 4/2005 | Kuwano et al. |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0084942 A1 | 4/2006 | Kim et al. |
| 2006/0086689 A1 | 4/2006 | Raju |
| 2006/0089607 A1 | 4/2006 | Chen |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093877 A1 | 4/2007 | Beecham et al. |
| 2007/0151882 A1 | 7/2007 | Cocheteux et al. |
| 2007/0178197 A1 | 8/2007 | Larue et al. |
| 2007/0191863 A1 | 8/2007 | De Juan et al. |
| 2007/0202116 A1 | 8/2007 | Burnie et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford, III et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0282405 A1 | 12/2007 | Wong et al. |
| 2007/0287985 A1 | 12/2007 | Estes et al. |
| 2007/0299386 A1 | 12/2007 | Peyman |
| 2008/0008762 A1 | 1/2008 | Robinson et al. |
| 2008/0009471 A1 | 1/2008 | Higuchi et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0071246 A1 | 3/2008 | Nazzaro et al. |
| 2008/0097335 A1 | 4/2008 | Trogden et al. |
| 2008/0097346 A1 | 4/2008 | Charles |
| 2008/0097390 A1 | 4/2008 | Dacquay et al. |
| 2008/0131484 A1 | 6/2008 | Robinson et al. |

(56) References Cited

U.S. PATENT DOCUMENTS

| | | |
|---|---|---|
| 2008/0152694 A1 | 6/2008 | Lobl et al. |
| 2008/0177239 A1 | 7/2008 | Li et al. |
| 2008/0228127 A1 | 9/2008 | Burns et al. |
| 2008/0234625 A1 | 9/2008 | Dacquay et al. |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0088721 A1 | 4/2009 | Bizemont et al. |
| 2009/0105749 A1 | 4/2009 | De Juan et al. |
| 2009/0148527 A1 | 6/2009 | Robinson |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van emelen et al. |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0057011 A1 | 3/2010 | Charles |
| 2010/0074957 A1 | 3/2010 | Robinson et al. |
| 2010/0098772 A1 | 4/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0173866 A1 | 7/2010 | Hee et al. |
| 2010/0191176 A1 | 7/2010 | Ho et al. |
| 2010/0211079 A1 | 8/2010 | Aramant |
| 2010/0241102 A1 | 9/2010 | Ma |
| 2010/0256597 A1* | 10/2010 | Prausnitz .............. A61F 9/0008 604/257 |
| 2010/0312120 A1 | 12/2010 | Meier |
| 2011/0004265 A1 | 1/2011 | Wenger et al. |
| 2011/0060310 A1 | 3/2011 | Prestrelski et al. |
| 2011/0112546 A1 | 5/2011 | Juan, Jr. et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0282298 A1 | 11/2011 | Agian et al. |
| 2011/0295152 A1 | 12/2011 | Sasaki et al. |
| 2011/0306923 A1 | 12/2011 | Roy |
| 2012/0004245 A1 | 1/2012 | May et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0078224 A1 | 3/2012 | Lerner et al. |
| 2012/0082730 A1* | 4/2012 | Banerjee ................ A61K 47/36 977/773 |
| 2012/0083727 A1 | 4/2012 | Barnett |
| 2012/0095414 A1 | 4/2012 | Lanin et al. |
| 2012/0095438 A1 | 4/2012 | Anin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'dea et al. |
| 2012/0136318 A1 | 5/2012 | Anin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0197218 A1 | 8/2012 | Timm |
| 2012/0220917 A1 | 8/2012 | Silvestrini et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2013/0035662 A1 | 2/2013 | Decker et al. |
| 2013/0040895 A1 | 2/2013 | Robinson et al. |
| 2013/0041265 A1 | 2/2013 | Sostek et al. |
| 2013/0060202 A1 | 3/2013 | Thorley et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0088552 A1 | 3/2014 | Soni et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0135716 A1 | 5/2014 | Clarke et al. |
| 2014/0194834 A1 | 7/2014 | Passaglia et al. |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0275923 A1* | 9/2014 | Haffner .............. A61B 5/14532 600/377 |
| 2014/0276482 A1 | 9/2014 | Astafieva et al. |
| 2014/0296802 A1 | 10/2014 | Geiger et al. |
| 2014/0309599 A1 | 10/2014 | Schaller |
| 2014/0323979 A1 | 10/2014 | Henley et al. |
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0110717 A1 | 4/2015 | Distel et al. |
| 2015/0129456 A1 | 5/2015 | Miller et al. |
| 2015/0133415 A1 | 5/2015 | Whitcup |
| 2015/0209180 A1 | 7/2015 | Prausnitz et al. |
| 2015/0258120 A1 | 9/2015 | Zarnitsyn et al. |
| 2015/0320596 A1 | 11/2015 | Gifford, III et al. |
| 2016/0015895 A1 | 1/2016 | Blondino et al. |
| 2016/0022486 A1 | 1/2016 | Clauson et al. |
| 2016/0106584 A1 | 4/2016 | Andino et al. |
| 2016/0193080 A1 | 7/2016 | Hammack et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2016/0331738 A1 | 11/2016 | Jarrett et al. |
| 2017/0095369 A1 | 4/2017 | Andino et al. |
| 2017/0224435 A1 | 8/2017 | Godfrey et al. |
| 2017/0224534 A1 | 8/2017 | Andino et al. |
| 2017/0290702 A1 | 10/2017 | Yamamoto et al. |
| 2017/0333416 A1 | 11/2017 | Zarnitsyn et al. |

(56) References Cited

U.S. PATENT DOCUMENTS

| | | |
|---|---|---|
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0042767 A1 | 2/2018 | Andino et al. |
| 2018/0092897 A1 | 4/2018 | Zarnitsyn et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |
| 2019/0231592 A1 | 8/2019 | Andino et al. |
| 2019/0240208 A1 | 8/2019 | Zarnitsyn et al. |
| 2019/0269702 A1 | 9/2019 | White et al. |
| 2019/0290485 A1 | 9/2019 | Andino et al. |
| 2019/0307606 A1 | 10/2019 | Andino et al. |
| 2019/0350755 A1 | 11/2019 | Andino et al. |

FOREIGN PATENT DOCUMENTS

| | | |
|---|---|---|
| CN | 1604799 A | 4/2005 |
| CN | 1706365 | 12/2005 |
| CN | 1736474 | 2/2006 |
| CN | 101052434 A | 10/2007 |
| CN | 101351239 A | 1/2009 |
| CN | 201356711 Y | 12/2009 |
| CN | 101854891 A | 10/2010 |
| CN | 101959519 A | 1/2011 |
| CN | 103037802 A | 4/2013 |
| CN | 103209733 A | 7/2013 |
| CN | 103857431 A | 6/2014 |
| EA | 006961 | 6/2006 |
| EP | 1188456 | 3/2002 |
| EP | 1568359 | 8/2005 |
| EP | 2193821 | 6/2010 |
| EP | 2307055 | 4/2011 |
| JP | 2001-525826 | 12/2001 |
| JP | 2007-510744 | 4/2007 |
| JP | 2007-518804 | 7/2007 |
| JP | 2009-183441 | 8/2009 |
| JP | 2009-531298 | 9/2009 |
| JP | 2010-234034 | 10/2010 |
| JP | 2013-543418 | 12/2013 |
| RU | 14351 U1 | 7/2000 |
| RU | 2344767 | 1/2009 |
| RU | 2353393 | 4/2009 |
| RU | 2428956 | 9/2011 |
| WO | WO 92/08406 | 5/1992 |
| WO | WO 92/20389 | 11/1992 |
| WO | WO 94/01124 | 1/1994 |
| WO | WO 94/12217 | 6/1994 |
| WO | WO 96/09838 | 4/1996 |
| WO | WO 98/51348 | 11/1998 |
| WO | WO 2000/007530 | 2/2000 |
| WO | WO 2000/007565 | 2/2000 |
| WO | WO 2001/041685 | 6/2001 |
| WO | WO 2002/058769 | 8/2002 |
| WO | WO 2003/002094 | 1/2003 |
| WO | WO 2003/024507 | 3/2003 |
| WO | WO 2003/039633 | 5/2003 |
| WO | WO 2005/011741 | 2/2005 |
| WO | WO 2005/032510 | 4/2005 |
| WO | WO 2005/046641 | 5/2005 |
| WO | WO 2005/069831 | 8/2005 |
| WO | WO 2005/072701 | 8/2005 |
| WO | WO 2005/074942 | 8/2005 |
| WO | WO 2005/107845 | 11/2005 |
| WO | WO 2006/004595 | 1/2006 |
| WO | WO 2006/042252 | 4/2006 |
| WO | WO 2006/058189 | 6/2006 |
| WO | WO 2006/128034 | 11/2006 |
| WO | WO 2006/138719 | 12/2006 |
| WO | WO 2007/100745 | 9/2007 |
| WO | WO 2007/130105 | 11/2007 |
| WO | WO 2007/131050 | 11/2007 |
| WO | WO 2007/150018 | 12/2007 |
| WO | WO 2008/082637 | 7/2008 |
| WO | WO 2009/067325 | 5/2009 |
| WO | WO 2009/105534 | 8/2009 |
| WO | WO 2009/114521 | 9/2009 |
| WO | WO 2010/009034 | 1/2010 |
| WO | WO 2010/054660 | 5/2010 |
| WO | WO 2010/132751 | 11/2010 |
| WO | WO 2011/057065 | 5/2011 |
| WO | WO 2011/123722 | 10/2011 |
| WO | WO 2011/139713 | 11/2011 |
| WO | WO 2012/019136 | 2/2012 |
| WO | WO 2012/051575 | 4/2012 |
| WO | WO 2012/118498 | 9/2012 |
| WO | WO 2012/125869 | 9/2012 |
| WO | WO 2012/125872 | 9/2012 |
| WO | WO 2012/162459 | 11/2012 |
| WO | WO 2013/050236 | 4/2013 |
| WO | WO 2013/098166 | 7/2013 |
| WO | WO 2013/151904 | 10/2013 |
| WO | WO 2014/028285 | 2/2014 |
| WO | WO 2014/036009 | 3/2014 |
| WO | WO 2014/074823 | 5/2014 |
| WO | WO 2014/179698 | 11/2014 |
| WO | WO 2014/197317 | 12/2014 |
| WO | WO 2015/015467 | 2/2015 |
| WO | WO 2015/095772 | 6/2015 |
| WO | WO 2015/195842 | 12/2015 |
| WO | WO 2015/196085 | 12/2015 |
| WO | WO 2016/042162 | 3/2016 |
| WO | WO 2016/042163 | 3/2016 |
| WO | WO 2017/120600 | 7/2017 |
| WO | WO 2017/120601 | 7/2017 |
| WO | WO 2017/139375 | 8/2017 |
| WO | WO 2017/190142 | 11/2017 |
| WO | WO 2017/192565 | 11/2017 |

OTHER PUBLICATIONS

Bryce Chiang. "Distribution, Clearance, and Controlled Release of Molecules and Particles After Microneedle Injection into the Suprachoroidal Space." Georgia Institute of Technology, Thesis, Aug. 2016, pp. i-xix and 1-208. (Year: 2016).*

Mayo Clinic. "Sodium Chloride (Ophthalmic Route)" https://www.mayoclinic.org/drugs-supplements/sodium-chloride-ophthalmic-route/description/drg-20068860?p=1 accessed Nov. 14, 2022, pp. 1-5. (Year: 2022).*

Tatjana C. Jakobs. "Glaucoma Methods and Protocols." ISBN 978-1-4939-7407-8, 2018, pp. i-xii and 1-337. (Year: 2018).*

Bryce Chiang, Jae Hwan Jung, and Mark R. Prausnitz. "The suprachoroidal space as a route of administration to the posterior segment of the eye." Advanced Drug Delivery Reviews, vol. 126, 2018, pp. 58-66. (Year: 2018).*

Yoo Chun Kim, Kyung Hee Oh, Henry F. Edelhauser, Mark R. Prausnitz. "Formulation to target delivery to the ciliary body and choroid via the suprachoroidal space of the eye using microneedles." European Journal of Pharmaceutics and Biopharmaceutics, vol. 95 (2015) 398-406. (Year: 2015).*

Suzanne Einmahl, Michelle Savoldelli, Francois D''Hermies, Cyrus Tabatabay, Robert Gurny, and Francine Behar-Cohen. "Evaluation of a Novel Biomaterial in the Suprachoroidal Space of the Rabbit Eye." Investigative Ophthalmology & Visual Science, May 2002, vol. 43, No. 5, pp. 1533-1539. (Year: 2002).*

Examination Report No. 1 for Australian Application No. 2014259694, dated May 24, 2018, 2 pages.

First Office Action for Chinese Application No. 201480025034.4, dated Apr. 24, 2018, 10 pages.

Office Action for Eurasian Application No. 201592109, mailed Apr. 1, 2016, 4 pages.

Office Action for Eurasian Application No. 201592109, mailed Jan. 31, 2018, 2 pages.

Extended Search Report for European Application No. 14791646.4, dated Nov. 21, 2016, 6 pages.

Office Action for European Application No. 14791646.4, dated Dec. 4, 2017, 5 pages.

Office Action for European Application No. 14791646.4, dated Sep. 17, 2018, 5 pages.

(56) References Cited

OTHER PUBLICATIONS

Office Action for Israeli Application No. 242395, dated May 7, 2019, 7 pages.
Office Action for Mexican Application No. MX/a/2015/015282, dated May 15, 2019, 8 pages.
Notice of Reasons for Rejection for Japanese Application No. 2016-512068, mailed Mar. 26, 2018, 4 pages.
Office Action for New Zealand Application No. 714172, dated Feb. 1, 2018, 4 pages.
Office Action for New Zealand Application No. 714172, dated Jul. 24, 2018, 4 pages.
Office Action for New Zealand Application No. 714172, dated Dec. 12, 2018, 3 pages.
Search Report and Written Opinion for Singapore Application No. 11201509051V, dated Nov. 2, 2016, 6 pages.
Examination Report for Singapore Application No. 11201509051V, dated Feb. 1, 2017, 4 pages.
International Search Report and Written Opinion for International Application No. PCT/US2014/036590, mailed Dec. 10, 2014, 10 pages.
Office Action for U.S. Appl. No. 14/268,687, mailed May 19, 2016, 6 pages.
Partial European Search Report for European Application No. 18176172.7, mailed Oct. 30, 2018, 13 pages.
Extended European Search Report for European Application No. 18176172.7, mailed Feb. 6, 2019, 11 pages.
Notice of Reasons for Rejection for Japanese Application No. 2018-142345, mailed Jun. 6, 2019, 6 pages.
Office Action for U.S. Appl. No. 14/523,243, mailed Feb. 27, 2015, 14 pages.
Office Action for U.S. Appl. No. 15/946,838, mailed Jun. 27, 2019, 7 pages.
Office Action for U.S. Appl. No. 16/381,213, mailed May 31, 2019, 7 pages.
Partial Supplementary European Search Report for European Application No. 15810459.6, mailed Dec. 22, 2017, 13 pages.
Extended European Search Report for European Application No. 15810459.6, mailed Apr. 16, 2018, 11 pages.
Notice of Reasons for Rejection for Japanese Application No. 2016-574090, mailed Mar. 4, 2019, 18 pages.
Office Action for Russian Application No. 2017101660, dated Mar. 5, 2019, 7 pages.
Office Action for U.S. Appl. No. 15/383,582, mailed May 5, 2017, 10 pages.
International Search Report and Written Opinion for International Application No. PCT/US2015/036715, mailed Jan. 19, 2016, 9 pages.
International Search Report and Written Opinion for International Application No. PCT/US2017/030609, mailed Oct. 6, 2017, 12 pages.
International Search Report and Written Opinion for International Application No. PCT/US2017/065796, mailed Apr. 12, 2018, mailed Apr. 12, 2018, 9 pages.
International Search Report and Written Opinion for International Application No. PCT/US2017/046553, mailed Dec. 13, 2017, 14 pages.
Abbott Laboratories Inc., Abbott Park, Illinois, USA, Abbott Medical Optics, "HEALON5 OVD," 2004, [online]. Retrieved from the Interent: <URL: http://abbottmedicaloptics.com/products/cataract/ovds/healon5-viscoelastic>. Retrieved from the Internet on: Aug. 16, 2016, 5 pages.
Anthem, USA, "Medical Policy. Suprachoroidal Injection of a Pharmacologic Agent," Last Review Date: Nov. 14, 2013, [online]. Retrieved from the Internet: <URL: http://www.anthem.com/medicalpolicies/policies/mp_pw_b076412.htm>. Retrieved from the Internet on: Oct. 24, 2014, American Medical Association, 3 pages.
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Careforde Inc., Careforde Healthcare, Chicago, IL, "B Braun Glass Loss-of-Resistance Syringes # 332155—5cc Glass Loss-of-Resistance Syringe, Luer Lock Metal Tip, 10/cs," [online]. Retrieved from the Internet: <http://careforde.com/b-braun-glass-loss-of-resistance-syringes-332155-5cc-glass-loss-of-resistance-syringe-luer-lock-metal-tip-10-cs/>. Retrieved from the Internet on: Oct. 16, 2014, (2014), 2 pages.
Careforde Healthcare, B Braun Glass Loss-of-Resistance Syringes # 332158—10cc Glass Loss-of-Resistance Syringe, Luer Slip Metal Tip, 10/cs, (2014), 2 pages.
Careforde Inc., Careforde Healthcare, Chicago, IL, "B Braun Perifix Plastic Loss-of-Resistance Syringes # 332152—8cc Plastic Luer Lock Loss-of-Resistance Syringe, 50/cs," [online]. Retrieved from the Internet: <http://careforde.com/b-braun-perifix-plastic-loss-of-resistance-syringes-332152-8cc-plastic-luer-lock-loss-of-resistance-syringe-50-cs/>. Retrieved from the Internet on: Oct. 16, 2014, (2014), 2 pages.
Cho, S. W. et al., "Drug delivery to the suprachoroidal space," Chap. 12 in: Ocular Drug Delivery Systems: Barriers and Application of Nanoparticulate Systems, Thassu, D et al. (eds.), CRC Press, pp. 235-258 (2012).
Doncaster and Bassetlaw Hospitals, NHS Foundation Trust, Department of Ophthalmology, "Intravitreal injection of triamcinolone," Jul. 2010, [online]. Retrieved from the Internet: <URL: http://www.dbh.nhs.uk/Library/Patient_Information_Leaflets/WPR32110%20IIT%20No%20crops.pdf>, 2 pages.
Edwards, A. et al., "Fiber matrix model of sclera and corneal stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, <URL: http:/en.wikipedia.org/wiki/Epidural>, 21 pages.
Falkenstein, I. A et al., "Comparison of visual acuity in macular degeneration patients measured with Snellen and Early Treatment Diabetic Retinopathy study charts," Ophthalmology 115(2):319-323 (Feb. 2008).
Feldkamp, L. A. et al., "Practical cone-beam algorithm," J. Opt. Soc. Am. A, 1(6):612-619 (1984).
Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Heller, J., Ocular delivery using poly(ortho esters), Adv. Drug. Deliv. Rev., 57(14):2053-2062 (2005).
Haller, J. A., "Intraocular Steroids in the Office. New formulations offer preservative-free triamcinolone without relying on compounding pharmacies," Retinal Physician [online]. Retrieved from the Internet: <URL: https://www.retinalphysician.com/supplements/2009/february2009/special-edition/intraocular-steroids-in-the-office>, Feb. 1, 2009, 4 pages.
Haller, J. A. et al., "Evaluation of the safety and performance of an applicator for a novel intravitreal dexamethasone drug delivery system for the treatment of macular edema," Retina, 29(1):46-51 (2009).

(56) References Cited

OTHER PUBLICATIONS

Hogan et al., Chapter Eight, Choroid, in Histology of the Human Eye, 9 pages (1971).
Jain, A., "Pseudo loss of resistance in epidural space localization: A complication of subcutaneous emphysema or simply a faulty technique," Saudi J. Anaseth, 5(1):108-109 (2011) (Abstract).
Jiang, J. et al., "Measurement and Prediction of Lateral Diffusion within Human Sclera," Investigative Ophthalmology & Visual Science, 47(7):3011-3016 (2006).
Jiang, J. et al., "Coated Microneedles for Drug Delivery to the Eye," Investigative Ophthalmology & Visual Science, 48(9):4038-4043 (2007).
Jiang, J. et al., "Intrascleral drug delivery to the eye using hollow microneedles," Pharmaceutical Research, 26(2):395-403 (2009).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).
Karim, R. et al., "Interventions for the treatment of uveitic macular edema: a systematic review and meta-analysis," Clinical Ophthalmology, 7:1109-1144 (2013).
Lee, S-B et al., "Drug delivery through the sclera: effects of thickness, hydration and sustained release systems," Experimental Eye Research, 78:599-607 (2004).
Lee et al., "Thixotropic property in pharmaceutical formulations," Journal of Controlled Release (2009) 136:88-98.
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: <URL: http://bmctoday.net/crstodayeurope/2013/10/article.asp?f=suprachoroidal-devices-in-glaucoma>. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
McAllister, D. V. et al., "Microfabricated needles for transdermal delivery of macromolecules and nanoparticles: Fabrication methods and transport studies," Proc. Nat'l Acad. Sci USA, 100(24):13755-13760 (2003).
Norman, D., Epidural analgesia using loss of resistance with air versus saline: Does it make a difference? Should we reevaluate our practice?, AANA Journal, 71(6):449-453 (Dec. 2003).
Olsen, T. W. et al., "Cannulation of the Suprachoroidal Space: A Novel Drug Delivery Methodology to the Posterior Segment," American J. Opthamology, 142(5):777-787 (2006).
Olsen, T., "Drug Delivery to the Suprachoroidal Space Shows Promise," Retina Today, pp. 36-39 (Mar./Apr. (2007).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Patel, S. et al., "Suprachoroidal Drug Delivery Using Microneedles," Invest. Ophthalmol. Vis. Sci., 49:E-Abstract 5006 (2008), 2 pages.
Patel, S. et al., "Drug Binding to Sclera," Invest Ophthalmol Vis Sci., 50:E-Abstract 5968 (2009), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Patel, S. R. et al., "Suprachoroidal drug delivery to the back of the eye using hollow microneedles," Pharmaceutical Research, 28(1):166-176 (2011). Published online: Sep. 21, 2010.
Penkov, M. A. et al., "A ten-year experience with usage of the method of supra-choroidal administration of medicinal substances," Oftalmol. Zh., 35(5):281-285 (1980) (Translated from Russian).
Prausnitz, M. R. et al., "Permeability of cornea, sclera and conjunctiva: A literature analysis for drug delivery to the eye," Journal of Pharmaceutical Sciences, 87(12):1479-1488 (1998).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Rowe-Rendleman, C. L. et al., "Prophylactic Intra-Scleral Injection of Steroid Compounds in Rabbit Model of Retinal Neovascularization," Invest Ophthalmol Vis. Sci.,43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Sallam, A. et al., "Repeat intravitreal triamcinolone acetonide injections in uveitic macular oedema," Acta Ophthalmologica, 90(4):e323-e325 (2012).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Shuler, R. K. et al., "Scleral Permeability of a Small, Single-Stranded Oligonucleotide," Journal of Ocular Pharmacology and Therapeutics, 20(2):159-168 (2004) (Abstract).
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) (English Abstract).
Office Action for U.S. Appl. No. 16/591,067, mailed Nov. 18, 2019, 7 pages.
International Search Report and Written Opinion for International Application No. PCT/US2018/030688, mailed Aug. 8, 2018, 22 pages.
Keraliya, R. A. et al., "Osmotic Drug Delivery System as a Part of Modified Release Dosage Form," ISRN Pharmaceuticals, 2012, vol. 2012, Article ID 528079. doi: 10.5402/2012/528079. Epub Jul. 17, 2012, 9 pages.
Supplementary European Search Report for European Application No. 14808034.4, mailed Jan. 23, 2017, 7 pages.
Office Action for European Application No. 14808034.4, mailed Nov. 8, 2017, 4 pages.
Office Action for U.S. Appl. No. 14/894,161, mailed Dec. 27, 2016, 17 pages.
Office Action for U.S. Appl. No. 14/894,161, mailed Sep. 20, 2017, 21 pages.
Office Action for U.S. Appl. No. 14/894,161, mailed Apr. 6, 2018, 19 pages.
International Search Report and Written Opinion for International Application No. PCT/US2014/040254, mailed Oct. 31, 2014, 9 pages.
Decision of Final Rejection for Chinese Application No. 201580044250.8, dated Nov. 28, 2019, 14 pages.
Office Action for Canadian Application No. 162010, dated Aug. 25, 2015, 1 page.
International Search Report and Written Opinion for International Application No. PCT/US2014/071623, mailed Jun. 25, 2015, 18 pages.
Office Action for Brazilian Application No. PI 0708133-2, dated Feb. 26, 2019, 11 pages.
Office Action for Chinese Application No. 200780014501.3, dated Mar. 11, 2010, 6 pages.
Office Action for Chinese Application No. 200780014501.3, dated Aug. 26, 2010, 10 pages.
Office Action for European Application No. 07751620.1, dated Sep. 13, 2013, 7 pages.
Extended European Search Report for European Application No. 07751620.1, mailed Jan. 15, 2013, 10 lpages.

(56) References Cited

OTHER PUBLICATIONS

Office Action for European Application No. 07751620.1, dated Dec. 11, 2014, 5 pages.
Invitation pursuant to Article 94(3) and Rule 71(1) for European Application No. 07751620.1, mailed Feb. 29, 2016, 3 pages.
Summons to Attend Oral Proceedings Pursuant to Rule 115(1) EPC for European Application No. 07751620.1, mailed Jun. 13, 2017, 8 pages.
Office Action for Japanese Application No. 2008-556462, dated Jul. 24, 2012, 15 pages.
Office Action for Indian Application No. 3345/KOLNP/2008, dated May 21, 2015, 3 pages.
Office Action for Singapore Application No. 200805936-2, dated Oct. 15, 2012, 7 pages.
Search Report and Written Opinion for Singapore Application No. 200805936-2, dated Jun. 8, 2010, 13 pages.
Supplementary Search Report for Singapore Application No. 200805936-2, dated May 6, 2011, 8 pages.
Supplementary Search Report for Singapore Application No. 200805936-2, dated May 26, 2011, 8 pages.
Office Action for U.S. Appl. No. 11/709,941, mailed Jun. 24, 2014, 11 pages.
Office Action for U.S. Appl. No. 11/709,941, mailed Mar. 23, 2011, 9 pages.
Office Action for U.S. Appl. No. 11/709,941, mailed Feb. 11, 2015, 14 pages.
Office Action for U.S. Appl. No. 11/709,941, mailed Oct. 27, 2011, 8 pages.
Office Action for U.S. Appl. No. 11/709,941, mailed Apr. 12, 2016, 25 pages.
Office Action for U.S. Appl. No. 11/709,941, mailed Dec. 27, 2016.
Office Action for U.S. Appl. No. 11/709,941, mailed Jan. 16, 2018, 32 pages.
Office Action for U.S. Appl. No. 11/709,941, mailed Dec. 14, 2018, 17 pages.
International Search Report and Written Opinion for International Application No. PCT/US2007/004874, mailed Jun. 4, 2008, 6 pages.
Office Action for Chinese Application No. 201110093644.6, dated Mar. 26, 2012, 11 pages.
Office Action for Chinese Application No. 201110093644.6, dated Sep. 7, 2012, 8 pages.
Office Action for Chinese Application No. 201110093644.6, dated Dec. 14, 2012, 3 pages.
Extended European Search Report for European Application No. 18176149.5, mailed Jan. 22, 2019, 11 pages.
Office Action for U.S. Appl. No. 13/842,218, mailed Jul. 5, 2016, 11 pages.
Office Action for U.S. Appl. No. 13/842,288, mailed Oct. 6, 2015, 10 pages.
Office Action for U.S. Appl. No. 15/398,538, mailed Jul. 20, 2018, 12 pages.
Office Action for U.S. Appl. No. 15/398,538, mailed Apr. 16, 2019, 8 pages.
First Office Action for Chinese Application No. 201180060268.9, issued Oct. 10, 2014, 9 pages.
Second Office Action for Chinese Application No. 201180060268.9, issued Jun. 18, 2015, 4 pages.
Third Office Action for Chinese Application No. 201180060268.9, issued Feb. 5, 2016, 6 pages.
Examination Report for European Application No. 11776049.6, mailed Oct. 25, 2016, 4 pages.
Office Action for Japanese Application No. 2013-534049, mailed Sep. 1, 2015, 11 pages.
Office Action for U.S. Appl. No. 13/273,775, mailed Feb. 12, 2015, 13 pages.
Office Action for U.S. Appl. No. 13/273,775, mailed Jul. 3, 2014, 12 pages.
International Search Report and Written Opinion for International Application No. PCT/US2011/056433, mailed Apr. 25, 2012, 17 pages.
Office Action for Chinese Application No. 201510144330.2, issued Apr. 5, 2016, 17 pages.
Second Office Action for Chinese Application No. 201510144330.2, issued Dec. 20, 2016, 13 pages.
Third Office Action for Chinese Application No. 201510144330.2, issued Jun. 28, 2017, 3 pages.
Extended European Search Report for European Application No. 18199418.7, mailed Jul. 5, 2019, 9 pages.
Office Action for U.S. Appl. No. 14/821,310, mailed Jul. 14, 2017, 11 pages.
First Office Action for Chinese Application No. 201610805842.3, issued Jul. 21, 2017, 4 pages.
Extended European Search Report for European Application No. 17750694.6, mailed Sep. 2, 2019, 6 pages.
Office Action for U.S. Appl. No. 15/427,823, mailed Apr. 20, 2017, 8 pages.
Office Action for U.S. Appl. No. 15/427,823, mailed Sep. 27, 2017, 7 pages.
Office Action for U.S. Appl. No. 15/427,823, mailed Jul. 20, 2018, 11 pages.
International Search Report and Written Opinion for International Application No. PCT/US2017/017014, mailed Apr. 27, 2017, 13 pages.
International Search Report and Written Opinion for International Application No. PCT/US2017/012755, mailed Apr. 12, 2017, 8 pages.
International Search Report and Written Opinion for International Application No. PCT/US2017/012757, mailed Apr. 12, 2017, 11 pages.
International Search Report and Written Opinion for International Application No. PCT/US2017/030439, mailed Aug. 1, 2017, 12 pages.
Beer, P. J. et al., "Photographic Evidence of Vitreous Wicks After Intravitreal Injections," Retina Today, 2(2):24-39 (Mar. 2007).
Brown, D. M., "Aflibercept for Treatment of Diabetic Macular Edema," Retina Today, Jul./Aug. 2011, pp. 59-60.
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).
Dinning, W. J., "Steroids and the eye-indications and complications," Postgraduate Medical Journal, vol. 52, 1976, pp. 634-638.
Mansoor, S. et al., "Pharmacokinetics and Biodistribution of Triamcinolone Acetonide Following Suprachoroidal Injection into the Rabbit Eye In Vivo Using a Microneedle," Investigative Ophthalmology & Visual Science, ARVO Annual Meeting Abstract, Apr. 2011, vol. 52, 6585, 2 pages.

\* cited by examiner

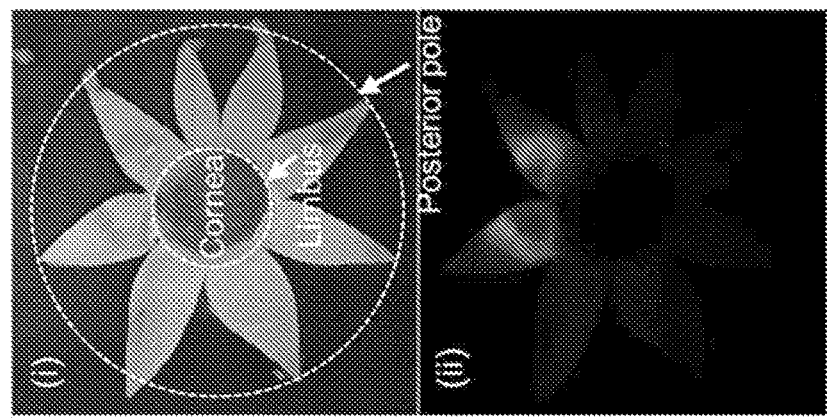
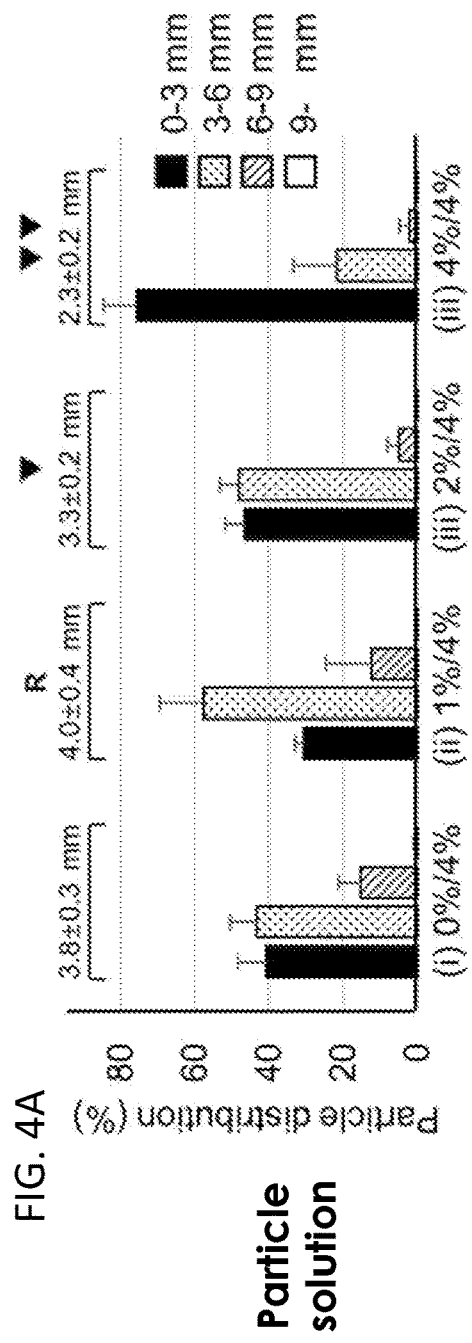
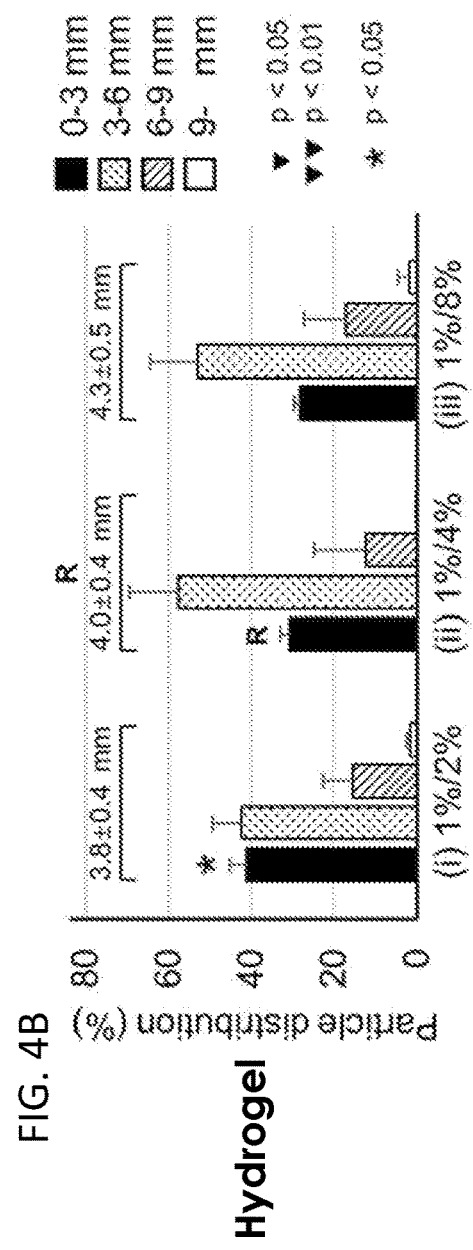
FIG. 4A Particle solution
FIG. 4B Hydrogel
FIG. 4C Before incubation After the incubation for 6 hr at 37 °C

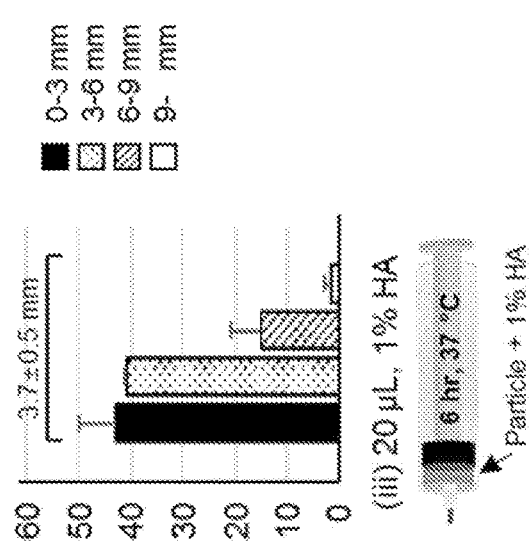
FIG. 8A
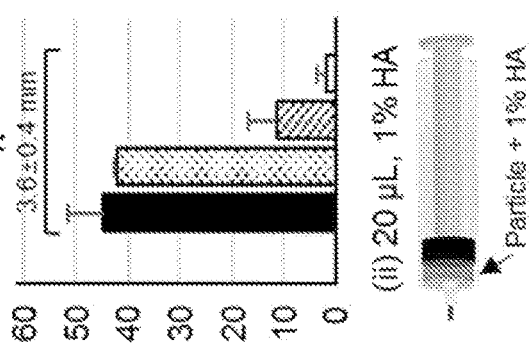
FIG. 8B
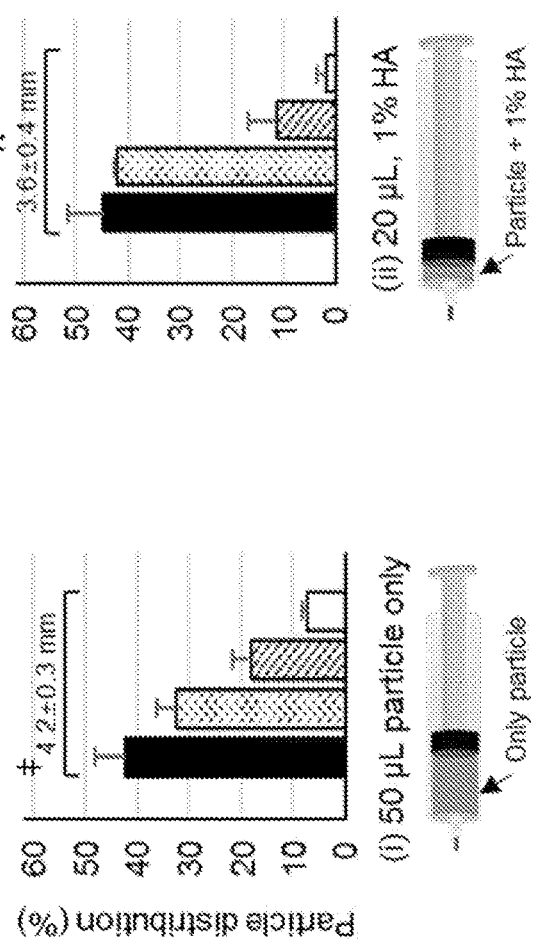
FIG. 8C
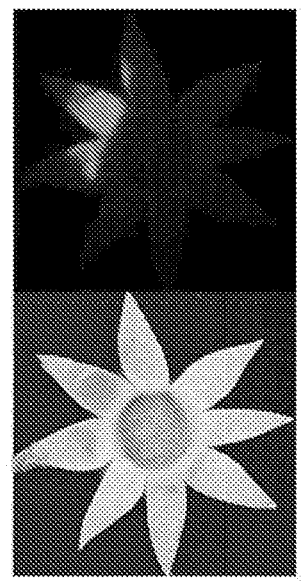
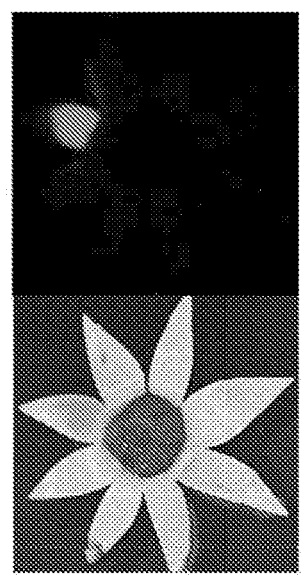
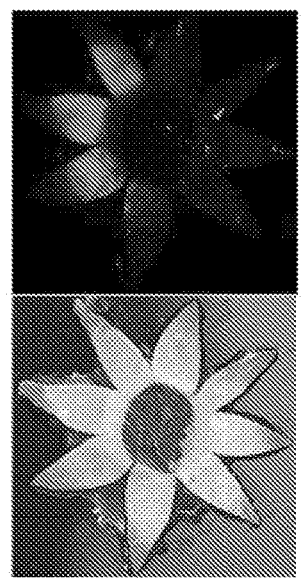

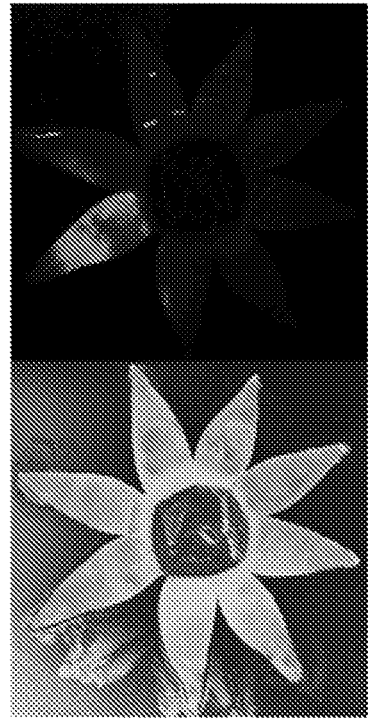
FIG. 11A (iii) 6 hr, 37 °C (HS_HA)
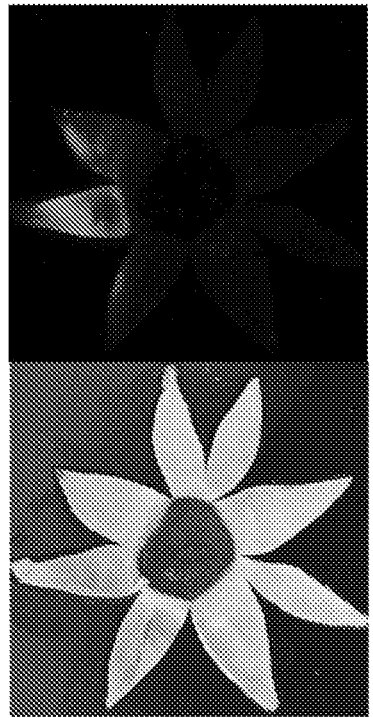
FIG. 11B (iv) 2 d (in vivo)

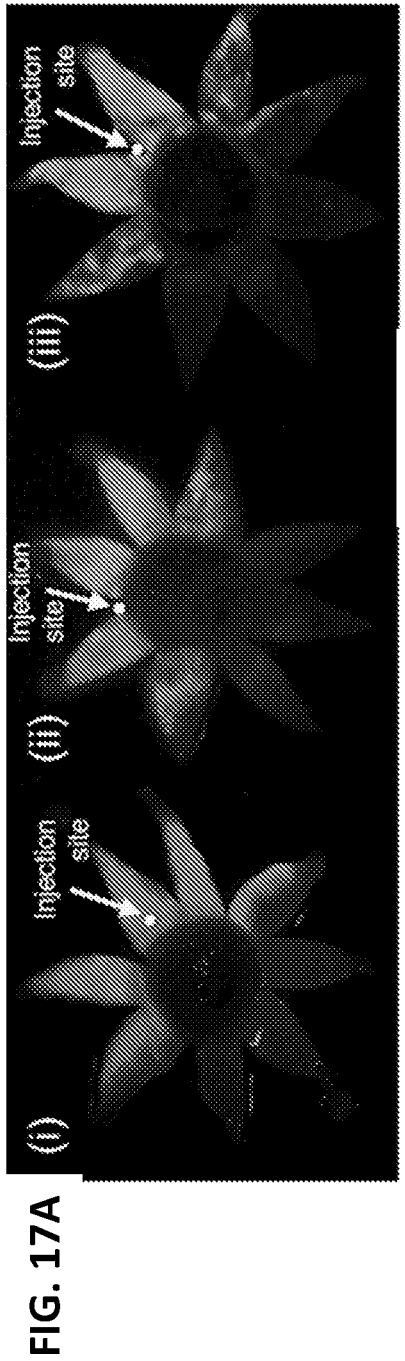
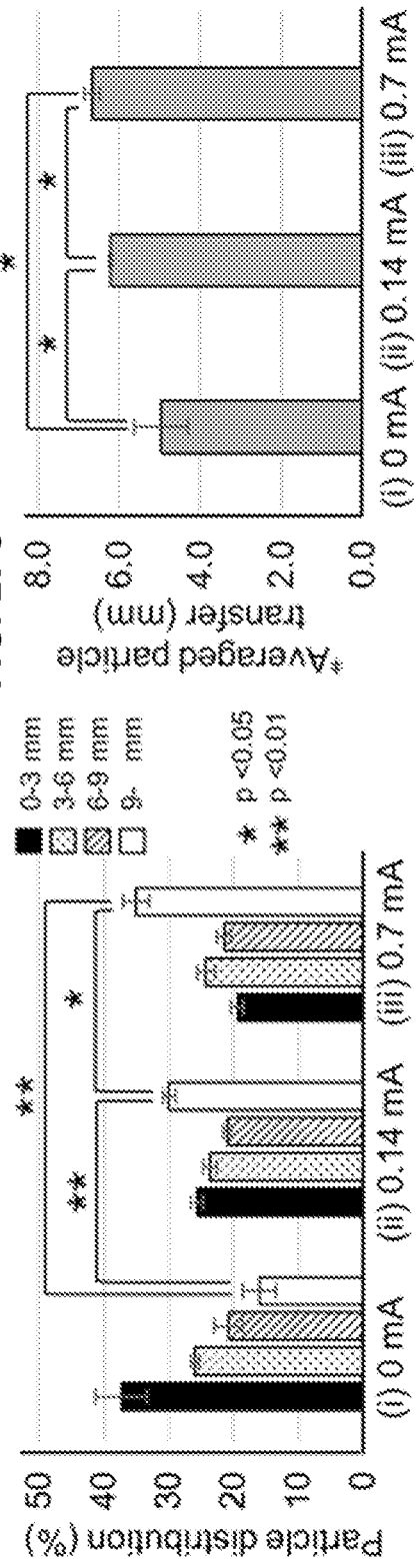
FIG. 17A
FIG. 17B
FIG. 17C

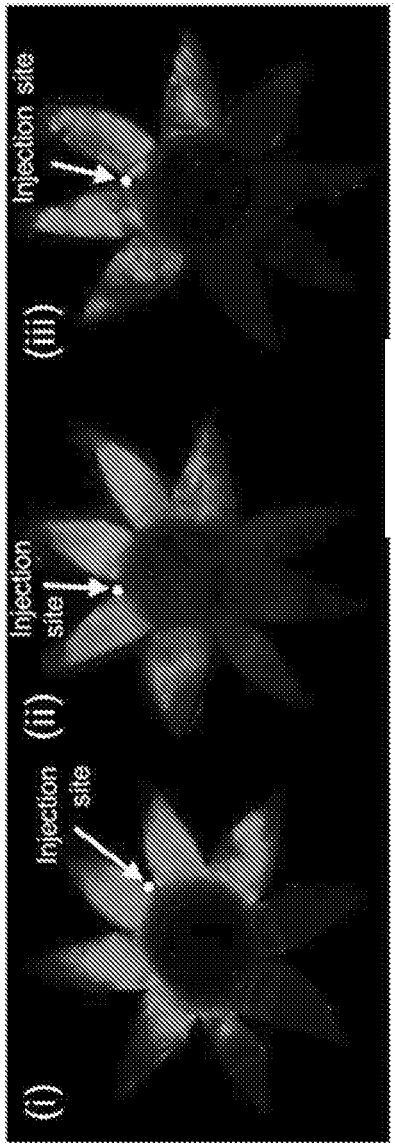
FIG. 18A
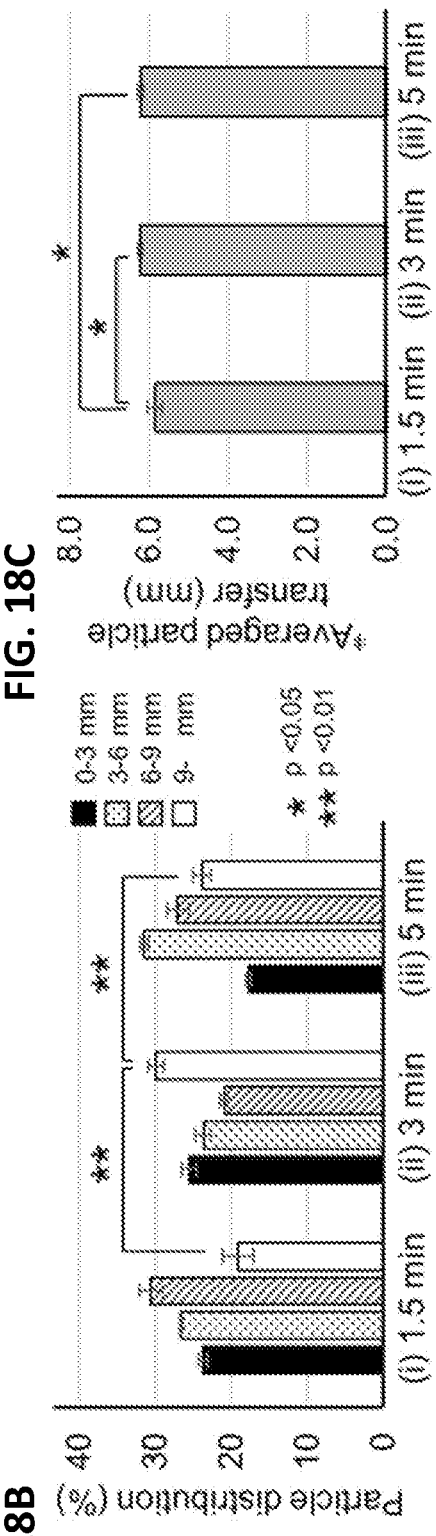
FIG. 18B
FIG. 18C

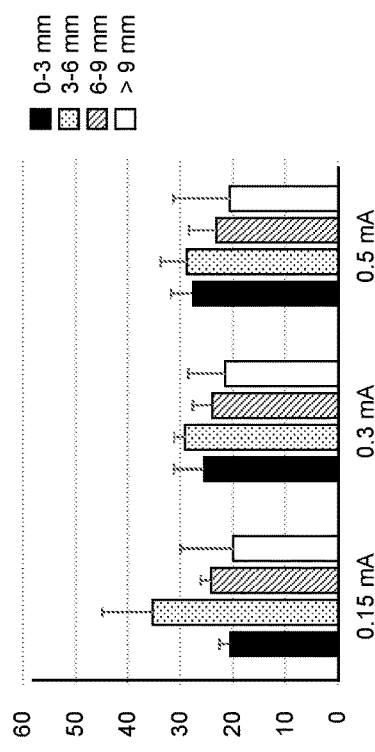
FIG. 28A Iontophoresis only 50 uL
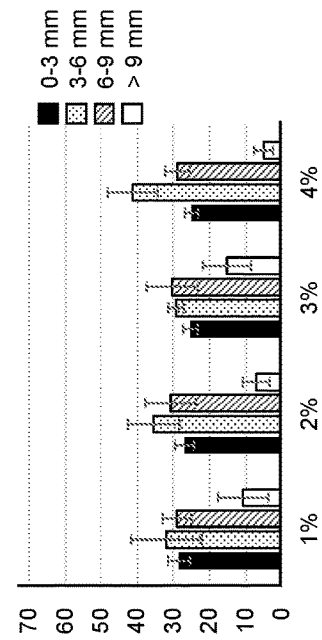
FIG. 28B Hydrogel optimization gel+particle

TARGETED DRUG DELIVERY METHODS USING A MICRONEEDLE

CROSS-REFERENCE TO RELATED APPLICATIONS

This application is the National Stage of International Application No. PCT/US2018/030688, filed May 2, 2018, which claims priority to and the benefit of U.S. Provisional Patent Application Ser. No. 62/500,209, filed May 2, 2017; the disclosure of which is incorporated herein by reference in their entireties.

BACKGROUND

The embodiments described herein relate generally to the field of drug delivery and more particularly to systems, devices, methods, and kits for targeted delivery of a substance into ocular tissues.

The anterior region of the eye refers to the front portion of the eye and includes structures in front of the vitreous humour such as the cornea, iris, ciliary body and lens. The posterior region of the eye refers to the back portion of the eye (i.e., the portion of the eye behind the lens), and includes the vitreous humor, retina, choroid, and optic nerve. The sclera is an opaque, fibrous, protective outer layer of the eye. The sclera includes connective tissue that maintains the shape of the eye by offering resistance to internal and external forces. The suprachoroidal space is the potential space or area between the sclera and choroid in the posterior region of the eye. Many inflammatory and proliferative diseases in the posterior region of the eye require long-term pharmaceutical treatment.

Although there are known methods of delivery of substances (e.g., drugs) into the posterior region of the eye, there is a need for improved devices and methods. It is often difficult to deliver effective doses of a drug to the back of the eye using conventional delivery methods such as topical application, intravitreal administration (IVT), or systemic administration. For example, topical applications, such as eye drops, are useful in treating conditions affecting the exterior surface of the eye or tissues at the front of the eye, however, eye drops are often not sufficiently conveyed to the back of the eye, as may be required for treatment of some retinal diseases such as macular degeneration, diabetic retinopathy, uveitis, and the like. Moreover, there is a short drug-eye contact time using eye drops, which can lead to more frequent applications of the drug. Other topical applications, such as ointments, allow a prolonged drug-eye contact time, thus requiring less frequent applications, but the application process increases the possibility of contamination since the drug is often applied via a person's hand. Furthermore, drugs that are administered via topical application are hindered from reaching the posterior region of the eye by components of the anterior region of the eye, as well as physiologic processes such as tears, blinking, drug metabolism, and drug binding.

Some known methods of treatment employ intravitreal (IVT) administration. IVT administration can include multiple injections due to the limited half-life of many compounds in the vitreous, potentially causing trauma and increase the risk of cataract, retinal detachment, hemorrhage and endophthalmitis.

The delivery of drugs to the posterior region of the eye through systemic administration is limited by the outer and inner blood-retinal barriers. Moreover, other limitations for systemic application of drugs include potentially reduced time of therapeutic effects and potency due to the dilution and degradation of the drug before reaching the target tissue. Thus, systemic administration usually requires an increase in the quantity of drugs necessary to achieve therapeutic concentrations at the target tissue, which increases the risk of adverse effects due to the accumulation of the drug in other tissues throughout the body.

The suprachoroidal space (SCS) of the eye has been studied as a location for drug delivery to posterior segments. The SCS can be reached via surgical means and/or cannulation. Although SCS delivery improves targeting to sites of drug action compared to other means such as topical, intravitreal, or systemic administration, it would be advantageous to achieve precisely controlled targeting to desired sites of drug action within the eye. This disclosure addresses this and other needs.

SUMMARY

Drug delivery to the suprachoroidal space (SCS) using a microneedle targets drugs to the choroid and adjacent retina. Although SCS delivery improves targeting to sites of drug action, further control of drug distribution and targeting to specific tissues and areas in specific tissues of the eye will enable more precise drug targeting, and more effective treatment. The present disclosure provides methods, systems, devices, and compositions for targeted drug delivery to ocular tissues, comprising the use of a pushing formulation and/or iontophoresis. In one aspect, the present disclosure provides methods for delivery of a drug formulation to a target tissue in the eye of a subject, the method comprising administering to the suprachoroidal space (SCS) of the subject a first formulation and a second formulation, wherein the first formulation comprises an active agent and the second formulation is a pushing formulation. In some embodiments, the pushing formulation is a formulation of higher density and/or viscosity relative to the first formulation such that the administration of the pushing formulation following the first formulation results in pushing the first formulation toward the posterior segment of the eye.

In one aspect, the present disclosure provides methods for delivery of a drug formulation to a target tissue in the eye of a subject, the method comprising administering to the suprachoroidal space (SCS) of the subject a formulation comprising an active agent and further comprising applying iontophoresis to the eye of the subject to localize the active agent to a target tissue in the eye. In one aspect, the present disclosure provides methods for delivery of a drug formulation to a target tissue in the eye of a subject, the method comprising using a combination of a pushing formulation and iontophoresis.

In some embodiments, the first formulation and the second formulation are administered to the SCS using a microneedle. In some embodiments, the microneedle is a hollow microneedle. In some embodiments, the microneedle is between about 600 μm and about 1200 μm in length. In further embodiments, the microneedle is between about 900 and 1100 μm in length. In further embodiments, the microneedle is about 750 μm in length. In some embodiments, the microneedle is about 900 μm in length. In some embodiments, the microneedle is about 1100 μm in length. In some embodiments, the microneedle size is 28 gauge or smaller. For example, in some embodiments, the microneedle is a 30 gauge microneedle, a 31 gauge microneedle, a 32 gauge microneedle, or a 33 gauge microneedle.

In some embodiments, the first formulation and the second formulation are administered to the SCS using a device containing both the first and second formulation. In some embodiments, the first formulation is administered to the SCS prior to administration to the SCS of the pushing formulation. In some embodiments, the first formulation has a lower viscosity than the pushing formulation. In some embodiments, the first formulation has a lower density than the pushing formulation. In some embodiments, the pushing formulation comprises a gel. In some embodiments, the pushing formulation comprises hyaluronic acid (HA). In some embodiments, the pushing formulation comprises about 1% (w/v), about 2% (w/v), about 3% (w/v), about 4% (w/v), or about 5% (w/v) HA. In some embodiments, the pushing formulation comprises a salt. For example, in some embodiments, the pushing formulation is a high-salt formulation. For example, in some embodiments, the pushing formulation comprises 9% sodium chloride (NaCl). In certain embodiments, the pushing formulation comprises about 4% (w/v) HA and about 9% NaCl.

In some embodiments, the first formulation comprises an active agent useful in the treatment of an ocular disease or disorder. In some embodiments, the first formulation comprises particles, e.g., a suspension of particles. In certain embodiments, the particles are microparticles or nanoparticles. In some embodiments, the first formulation comprising the active agent further comprises HA. In some embodiments, the first formulation comprises about 0.1% (w/v) HA, about 0.5% (w/v) HA, about 1% (w/v) HA, about 2% (w/v) HA, or about 3% (w/v) HA. In certain embodiments, the first formulation comprises about 1% (w/v) HA. In some embodiments, the first formulation comprises about 1% (w/v) HA and the pushing formulation comprises about 4% (w/v) HA.

In some embodiments, the target tissue of the eye is selected from the group consisting of the posterior pole, optic nerve, choroid, retina, vitreous humor, macula, iris, or ciliary body. In some embodiments, the methods provided herein comprise the use of a pushing formulation that pushes the drug formulation further posteriorly in the posterior segment of the eye. In some embodiments, the methods provided herein result in localization of at least 10%, at least 20%, at least 30%, at least 40%, or at least 50% of the first formulation and/or the active agent therein to a location in the eye that is at least about 3 mm posterior to the limbus. In further embodiments, the methods provided herein result in localization of at least 10%, at least 20%, at least 30%, at least 40%, or at least 50% of the first formulation and/or the active agent therein to a location in the eye that is at least about 6 mm posterior to the limbus. In some embodiments, the methods provided herein result in localization of at least 10%, at least 20%, at least 30%, or more of the first formulation and/or the active agent therein to a location in the eye that is at least 9 mm posterior to the limbus.

In one aspect, the present disclosure provides a device comprising a microneedle and a syringe or drug formulation reservoir, wherein the device comprises a first formulation and a second formulation, wherein the first formulation comprises an active agent and the second formulation is a pushing formulation. In some embodiments, the syringe is coupled to a microneedle. In some embodiments, the first formulation and the second formulation are substantially separate. For example, in some embodiments, the term "substantially separate" means there is little mixing or substantially no mixing of the first formulation and the second formulation. In some embodiments, there is mixing of the first and second formulations prior to, during, and/or after infusion of the formulations into the SCS, but the extent of the mixing does not prevent the pushing of the first formulation comprising the active agent further posteriorly in the posterior segment of the eye.

In some embodiments, the ocular disease or disorder is selected from the group consisting of uveitis, retinal vein occlusion, diabetic retinopathy, macular edema, diabetic macula edema, age-related macular degeneration, and glaucoma. In some embodiments, the disease or disorder amenable to treatment with the methods and compositions provided herein is selected from the group consisting of retinal vein occlusion, diabetic retinopathy, diabetic macula edema, and age-related macular degeneration, wherein the first formulation is injected to the posterior segment of the eye, and wherein the pushing formulation further pushes the first formulation posteriorly in the posterior segment of the eye. In some embodiments, the present disclosure provides methods wherein the active agent or drug in the first formulation flows or diffuses to the retina. In some embodiments, the disease or disorder amenable to treatment with the methods and compositions provided herein is glaucoma, and wherein the pushing formulation pushes the first formulation to the ciliary body.

In some embodiments, the present disclosure provides the use of a first formulation and a second formulation in a method of delivering a drug formulation to a target tissue in the eye of a subject, wherein the first formulation and second formulation are delivered to the suprachoroidal space (SCS) of the eye of the subject, wherein the first formulation comprises an active agent and the second formulation is a pushing formulation. In some embodiments, the present disclosure provides a first formulation and a second formulation for use in a method of treating a posterior ocular disease or disorder in a subject in need thereof, wherein the first formulation and second formulation are delivered to the suprachoroidal space (SCS) of the eye of the subject, wherein the first formulation comprises an active agent and the second formulation is a pushing formulation.

In some embodiments, the present disclosure provides the use of a first formulation and a second formulation in a method of delivering a drug formulation to a target tissue in the eye of a subject, wherein the first formulation and second formulation are delivered to the suprachoroidal space (SCS) of the eye of the subject, wherein the first formulation comprises a pushing formulation and the second formulation comprises an active agent. In some embodiments, the methods provide a means for pushing the active agent of the second formulation anteriorly. For example, in some embodiments, the methods provide a means for pushing an active agent toward the limbus of the eye. For example, in some embodiments, the methods provide a means for targeting an active agent to the ciliary body. In some embodiments, the present disclosure provides methods for treating a disease or disorder in a subject in need thereof, the method comprising administering to the SCS of the eye of the subject a first formulation that is a pushing formulation, and subsequently administering to the SCS of the eye of the subject a second formulation comprising a drug or active agent. In some embodiments, the disease or disorder is glaucoma.

In some embodiments, the methods provided herein involve iontophoresis, wherein the formulation comprising the active agent is administered to a region of the eye, e.g., the SCS, prior to the application of iontophoresis to the eye. In some embodiments, the formulation comprising the active agent is administered to the SCS concurrently with the application of iontophoresis to the eye. In some embodiments, the iontophoresis applied to the eye comprises applying a current with an absolute value of about 0.05 mA to about 0.8 mA. In some embodiments, the iontophoresis applied to the eye comprises applying a current with an absolute value of about 0.01 to about 0.7 mA. In some embodiments, the current has an absolute value of about 0.07 mA, about 0.08 mA, about 0.09 mA, about 0.1 mA, about 0.11 mA, about 0.12 mA, about 0.13 mA, about 0.14 mA, about 0.15 mA, about 0.16 mA, about 0.17 mA, about 0.18 mA, about 0.19 mA, about 0.2 mA, about 0.25 mA, about 0.3 mA, about 0.35 mA, about 0.4 mA, or about 0.5 mA. In some embodiments, a positive or negative current is used with an active agent and/or particle having an opposite polarity, for example, to move the active agent further posteriorly after injection. In some embodiments, the current with an absolute value provided herein is a positive current and is used with an active agent and/or particle having a negative charge. In some embodiments, the current with an absolute value provided herein is a negative current and is used with an active agent and/or particle having a positive charge. In other embodiments, a positive or negative current is used with an active agent and/or particle having the same polarity, for example to keep the active agent in the anterior part of the SCS (e.g., the ciliary body) after injection. For example, in some embodiments, the current with an absolute value provided herein is a negative current and is used with an active agent and/or particle having a negative charge: or the current with an absolute value provided herein is a positive current and is used with an active agent and/or particle having a positive charge In some embodiments, the iontophoresis is applied to the eye for about 1 minute to about 10 minutes. In some embodiments, the iontophoresis is applied to the eye for about 3 minutes.

In one aspect, the present disclosure provides methods for delivery of a drug formulation to a target tissue in the eye of a subject, the method comprising (i) administering to SCS of the eye of the subject a first formulation and a second formulation, wherein the first formulation comprises an active agent and the second formulation is a pushing formulation: and (ii) applying iontophoresis to the eye of the subject to further localize the active agent to a target tissue in the eye. In some embodiments, the method results in localization of the active agent further posteriorly in the posterior segment of the eye, such as precise localization to desired tissues within the eye or specific areas on desired tissues within the eye. In some embodiments, the method results in localization of at least about 30% of the first formulation to a location in the eye that is at least about 6 mm posterior to the limbus. In further embodiments, method results in localization of at least about 50% of the first formulation to a location in the eye that is at least about 6 mm posterior to the limbus. In some embodiments, the iontophoresis is applied to the eye prior to the administration of the second formulation. In other embodiments, the iontophoresis is applied to the eye during and/or after administration of the second formulation. In one aspect, the present disclosure provides a method comprising (i) administering to the SCS of the eye of the subject a first formulation comprising an active agent: (ii) applying iontophoresis to the eye of the subject to localize the active agent to a target tissue in the eye: and (iii) administering to the SCS of the eye of the subject a second formulation, wherein the second formulation is a pushing formulation and wherein the second formulation further localizes the active agent to a target tissue in the eye.

BRIEF DESCRIPTION OF THE DRAWINGS

FIG. 4A shows the particle distribution (% of particles located at the indicated positions) when the pushing formulation is held at 4% HA and the drug particle formulation is tested at 0%, 1%, 2%, or 4% HA. The averaged particle transfer (APT) for each group is also shown at the top of the graph for each group. FIG. 4B shows the particle distribution (% of particles located at the indicated positions) when the drug particle formulation is held at 1% HA and the pushing formulation is tested at 2%, 4%, or 8% HA. The APT is also shown at the top of the graph for each group. Averaged particle transfer (APT) (mm)=(1.5 mm×the particle distribution % of 0-3 mm area)+(4.5 mm×the particle distribution % of 3-6 mm area)+(7.5 mm×the particle distribution % of 6-9 mm area)+(10.5 mm×the particle distribution % of 9—mm area). R is the reference value. ▼, ▼▼ Significance (One-way ANOVA) between the APT of the reference (R) and the APT of the other formulations. *Significance (One-way ANOVA) between the 0-3 mm distribution of the reference (R) and the other formulations. The average±standard deviation based on 3 replicate samples (avg±SD, n=3) is shown in both FIG. 4A and FIG. 4B. FIG. 4C shows the digital (i) and fluorescent (ii) images after dissection, when dissection was performed right after SCS injection.

FIG. 8A shows the particle distribution (bar graph) and bright field and fluorescent images immediately following SCS injection of 50 µL of red fluorescent particles in HBSS buffer (no HA). APT was 4.2+0.3 mm. FIG. 8B shows the particle distribution (bar graph) and bright field and fluorescent images immediately following SCS injection of 20 µL of particle in 1% HA. APT was 3.6+0.4 mm. FIG. 8C shows the particle distribution (bar graph) and bright field and fluorescent images following SCS injection of 20 µL of particle in 1% HA, after a 6 hour incubation at 37° C. APT was 3.7±0.5 mm. R is reference value. No Significance (One-way ANOVA) between the APT of the reference (R) and the APT of the formulations. Graphs (a) present average+standard deviation based on 3 replicate samples (avg±SD, n=3).

FIG. 11A shows the bright field and fluorescent images for the high-salt HA group (6 hour incubation at 37° C. FIG. 11B shows the bright field and fluorescent images for the in vivo injection of high-salt HA pushing formulation.

FIG. 17A provides fluorescence micrographs following SCS injection of red fluorescent particles and no iontophoresis (i), or iontophoresis at 0.14 mA (ii) or 0.7 mA (iii). The fluorescence micrographs show the representative flat mounts of the eyes after dissecting eyes with radial cuts from the posterior pole to the limbus. The arrows point to sites of injection into the SCS. FIG. 17B shows the particle distribution to the 0-3 mm, 3-6 mm, 6-0 mm, or 9—mm area in the SCS. *, ** Significance (One-way ANOVA, p<0.00127, 0.04985, and 0.00707, respectively) between (i) and (ii), (ii) and (iii), and (i) and (iii) of the 9— mm distributions. FIG. 17C shows the APT (mm) for each group. * Significance (One-way ANOVA, p<0.03026, 0.01636, and 0.01264, respectively) between (i) and (ii), (ii) and (iii), and (i) and (iii) of the APT. In FIGS. 17B and 17C, the graphs present average±standard deviation based on 3 replicate samples (avg±SD, n=3).

FIG. 18A provides fluorescence micrographs following SCS injection of red fluorescent particles and iontophoresis application time of 1.5 min (i), 3 min (ii), or 5 min (iii). The fluorescence micrographs show the representative flat mounts of the eyes after dissecting eyes with radial cuts from the posterior pole to the limbus. The arrows point to sites of injection into the SCS. FIG. 18B shows the particle distribution to the 0-3 mm, 3-6 mm, 6-0 mm, or 9—mm area in the SCS.  Significance (One-way ANOVA, p<0.00073 and 0.00791) between (i) and (ii), and (ii) and (iii) of the 9—mm distributions. FIG. 18C shows the APT (mm) for each group.  Significance (One-way ANOVA, p<0.01680 and 0.01932) between (i) and (ii), and (i) and (iii) of the APT. In FIGS. 18B and 18C, the graphs present average±standard deviation based on 3 replicate samples (avg±SD, n=3)

FIG. 23A provides fluorescent micrographs showing the distribution of the red-fluorescent particles in the SCS after injection at time 0 (i), 1 hour after injection (ii), and 1 week after injection (iii). The micrographs show representative flat mounts of the eyes after dissecting eyes with radial cuts from the posterior pole to the limbus. The arrows point to sites of injection into the SCS. FIG. 23B shows the particle distribution percent after injection at each time point. *, ** Significance (One-way ANOVA, p<0.0064 and 0.0487) between (i) and (ii), and (ii) and (iii) of the 9—mm distributions. FIG. 23C shows the APT at each time point. *, ** Significance (One-way ANOVA, p<0.00401 and 0.04367) between (i) and (ii), and (i) and (iii) of the APT. For FIGS. 23B and 23C, graphs present average±standard deviation based on 3 replicate samples (avg±SD, n=3).

FIG. 28A shows the results of different current conditions for injection of 50 μL drug particle formulation (without pushing formulation). Current conditions of 0.15 mA, 0.3 mA, and 0.5 mA were tested. FIG. 28B shows the results of different HA formulations for the pushing formulation (tested in the absence of iontophoresis). 1% HA, 2% HA, 3% HA, and 4% HA formulations were tested.

DETAILED DESCRIPTION

Figure 1:
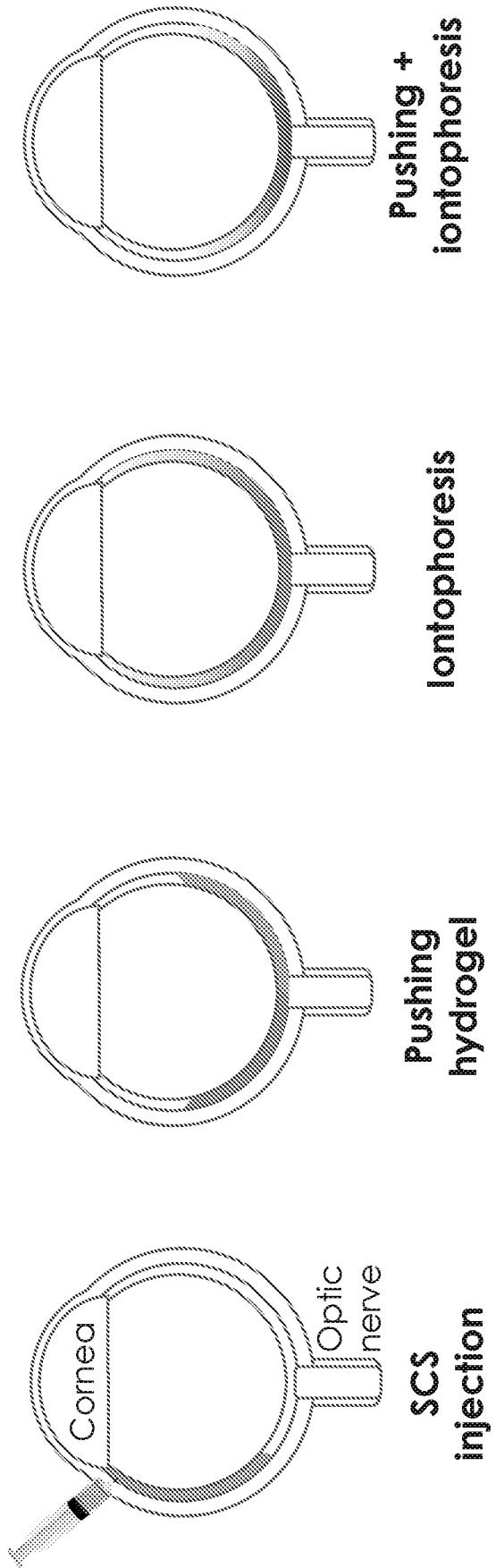
FIG. 1 provides schematic views of a cross-section of a human eye and an SCS injection thereof. Schematic diagrams of the eye following pushing hydrogel, iontophoresis, and combination pushing with iontophoresis embodiments of the present disclosure are also provided.

Devices, methods, systems, compositions, and kits for ocular drug delivery are described herein. FIG. 1 shows representative schematic diagrams of the pushing hydrogel, iontophoresis, and combined pushing with iontophoresis methods provided herein. In one aspect, the present disclosure provides methods for better drug delivery to the target tissue or site of action of drugs in the eye of a subject, via methods including injection into the suprachoroidal space (SCS) of the eye of the subject. For example, in some embodiments, the present disclosure provides systems, methods, and compositions for targeted delivery to one or more tissues such as the ciliary body, retina, choroid, and/or macula. In some embodiments, the systems, methods, and compositions involve injection of one or more formulations into the SCS of the eye, and control the delivery to the particular target tissues within the eye. For many indications (e.g., glaucoma, uveitis, macular degeneration), the sites of action can be at various locations around the eye that can be accessed via the SCS. Accordingly, targeted drug delivery within the SCS by accurate control of the drug localization is of interest to reduce potential risks of side-effects, such as those side effects caused by drugs spread off-target or widely spread adjacent to target tissues. In addition, targeted delivery within the SCS by accurate control of the drug localization increases drug concentration and efficacy at the site(s) of action. In one aspect, the present disclosure provides two novel targeted ocular drug delivery systems. One is driven by "hydrogel pushing" and one is driven by iontophoresis. In some embodiments, a combination of the hydrogel pushing and iontophoresis methods is provided. The methods provided herein are useful in treatment of diverse ocular diseases.

As used herein, "ocular tissue" and "eye" include both the anterior segment of the eye (i.e., the portion of the eye in front of the lens) and the posterior segment of the eye (i.e., the portion of the eye behind the lens).

The term "suprachoroidal space," is used interchangeably with suprachoroidal, SCS, suprachoroid and suprachoroidia, and describes the potential space in the region of the eye disposed between the sclera and choroid. This region primarily is composed of closely packed layers of long pigmented processes derived from each of the two adjacent tissues: however, a space can develop in this region as a result of fluid or other material buildup in the suprachoroidal space and the adjacent tissues. The "supraciliary space," as used herein, is encompassed by the SCS and refers to the most anterior portion of the SCS adjacent to the ciliary body, trabecular meshwork and limbus. Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug formulation into the suprachoroid to create the suprachoroidal space (which is filled with drug formulation). Not wishing to be bound by theory, it is believed that the SCS region serves as a pathway for uveoscleral outflow (i.e., a natural process of the eye moving fluid from one region of the eye to the other through) and becomes a real space in instances of choroidal detachment from the sclera.

As used herein, "non-surgical" ocular drug delivery devices and methods refer to methods and devices for drug delivery that do not require general anesthesia and/or retrobulbar anesthesia (also referred to as a retrobulbar block). Alternatively or additionally, a "non-surgical" ocular drug delivery method is performed with an instrument having a diameter of 28 gauge or smaller. Alternatively or additionally, "non-surgical" ocular drug delivery methods do not require a guidance mechanism that is typically required for ocular drug delivery via a shunt or cannula. As used herein, "surgical" ocular drug delivery includes insertion of devices or administration of drugs by surgical means, for example, via incision to expose and provide access to regions of the eye including the posterior region, and/or via insertion of a stent, shunt, or cannula. In certain aspects, the non-surgical methods for delivery to the SCS provided herein are achieved by injecting a drug or drug formulation to the SCS using a microneedle.

In some embodiments, features of the devices, formulations, and methods are provided in International Patent Application Publication Nos. WO2014/074823 (Application No. PCT/US2013/069156), WO2015/195842 (Application No. PCT/US2015/036299), and/or WO2017/120601 (Application No. PCT/US2017/012757), each of which is hereby incorporated by reference in its entirety for all purposes.

In some embodiments, the present disclosure provides systems, methods, and compositions wherein a drug formulation (e.g., a formulation containing an active agent) may be delivered to a particular action site depending on the ocular disease for which the subject is being treated. Exemplary target sites, associated indications, and active agents or drug formulations for treatment of the indication are provided below. The person of ordinary skill in the art will appreciate that other target sites, indications, and active agents/drug formulations are encompassed by the invention. For example, the present disclosure provides compositions and methods for delivery of active agents and drug formulations to the optic nerve. Other target sites, indications, and active agents include, without limitation:

Conjunctiva: for treatment of conjunctivitis (e.g., antibiotic injection)

Cornea: for treatment of infectious keratitis (antimicrobial agent), non-infectious keratitis (steroid agent), corneal ulcer (antifungal/antiviral agent)

Sclera: for treatment of Scleritis (non-steroidal anti-inflammatory agent or steroid agent)

Uvea: for of treatment Uveitis (Iris, ciliary body, choroid), anterior/intermediate/posterior/panuveitis (steroid agent and immunosuppressant)

Ciliary body: for treatment Glaucoma (prostaglandin agent)

Retina: for treatment of retinal vein occlusion, diabetic retinopathy, diabetic macula edema, and age-related macular degeneration (anti-VEGF and steroid agent)

Ocular diseases and disorders amenable for treatment by the methods, systems, compositions, kits, devices, and drug formulations described herein can include, but are not limited to, uveitis (e.g., infectious uveitis, non-infectious uveitis, chronic uveitis, and/or acute uveitis), macular edema, diabetic macular edema (DME), macular edema associated with uveitis (encompassing macular edema associated with infectious uveitis and macular edema associated with non-infectious uveitis), macular edema following retinal vein occlusion (RVO), and macular edema associated with RVO. In one embodiment, the posterior ocular disorder is an ocular inflammatory condition such as uveitis, scleritis, glaucoma, ocular sarcoidosis, optic neuritis, macular edema, diabetic retinopathy, macular degeneration, a corneal ulcer, an autoimmune disorder, ophthalmic manifestations of AIDS, optic nerve degeneration, geographic atrophy, choroidal disease, retinitis, ocular neovascularization, polypoidal choroidal vasculopathy, choroidal sclerosis, central sirrus choroidopathy, a multi-focal choroidopathy or a choroidal dystrophy (e.g., central gyrate choroidal dystrophy, serpiginous choroidal dystrophy, total central choroidal atrophy The condition in one embodiment is acute. In another embodiment, the condition is chronic.

Disorders caused by pathogenic organisms that can lead to infectious uveitis, macular edema associated with infectious uveitis, or other ocular disorders amenable to the treatment methods, systems, and compositions provided herein include, but are not limited to, toxoplasmosis, toxocariasis, histoplasmosis, herpes simplex or herpes zoster infection, tuberculosis, syphilis, sarcoidosis, Vogt-Koyanagi-Harada syndrome, Behcet's disease, idiopathic retinal vasculitis, Vogt-Koyanagi-Harada Syndrome, acute posterior multifocal placoid pigment epitheliopathy (APMPPE), presumed ocular histoplasmosis syndrome (POHS), birdshot chroidopathy, Multiple Sclerosis, sympathetic opthalmia, punctate inner choroidopathy, pars planitis, or iridocyclitis.

The term "subject" may be used interchangeably herein with "patient" and the like. In some embodiments, the subject is any animal, including any mammal. In some embodiments, the subject is a human. In some embodiments, the subject is a human subject in need of treatment of an ocular disease or disorder.

Delivery Materials

Drugs, molecules, particles, hydrogels, polymers, diagnostics, therapeutics, cosmetics/cosmeceuticals, prostheses/implants and other agents (materials) can be delivered into the suprachoroidal space of the eye. The material to be delivered could carry a positive charge, negative charge or no charge, and if zwitterionic, a net positive charge, net negative charge or no net charge. Thus, in some embodiments, the active agent or drug formulation useful in the compositions, methods, and systems provided herein comprises a charged moiety. The charged moiety may be created using any known technique, and generally may include a moiety that is altered to have a different charge (i.e., neutral to positive, neutral to negative, negative to positive, etc.), an increased charge, or decreased charge. In some embodiments, the charged moiety is a moiety that is positively charged under assay or physiological conditions, which are typically neutral or slightly acidic (pH about 5 to about 7). The positively charged moiety may include an amine. In another embodiment, the charged moiety is a moiety that is negatively charged under assay or physiological conditions. The negatively charged moiety may include a carboxylate, a phosphate, or a combination thereof. In some embodiments, the "first formulation" or "active agent formulation" and the like comprises the charged moieties, drugs, molecules, particles, hydrogels, polymers, diagnostics, therapeutics, cosmetics/cosmeceuticals, prostheses/implants, other agents provided herein.

As provided throughout, in one embodiment, the methods described herein are carried out with a hollow or solid microneedle, for example, a rigid microneedle. As used herein, the term "microneedle" refers to a conduit body having a base, a shaft, and a tip end suitable for insertion into the sclera and other ocular tissue and has dimensions suitable for minimally invasive insertion and drug formulation infusion as described herein. That is, the microneedle has a length or effective length that does not exceed about 2000 microns and a diameter that does not exceed about 600 microns. Both the "length" and "effective length" of the microneedle encompass the length of the shaft of the microneedle and the bevel height of the microneedle. In some embodiments, the microneedle used to carry out the methods described herein comprises one of the devices disclosed in International Patent Application Publication No. WO2014/179698 (Application No. PCT/US2014/036590), filed May 2, 2014 and entitled "Apparatus and Method for Ocular Injection," incorporated by reference herein in its entirety for all purposes. In some embodiments, the microneedle used to carry out the methods described herein comprises one of the devices disclosed in International Patent Application Publication No. WO2014/036009 (Application No. PCT/US2013/056863), filed Aug. 27, 2013 and entitled "Apparatus and Method for Drug Delivery Using Microneedles," incorporated by reference herein in its entirety for all purposes.

In some embodiments, features of the devices, formulations, and methods are provided in International Patent Application Publication Nos. WO2014/074823 (Application No. PCT/US2013/069156), WO2015/195842 (Application No. PCT/US2015/036299), and/or WO2017/120601 (Application No. PCT/US2017/012757), each of which is hereby incorporated by reference in its entirety for all purposes. In one embodiment, the device used to carry out one of the methods described herein comprises the device described in U.S. Design Patent Application Ser. No. 29/506,275 entitled, "Medical Injector for Ocular Injection," filed Oct. 14, 2014, the disclosure of which is incorporated herein by reference in its entirety for all purposes. In one embodiment, the device used to carry out one of the methods described herein comprises the device described in U.S. Patent Publication No. 2015/0051581 or U.S. Patent Publication No. 2017/0095339, which are each incorporated by reference in their entireties for all purposes.

In some embodiments, the words "proximal" and "distal" when used herein in relation to an operator of the device refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a microneedle described herein first inserted inside the patient's body would be the distal end, while the opposite end of the microneedle (e.g., the end of the medical device being manipulated by the operator) would be the proximal end of the microneedle. In other embodiments, the words "proximal" and "distal" when used herein in relation to a device itself may refer to the direction closer to or away from, respectively, the indicated end of the device. Thus, in some embodiments, a microneedle coupled to a syringe containing an active agent formulation and a pushing formulation may comprise an active agent formulation that is proximal to the needle end and a pushing formulation distal from the needle end, such that upon insertion of the microneedle and infusion into the SCS of the eye, the active agent formulation enters the SCS prior to the entry into the SCS of the pushing formulation.

As used herein, the terms "about" and "approximately" generally mean plus or minus 10% of the value stated. For example, about 0.5 would include 0.45 and 0.55, about 10 would include 9 to 11, about 1000 would include 900 to 1100.

As used herein, the term "hollow" (e.g., in relation to a hollow microneedle) includes a single, straight bore through the center of the microneedle, as well as multiple bores, bores that follow complex paths through the microneedles, multiple entry and exit points from the bore(s), and intersecting or networks of bores. That is, a hollow microneedle has a structure that includes one or more continuous pathways from the base of the microneedle to an exit point (opening) in the shaft and/or tip portion of the microneedle distal to the base.

In one embodiment, the microneedle has an effective length of about 50 μm to about 2000 μm. In another particular embodiment, the microneedle has an effective length of from about 150 μm to about 1500 μm, or from about 300 μm to about 1250 μm, or from about 500 μm to about 1250 μm, or from about 500 μm to about 1500 μm, or from about 600 μm to about 1000 μm, or from about 700 μm to about 1000 μm. In one embodiment, the effective length of the microneedle is about 600 μm, or about 700 μm, or about 800 μm or about 1000 μm. In various embodiments, the proximal portion of the microneedle has a maximum width or cross-sectional dimension of from about 50 μm to 600 μm, or from about 50 μm to about 400 μm, or from about 50 μm to about 500 μm, or from about 100 μm to about 400 μm, or from about 200 μm to about 600 μm, or from about 100 μm to about 250 μm, with an aperture diameter of about 5 μm to about 400 μm. In a particular embodiment, the proximal portion of the microneedle has a maximum width or cross-sectional dimension of about 600 μm. Those skilled in the art will appreciate, however, that in embodiments in which the tip of the microneedle is beveled that the aperture diameter may be greater than the outer diameter of the proximal portion of the microneedle. The microneedle may be fabricated to have an aspect ratio (width:length) of about 1:1.5 to about 1:10. In one embodiment, the aspect ratio of the microneedle is about 1:3 to about 1:5. In another embodiment, the aspect ratio of the microneedle is about 1:4 to about 1:10.

The microneedle can have a straight or tapered shaft. In one embodiment, the diameter of the microneedle is greatest at the base end of the microneedle and tapers to a point at the end distal the base. The microneedle can also be fabricated to have a shaft that includes both a straight (i.e., untapered) portion and a tapered (e.g., beveled) portion. In various embodiments the microneedle has a bevel angle of about 5 degrees to about 30 degrees, of about 5 degrees to about 25 degrees, about 5 degrees to about 20 degrees, about 10 degrees to about 20 degrees, and about 10 degrees to about 30 degrees. The microneedles can be formed with shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off, or rounded. In various embodiments, the microneedle has a bevel height from about 50 μm to 500 μm, about 100 μm to about 500 μm, about 100 μm to about 400 μm, about 200 μm to about 400 μm, and about 300 μm to about 500 μm. In particular embodiments, the microneedle may be designed such that the tip portion of the microneedle is substantially the only portion of the microneedle inserted into the ocular tissue (i.e., the tip portion is greater than 75% of the total length of the microneedle, greater than 85% of the total length of the microneedle, or greater than about 95% of the total length of the microneedle). In other particular embodiments, the microneedle may be designed such that the tip portion is only a portion of the microneedle that is inserted into the ocular tissue and generally has a length that is less than about 75% of the total length of the microneedle, less than about 50% of the total length of the microneedle, or less than about 25% of the total length of the microneedle. For example, in one embodiment the microneedle has a total effective length between 500 μm and 1500 μm, wherein the tip portion has a length that is less than about 400 μm, less than about 300 μm, or less than about 200 μm.

In one embodiment, the height of the bevel is about 100 μm to about 500 μm. In another embodiment, the height of the bevel is about 500 μm or less, about 450 μm or less, about 400 μm or less or about 350 μm or less. In another embodiment, the height of the bevel is from about 200 μm to about 500 μm, or from about 100 μm to about 700 μm, or from about 200 μm to about 700 μm. In still other embodiments, the height of the bevel is from about 500 μm to about 900 μm, or from about 500 μm to about 800 μm, or from about 500 μm to about 700 μm. In this manner, the arrangement of the bevel can be such that the distal edge is sufficiently sharp such as to pierce a target tissue and penetrate into the vitreous without (i) substantially causing the target tissue to elastically deform or (ii) damaging internal structures of the eye, e.g., the lens or retina.

In one embodiment, the microneedle extends from a base. The base may be integral with or separate from and coupled (e.g., slidably coupled or fixedly coupled) to the microneedle. The base may be rigid or flexible. The base may be substantially planar or it may be curved, for example, in the shape of the ocular tissue surface at the site of injection or, for example, curved away from the ocular surface (e.g., convex) so as to minimize contact between the base and the ocular tissue. In some embodiments, desirably, the base is shaped to provide minimal contact with the surface of the eye at the point of insertion. For example, in such embodiments, the base may extend only a minimal distance from the microneedle shaft substantially perpendicular. In another embodiment, the base may be shaped so as to elevate the ocular tissue towards the microneedle so as to counteract the deflection of the ocular tissue and facilitate insertion of the microneedle into the ocular tissue (e.g., the base may extend from the microneedle toward the tip portion of the microneedle so as to "pinch" the ocular tissue). Some such embodiments may be based, at least in part, on the devices described in U.S. Pat. No. 6,743,211, incorporated herein by reference.

Microneedles may be manufactured using techniques described, for example, in U.S. Patent Application Publication No. 2006/0086689, U.S. Patent Application Publication No. 2006/0084942, U.S. Patent Application Publication No. 2005/0209565, U.S. Patent Application Publication No. 2002/0082543, U.S. Pat. Nos. 6,334,856, 6,611,707, 6,743, 211 and PCT/US2014/36590, filed May 2, 2014, all of which are incorporated herein by reference in their entireties for all purposes.

In some embodiments, the microneedle comprises a fluid reservoir for containing the drug formulation and/or hydrogel pushing formulation. In some embodiments, the fluid reservoir is in operable communication with the bore of the microneedle at a location distal to the tip end of the microneedle. The fluid reservoir may be integral with the microneedle, integral with the elongated body, or separate from both the microneedle and elongated body. In some embodiments, the microneedle is coupled to, attached to, or configured to allow attachment to a syringe comprising the drug formulation and/or the hydrogel pushing formulation.

Devices shown and described in International Patent Application No. WO2015/19584, entitled "METHOD AND DEVICES FOR TREATING POSTERIOR OCULAR DISORDERS," and U.S. Pat. No. 9,180,047, entitled "APPARATUS AND METHODS FOR OCULAR INFECTION," each of which is incorporated herein by reference in its entirety, can be used to perform the SCS injection portion of the methods provided herein.

Any composition or drug formulation suitable for ocular delivery may be injected using any suitable injector of the types shown and described herein. Any of the methods described herein can be performed use any suitable injector of the types shown and described herein. In this manner, the benefits of the targeted drug delivery via the methods and compositions provided herein can be realized.

In some embodiments, the methods and systems provided herein comprise targeted delivery of a drug to a desired location in the eye, wherein the delivered volume is at least about 20 μL, at least about 50 μL, at least about 100 μL, at least about 200 μL or at least about 500 μL. In some embodiments, the delivered volume is from about 10 μL to about 200 μL, e.g., from about 50 μL to about 150 μL. In some embodiments, the delivered volume is about 50 μL, about 75 μL, about 100 μL, about 125 μL, about 150 μL, about 175 μL, about 200 μL, about 250 μL, about 300 μL, about 350 μL, about 400 μL, or about 500 μL.

In some embodiments, the targeting of a drug formulation to and/or within the posterior segment of the eye is measured by determining how much of the drug formulation (e.g., by volume or by percent) is localized at least 3 mm posterior to the limbus, at least 4 mm posterior to the limbus, at least 5 mm posterior to the limbus, at least 6 mm posterior to the limbus, at least 7 mm posterior to the limbus, at least 8 mm posterior to the limbus, at least 9 mm posterior to the limbus, or at least 10 mm posterior to the limbus. In some embodiments, the targeting of a drug formulation and/or within the posterior segment of the eye is measured by determining how much of the drug formulation (e.g., by volume or by percent) is localized about 0-3 mm posterior to the limbus, about 3-6 mm posterior to the limbus, about 6-9 mm posterior to the limbus, or about 9 or more mm posterior to the limbus.

Hydrogel Pushing

In some embodiments, the present disclosure provide methods for delivery in the SCS using a hydrogel pushing strategy. In some embodiments, the hydrogel pushing strategy involves a two-step process or a two-formulation process. For example, in some embodiments, two different formulations are introduced (e.g., injected) into the SCS. One of the formulations is the "drug formulation" (used interchangeably herein with "particle formulation," "drug particle formulation." "active agent," "active agent formulation," and the like) and the other is the "pushing formulation" (referred to herein in some embodiments, as the "hydrogel formulation." "hydrogel pushing formulation." or the like). The drug formulation contains whatever materials are to be delivered to specific locations(s) in the SCS in a suitable carrier fluid (e.g., water) and containing suitable excipients (if needed). The pushing formulation may also contain the same or different materials to be delivered to specific locations(s) in the SCS, or may contain no such materials.

Figure 2B:
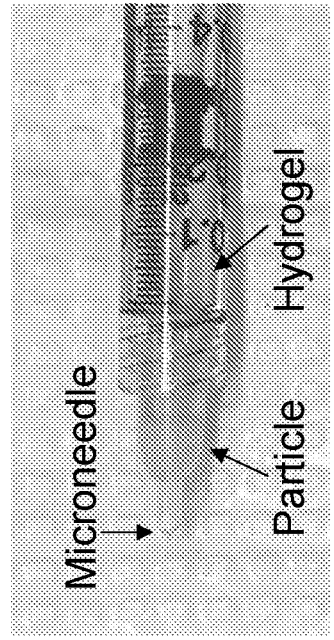
FIG. 2B is a photographic image of a microneedle with a syringe containing a particle formulation and a hydrogel formulation.
Figure 2A:
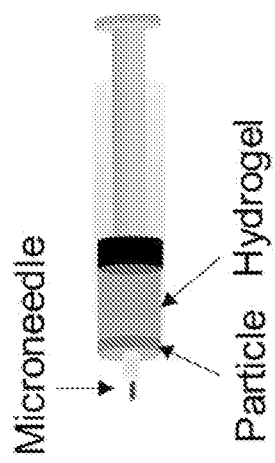
FIG. 2A is a schematic diagram of a microneedle with a syringe containing a particle formulation and a hydrogel formulation.

The drug and pushing formulations are introduced into the SCS substantially at the same time or are introduced into the SCS separately. For example, in some embodiments, the drug formulation and the pushing formulation are both loaded into the same microneedle device or microneedle coupled to a syringe. For example, formulations loaded into a microneedle coupled to a syringe are shown in schematically in FIG. 2A and by photograph in FIG. 2B. The "particle" in FIGS. 2A and 2B refers to a drug formulation that comprises a drug particle. In some embodiments, the drug particle formulation is located proximal to the needle portion of the microneedle and between the needle portion of the microneedle and the hydrogel formulation as shown in FIGS. 2A and 2B.

Through a single pressing of the syringe, the drug formulation can be injected into the SCS, with the pushing formulation following immediately behind (i.e., into the SCS). In some embodiments, the drug and pushing formulations are in the opposite order (i.e., drug formulation toward the plunger end). Thus, in some embodiments, the pushing formulation is administered to the SCS first and the drug formulation follows. In such embodiments, the drug formulation may be pushed anteriorly rather than posteriorly. In some embodiments, there are multiple regions within the syringe containing drug or pushing formulations. In some embodiments, the drug and pushing formulations could be introduced at substantially different times using the same or multiple syringes.

Once injected into the SCS, the drug and pushing formulations will occupy substantially different regions of the SCS. In some embodiments, over time, the pushing formulation expands in volume, which pushes at least a portion of the drug formulation to a different region of the SCS. This expansion in volume and further pushing is referred to herein as "spreading," "hydrogel spreading." "hydrogel swelling." "pushing formulation spreading," "pushing formulation swelling," and the like. The pushing formulation may push the drug formulation toward specific targeted region(s) of the eye (e.g., to promote desired effects) and/or away from specific targeted region(s) of the eye (e.g., to prevent undesired effects). The timescale of pushing and/or spreading can substantially occur within minutes, hours, days, weeks, or longer, depending on the formulations used. In some embodiments, the pushing formulation continues to swell and push the first formulation toward the posterior segment for at least 1 hour, at least 2 hours, at least 3 hours, at least 4 hours, at least 5 hours, at least 6 hours, at least 7 hours, at least 8 hours, at least 9 hours, at least 10 hours, at least 18 hours, at least 24 hours, or more. In some embodiments, the first formulation, following swelling, remains to the further posterior position for at least 1 day, at least 2, days, at least 3 days, at least 4 days, at least 5 days, at least 6 days, at least 7 days, at least 10 days, at least 2 weeks at least 3 weeks, at least 4 weeks, or longer after injection. In some embodiments, the swelling of the pushing formulation occurs as the formulation expands due to uptake of water from the eye tissue. In some embodiments, the swelling of the pushing formulation is further enhanced when the pushing formulation comprises a salt to drive osmotic flow into the formulation.

Figure 3:
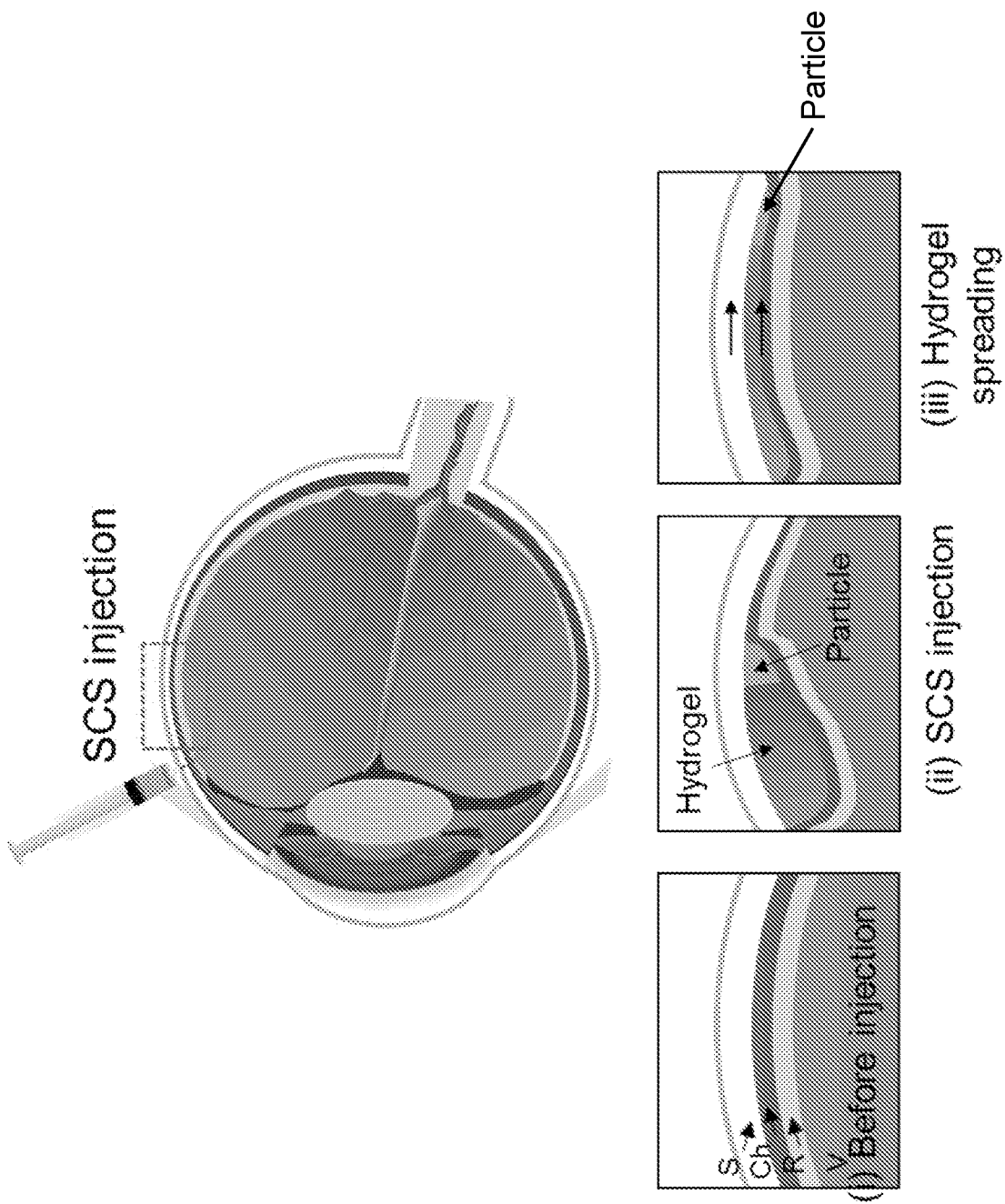
FIG. 3 is a schematic diagram of the SCS injection of a hydrogel pushing formulation and its effects within the suprachoroidal space. Before injection (box (i)), the SCS is the potential space between the sclera (S) and the choroid (Ch). The retina (R) is located between the choroid and the vitreous (V). Box (ii) shows the suprachoroidal space after SCS injection of a particle formulation followed by a hydrogel pushing formulation. Box (iii) shows the suprachoroidal space after the hydrogel pushing formulation has caused spreading through the SCS, pushing the particle formulation toward the posterior segment of the eye.

FIG. 3 schematically shows the concept of the hydrogel pushing method before injection, during and after SCS injection, and the effect of the hydrogel spreading after injection. The formulation infuses into the SCS, where the drug particle is first injected. After injection into the SCS, the hydrogel swells, or pushes drug further toward the back of the eye, as shown in FIG. 3.

The drug and pushing formulations are designed according to a number of criteria. For example, in some embodiments, the formulations are biocompatible with the eye and satisfy other safety concerns. In some embodiments, the formulations are compatible with the active agents or drugs they deliver to the eye. In some embodiments, the formulations have a viscosity (e.g., dynamic viscosity) during injection low enough that allows them to flow into the SCS. In some embodiments, the viscosity is low enough to allow flow within the SCS during the pushing. In certain embodiments, the drug and pushing formulations do not substantially mix with each other. In one aspect, the goal of the hydrogel pushing procedure is for a separate pushing formulation to push the separate drug formulation and not have them substantially mix before or during the pushing. However, some mixing is acceptable, as long as the pushing formulation pushes at least a portion of the drug formulation to a different region of the SCS. The separation of the drug and pushing formulations can be due to thermodynamic and/or kinetic reasons. Thermodynamic reasons include the use of formulations that are at least substantially immiscible through use, for example, of different solvents/carrier fluids. Kinetic reasons include high viscosity that slows the mixing of the formulations.

In one aspect, the drug formulation has a lower viscosity than the pushing formulation during injection into the SCS and/or during the pushing within the SCS. This enables the pushing formulation to apply a force to the drug formulation while reducing the mixing of the two formulations. Pushing is achieved by swelling the pushing formulation. Swelling can be achieved by a number of different mechanisms and possibly triggered by a number of different mechanisms. The pushing formulation can form a gel that expands due to, for example and without limitation, physicochemical cues, such as change in pH, change in temperature, change in divalent cation concentration and other triggers of gel swell.

In some embodiments, the formulation can undergo a phase change, for example from liquid to gas, for example caused by a temperature change. In some embodiments, the pushing formulation can expand due to influx of other materials into the formulation, such as water from the surrounding tissues and/or the drug formulation. This could be accomplished by osmotic forces caused by higher solute content in the pushing formulation compared to surrounding fluids. In some embodiments, the formulations in a single syringe can comprise a drug particle phase and a swellable pushing hydrogel phase. The formulations to be injected in a single syringe can be a single or multiple formulations.

In some embodiments, the drug formulation can contain drugs, molecules, particles, hydrogels, polymers, diagnostics, therapeutics and other agents (materials). In some embodiments, the drug particle phase can have a positive or a negative charge, or no charge, and if zwitterionic, a net positive charge, net negative charge or no net charge without modifications.

In some embodiments, the pushing formulation can contain drugs, molecules, particles, hydrogels, polymers, diagnostics, therapeutics and other agents (materials) and it can have any charges or no charge, and if zwitterionic, a net positive charge, net negative charge or no net charge. In some embodiments, the pushing formulation comprises swellable or non-swellable materials. In some embodiments, the pushing formulation comprises or is a gel or an oil, such as silicone oil. In certain embodiments, the pushing formulation has a higher density relative to the drug formulation. In some embodiments, the drug formulation and pushing formulation are a single formulation having the drug or other material for delivery to the desired ocular tissue and having one or more characteristics that allow hydrogel pushing and/or swelling to push the entire formulation toward the posterior segment of the eye after injection.

In some embodiments, the drug formulation comprises particles. The particles of the drug formulations provided herein may be drug, or may be particles that contain drug. In some embodiments, the active agent or drug has a charge. In some embodiments, the active agent or drug has a positive charge or a negative charge. In some embodiments, the active agent or drug is within or associated with particles that have a charge. In some embodiments, the particles have a positive charge or a negative charge. In one embodiment, the drug formulation includes microparticles or nanoparticles, either of which includes at least one drug. Desirably, the microparticles or nanoparticles provide for the controlled release of drug into the suprachoroidal space and surrounding posterior ocular tissue. As used herein, the term "microparticle" encompasses microspheres, microcapsules, microparticles, and beads, having a number average diameter of from about 1 μm to about 100 μm, for example from about 1 to about 25 μm, or from about 1 μm to about 7 μm. "Nanoparticles" are particles having an average diameter of from about 1 nm to about 1000 nm. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 1000 nm or less. In one embodiment, the drug formulation comprises microparticles having a $D_{99}$ of about 10 μm or less. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 1000 nm or less. In one embodiment, the drug formulation comprises microparticles having a $D_{99}$ of about 10 μm or less. The microparticles, in one embodiment, have a $D_{50}$ of about 3 μm or less. In a further embodiment, the $D_{50}$ is about 2 μm. In another embodiment, the $D_{50}$ of the particles in the drug formulation is about 2 μm or less. In another embodiment, the $D_{50}$ of the particles in the drug formulation is about 100 nm to about 1000 nm. In one embodiment, the drug formulation comprises microparticles having a $D_{99}$ of about 1000 nm to about 10 μm. The microparticles, in one embodiment, have a $D_{50}$ of about 1 μm to about 5 μm or less. In another embodiment, the drug formulation comprises particles having a $D_{99}$ of about 10 μm. In another embodiment, the $D_{99}$ of the particles in the formulation is less than about 10 μm, or less than about 9 μm, or less than about 7 μm or less than about 3 μm. The microparticles or nanoparticles, in some embodiments, have a charge, such as a negative charge.

Microparticles and nanoparticles may or may not be spherical in shape. "Microcapsules" and "nanocapsules" are defined as microparticles and nanoparticles having an outer shell surrounding a core of another material. The core can be liquid, gel, solid, gas, or a combination thereof. In one case, the microcapsule or nanocapsule may be a "microbubble" or "nanobubble" having an outer shell surrounding a core of gas, wherein the drug is disposed on the surface of the outer shell, in the outer shell itself, or in the core. (Microbubbles and nanobubles may be respond to acoustic vibrations as known in the art for diagnosis or to burst the microbubble to release its payload at/into a select ocular tissue site.) "Microspheres" and "nanospheres" can be solid spheres, can be porous and include a sponge-like or honeycomb structure formed by pores or voids in a matrix material or shell, or can include multiple discrete voids in a matrix material or shell. The microparticles or nanoparticles may further include a matrix material. The shell or matrix material may be a polymer, amino acid, saccharride, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In some embodiments, the pushing formulation comprises hyaluronic acid (HA). In some embodiments, both the drug formulation and the pushing formulation comprise HA. In some embodiments, the pushing formulation comprises a higher % (w/v) HA than the drug formulation. In some embodiments, the drug formulation comprises 0% (w/v), about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 2.5% (w/v), about 3.0% (w/v), about 3.5% (w/v), about 4.0% (w/v), about 4.5% (w/v), about 5.0% (w/v) HA or more. In some embodiments, the pushing formulation comprises about 1% (w/v), about 1.5% (w/v), about 2% (w/v), about 2.5% (w/v), about 3% (w/v), about 3.1% (w/v), about 3.2% (w/v), about 3.3% (w/v), about 3.4% (w/v), about 3.5% (w/v), about 3.6% (w/v), about 3.7% (w/v), about 3.8% (w/v), about 3.9% (w/v), about 4.0% (w/v), about 4.1% (w/v), about 4.2% (w/v), about 4.3% (w/v), about 4.4% (w/v), about 4.5% (w/v), about 4.6% (w/v), about 4.7% (w/v), about 4.8% (w/v), about 4.9% (w/v), about 5.0% (w/v), about 5.5% (w/v), about 6.0% (w/v), about 6.5% (w/v), about 7.0% (w/v), about 7.5% (w/v), about 8.0% (w/v), about 8.5% (w/v), about 9.0% (w/v), about 10% (w/v), or more HA. In some embodiments, the drug formulation comprises about 0.1% (w/v) to about 2.5% (w/v) HA and the pushing formulation comprises about 2.5% (w/v) to about 5% (w/v) HA. In some embodiments, the drug formulation comprises about 0.5% (w/v) to about 1.5% (w/v) HA and the pushing formulation comprises about 3.0% (w/v) to about 5% (w/v) HA. In some embodiments, the drug formulation comprises about 1% (w/v) HA and the pushing formulation comprises about 4% (w/v) HA.

In some embodiments, one or more of the formulations comprises a salt. For example, in some embodiments, one or more of the formulations (e.g., the drug formulation or the pushing formulation) comprises a salt selected from the group consisting of NaCl, MgCl, MnCl$_2$, CaCl$_2$), ZnCl$_2$, and KCl. In some embodiments, the pushing formulation is a high-salt formulation. In some embodiments, the pushing formulation comprises about 5%, about 6%, about 7%, about 8%, about 9%, about 10%, about 11%, about 12%, about 13%, about 14%, or about 15% NaCl, or any other salt known in the art. For example, in some embodiments, the pushing formulation comprises about 9% NaCl. In some embodiments, increasing the salt concentration of the pushing formulation results in a pushing formulation that exhibits enhanced, increased, and/or more rapid pushing of the drug formulation further posteriorly in the posterior segment of the eye.

In some embodiments, the total volume injected into the suprachoroidal space of the eye (inclusive of drug formulation and pushing formulation) is about 10 µL, about 20 µL, about 30 µL, about 40 µL, about 50 µL, about 60 µL, about 70 µL, about 80 µL, about 90 µL, about 100 µL, about 110 µL, about 125 µL, about 150 µL, about 175 µL, about 200 µL, about 225 µL, about 250 µL, about 300 µL, about 400 µL, or about 500 µL. In some embodiments, the drug formulation is present at an equal, a higher, or a lower amount relative to the pushing formulation. For example, in some embodiments, the total injection volume is 50 µL, the volume of the drug formulation 20 µL, and the volume of the pushing formulation 30 µL.

In some embodiments, the order of the formulations in a single syringe can be altered depending on the objective. For example, the drug particle formulation may be closer to the microneedle end and the pushing formulation may be distal to the microneedle end. In some embodiments, the drug particle formulation can be delivered to a greater extent toward anterior or posterior area depending on the sort and order of the formulations in a single syringe. This procedure can be conducted on any eye that contains, or can be made to contain, a suprachoroidal space, including human and animal eyes for medical, veterinary and other applications.

Iontophoresis

In one aspect, the present disclosure provides methods for targeted delivery to tissues within the eye of a subject in need thereof, comprising SCS injection and iontophoresis application. In some embodiments, for delivery in the SCS using iontophoresis, a two-step process is provided. In the first step, a drug formulation is introduced (e.g., injected) into the SCS. The drug formulation contains whatever materials are to be delivered to specific locations(s) in the SCS in a suitable carrier fluid (e.g., water) and containing suitable excipients (if needed). In the second step, an electric field is applied such that charged species move within the SCS by iontophoresis. "Iontophoresis" herein includes electrophoresis, electoosmosis, electrically enhanced diffusion and other electrokinetic phenomena.

In some embodiments, the drug formulation is be injected and iontophoresis applied into the SCS substantially at the same time. In other embodiments, the drug formulation is injected and iontophoresis is applied separately or concurrently. For example, if introduced at substantially the same time, the drug formulation in some embodiments is injected into the SCS and iontophoresis is applied before, during and/or after the injection. If introduced at substantially different times, the drug formulation could be injected in the absence of iontophoresis, and iontophoresis could be applied after the injection is finished.

In one aspect, using this approach, the region(s) of the SCS occupied by the drug formulation targeted using iontophoresis is different from that which would have been occupied if the same procedure had been followed but without using iontophoresis. If the iontophoresis is applied after the drug formulation is injected, then the drug formulation will occupy a different region of the SCS after the application of iontophoresis compared to before iontophoresis. A "different region" means that at least a portion of the drug formulation occupies a region of the eye that is different from the comparator region (e.g., without or before iontophoresis). The timescale of iontophoresis application can occur for seconds, minutes or possibly hours, depending on the conditions used and the objectives of the procedure.

In some embodiments, the drug formulation for use in the iontophoresis method contains materials to be delivered to specific locations(s) in the SCS. Materials may be charged (positively and/or negatively) with a net charge or a net neutral charge (e.g., zwitterionic) and/or they may be uncharged. Materials may be contained within carrier materials such as particles like nanoparticles, microparticles, liposomes, micelles, colloids and other structures. The carrier materials (used interchangeably herein with "containing materials") may be charged (positively and/or negatively) with a net charge or a net neutral charge (e.g., zwitterionic) and/or they may be uncharged. The charge on the materials and the charge on the carrier materials influence the movement of the drug formulation in the SCS during iontophoresis. For example, if the net charge on the materials or on the carrier materials is negative, then the materials and the carrier materials will be moved away from the negative electrode and toward the positive electrode. As another example, if the net charge on the material or on the carrier materials is positive, then the materials and the carrier materials will be moved away from the positive electrode and toward the negative electrode. If there is no charge or no net charge on the material or on the carrier materials, then the materials and the carrier materials can be moved by electroosmosis. Electrically enhanced diffusion can be achieved, for example, by applying an alternating the electric field and/or alternating the current.

In one aspect, iontophoresis is applied by using at least two electrodes that are capable of generating an electric field within the SCS. For example, an electrode can be associated with the syringe used to inject the drug formulation. An electrode could be the needle, or part of the needle or attached to the needle used to inject the drug formulation. An electrode could be located within the barrel of the syringe, attached to the inner wall of the syringe, the plunger or another part of the syringe. In some embodiments, the electrode is located within the syringe, for example on the end of the plunger, and the wire is passed through the rubber stopper of the syringe. In some embodiments, an electrode is physically separate from the syringe and/or needle used for injection of the drug formulation. In some embodiments, there is an electrically conductive pathway from an electrode to the needle and/or syringe and/or through the needle and/or syringe. In some embodiments, there is a conductive pathway from an electrode to at least a portion of the SCS. In some embodiments, there is a conductive pathway from an electrode to and through the site of injection of materials into the SCS. Typically an electrode associated with the injection site would have a polarity (i.e., negative or positive electrode) that repels the materials and/or carrier materials, but not necessarily, depending on the location to which the materials are being targeted.

In some embodiments, an electrode is located distant from the injection site. In some embodiments, an electrode located distant from the injection site has a polarity (i.e., negative or positive electrode) that attracts the materials and/or carrier materials. In some embodiments, the distant location would typically be somewhere on the head or neck, possibly the ear or forehead or other skin surface on the head or neck. The distant location could be within the head, such as within the mouth or nose. The skin could be prepared with an conductive gel, by sandpapering the skin or other methods known in the art to facilitate good electrical contact between an electrode and skin and to reduce the electrical resistance of the skin.

In some embodiments, a conductive material is applied at a site of an electrode to facilitate passage of current and/or heat transfer. For example, in some embodiments, an electrically conductive material is used to increase the effective contact area of an electrode with the skin, eye or other tissue it contacts to reduce the current density for a given current. For example, a thermally conductive material is used to facilitate heat transfer away from an electrode and/or contact area with the skin, eye or other tissue it contacts to reduce heating at those sites.

Without an iontophoresis application, the materials injected using a microneedle localize in the suprachoroidal space, with precise location depending on the material, the formulation, the injection procedure and other parameters. The distribution of the injected materials can be changed with application of an iontophoresis. For example, in some embodiments, the injected material can be delivered to a greater extent toward one or the other of the electrodes, depending on the charge of the material, the electrode polarity and other factors (e.g., positively charged materials will move away from the positive electrode and toward the negative electrode). Movement caused by the current can be by electrophoresis, electroosmosis, electromigration, iontophoresis or other phenomena that move charged and/or uncharged materials due to an electric field or current. In this manner, precise targeting to specific tissues and areas can be achieved.

In one aspect, the electric field or current is applied by controlling the voltage, controlling the current, or both. In some embodiments, a constant voltage is maintained. In some embodiments, a constant current is maintained. In other embodiments, the voltage and/or current is changed over time.

The electric field and/or current is selected by balancing multiple parameters including sufficient force to move materials to a desired location(s), and preferably not to cause damage, pain, side effects or other adverse effects to the eye, the body, or the operator. In some embodiments, the iontophoresis is applied using a current having an absolute value of about 0.01 mA, about 0.05 mA, about 0.10 mA, about 0.15 mA, about 0.2 mA, about 0.3 mA, about 0.4 mA, about 0.5 mA, about 0.6 mA, about 0.7 mA, about 0.8 mA, about 0.9 mA, or about 1.0 mA. The polarity of the current is selected depending on the net charge of the drug or particles and the location to which the drug or particles is to be targeted (e.g., anteriorly or posteriorly to the injection site) as described herein. In some embodiments, the iontophoresis is applied using a positive current of about 0.01 mA, about 0.05 mA, about 0.10 mA, about 0.15 mA, about 0.2 mA, about 0.3 mA, about 0.4 mA, about 0.5 mA, about 0.6 mA, about 0.7 mA, about 0.8 mA, about 0.9 mA, or about 1.0 mA, and the method is performed using particles or active agent having a net negative charge. In other embodiments, the iontophoresis is applied using a negative current of about 0.01 mA, about 0.05 mA, about 0.10 mA, about 0.15 mA, about 0.2 mA, about 0.3 mA, about 0.4 mA, about 0.5 mA, about 0.6 mA, about 0.7 mA, about 0.8 mA, about 0.9 mA, or about 1.0 mA, and the method is performed using particles or active agent having a net negative charge. In still other embodiments, the polarity of the current and the drug or particles is the same.

In one aspect, the iontophoresis methods provided herein can be conducted on any eye that contains, or can be made to contain, a suprachoroidal space, including human and animal eyes for medical, veterinary and other applications.

In some embodiments, the electrodes are designed to minimize pH changes during application of the electric field and/or current, because pH changes can damage tissue, can alter the charge on materials and tissue and can have other effects that influence safety and efficacy of the procedure. In some embodiments, an electrode can be associated with a needle and/or syringe. In one embodiment, the needle itself can be an electrode (e.g., an electrically conductive needle). In another embodiment, the electrode can be placed in the interior of the syringe, for example in fluid and/or electrical communication with the contents of the syringe. The electrode can be attached to the plunger in the syringe or to the side-wall of the syringe. In one embodiment, the electrode can be placed around the microneedle so that the electrode can attach on the eye tissues or not eye tissues in the electric communication via the microneedle or eye tissues or the injection hole.

An electrode can be in electrical communication with a tissue of the eye and/or a tissue not part of the eye. In some embodiments, the electrode is in electrical communication with a surface of the eye, such as the cornea, or conjunctiva, or sclera, or in the periocular space. In some embodiments, the electrode is in electrical communication with a surface not of the eye, such as the skin or the oral mucosa. For example, the skin could be on the head, the face, the ear (e.g., the ear lobe), the nose, the forehead, or the temple. In some embodiments, the site of electrical communication with an electrode could be treated to facilitate good electrical contact with the body, such as by application of electrically conductive gel and abrasion of the site (e.g., abrasion with sandpaper). In one aspect, the present disclosure provides a kit for targeted delivery of a substance to a region of the eye, wherein the kit comprises the electrodes, microneedles, and syringes provided herein.

Combined Hydrogel Pushing and Iontophoresis

In one aspect, the present disclosure provides compositions, systems, methods, devices, and kits for drug administration to targeted portions of the eye using a combination of hydrogel pushing and iontophoresis. Precise delivery to target tissues and areas can be modulated by using SCS injection and a combination of both the hydrogel pushing and iontophoresis approaches described herein. The various events—injection of drug formulation, injection of pushing formulation, application of iontophoresis—can be done all at the same time, two at the same time or none at the same time. For example, in some embodiments, the drug formulation and pushing formulation are performed concurrently or sequentially, and iontophoresis is applied following the injection of the drug and pushing formulations. In other embodiments, the iontophoresis may be applied before or during injection of the drug and/or pushing formulations. In such embodiments, the drug formulation may be be pushed by the pushing formulation and the iontophoresis application further posteriorly in the eye. In still other embodiments, the pushing formulation may be administered first, followed by concurrent or sequential administration of the drug formulation and iontophoresis application. In certain embodiments, a drug formulation is administered by SCS injection using a microneedle, iontophoresis is applied after injection of the drug formulation, and a pushing formulation is injected into the SCS using a microneedle after application of iontophoresis.

The present invention is further illustrated by reference to the following Examples. However, it should be noted that these Examples, like the embodiments described above, are illustrative and are not to be construed as restricting the scope of the invention in any way.

EXAMPLES

Example 1. Targeted Suprachoroidal Space Drug Delivery Using Hyaluronic Acid Hydrogel Pushing A study was conducted to assess the targeting of drug delivery by hydrogel pushing in conjunction with injection into the suprachoroidal space of the eye and to study the effects of varied formulation characteristics in the methods provided herein. Drug particle formulations comprising red fluorescent particles and 0%, 1%, 2%, or 4% HA were prepared. The drug particle formulations at a volume of 20 µL were loaded into a microneedle with a 4% HA pushing formulation at a volume of 30 µL, and the formulations were infused into the SCS of rabbit eyes ex vivo. Immediately after injection of the formulations, the ex vivo eye was frozen and dissected to assess the extent to which the various formulations pushed to the posterior pole of the eye.

FIG. 4A shows the distributions of the red-fluorescent particles after SCS injection of each of the 4 formulations. The figure shows the percent of particles distributed to the increasingly distant regions as indicated (0-3 mm, 3-6 mm, 6-9 mm, or 9 mm or more). The averaged particle transfer (APT) for each group is also shown at the top of the bars for each of the groups in FIG. 4A. The 0% HA drug particle formulation had an APT of 3.8+0.3 mm: the 1% HA drug particle formulation had an APT of 4.0+0.4 mm: the 2% HA drug particle formulation had an APT of 3.3+0.2 mm: and the 4% HA drug particle formulation had an APT of 2.3+0.2 mm. Accordingly, decreasing concentrations of HA resulted in less pushing of the particle formulation to the posterior pole, but some amount of HA present in the drug particle formulation was required for optimal results. The study showed that the particle formulation requires a small amount of viscosity to be optimally pushed by the pushing formulation. In summary, the formulation with 1% was chosen as the drug particle solution for further studies.

FIG. 4B shows the particle distribution (% of particles located at the indicated positions) when the drug particle formulation was held at 1% HA and the pushing formulation was tested at 2%, 4%, or 8% HA. The pushing effect was improved with 4% or 8% HA relative to 2% HA. The APT for 2% HA in the pushing formulation was 3.8+0.4 mm: the APT for 4% HA in the pushing formulation was 4.0+0.4 mm; and the APT for 8% HA in the pushing formulation was 4.3+0.5 mm. The 8% HA formulation exhibited many bubbles due to the high viscosity. Accordingly 4% HA was selected as the concentration for the pushing formulation for further studies.

FIG. 4C shows a digital (i) and fluorescent (ii) image following injection of the formulation comprising 1% HA in the drug particle formulation and 4% HA in the pushing formulation ("1%/4% formulation"). The red fluorescent particles in the drug formulation was pushed backward from the injection site to the posterior pole.

Figure 5:
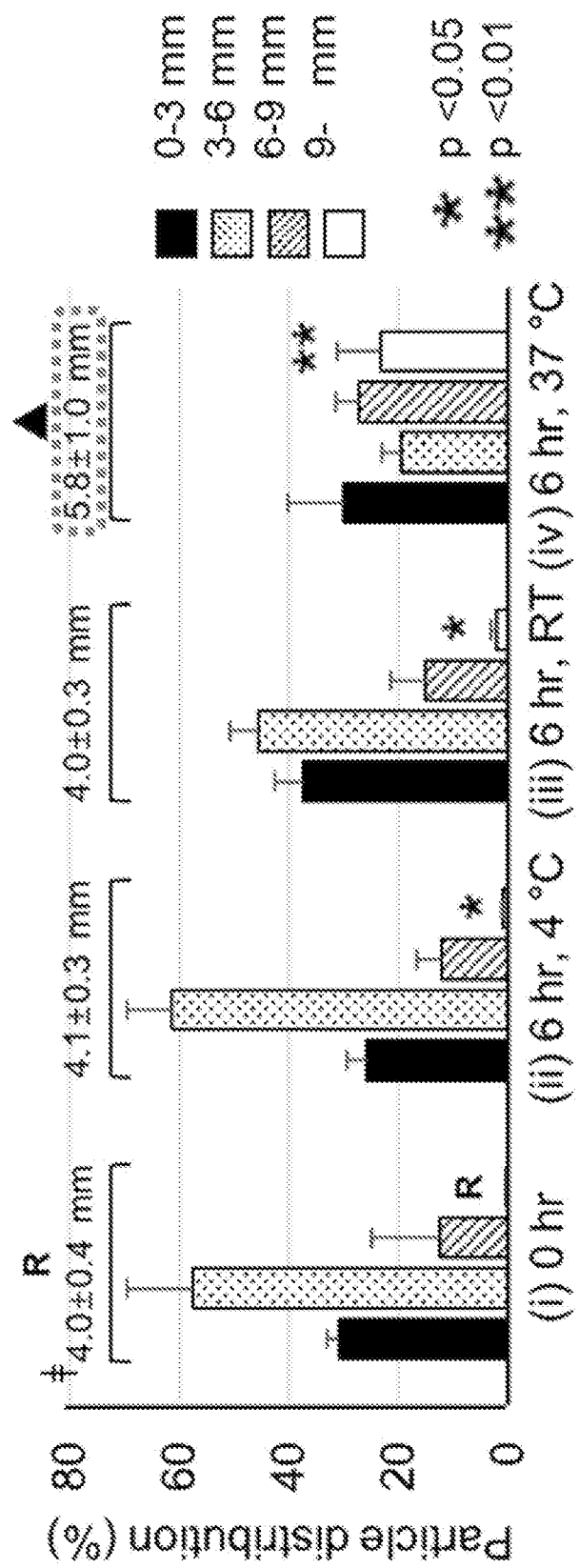
FIG. 5 shows the particle distribution (%) at each region in the eye following SCS injection of the 1%/4% formulation and incubation and no incubation ((i), 0 hr), for 6 hours at 4° C. (ii), for 6 hours at room temperature (iii), or for 6 hours at 37° C. (iv). The averaged particle transfer (APT) is also shown in mm at the top of the bars in the graph for each group. R is reference value. ▼ Significance (One-way ANOVA) between the APT of the reference (R) and the APT of the other formulations. * ** Significance (One-way ANOVA) between the 9—mm distribution of the reference (R) and other formulations. The graphs show the average ±standard deviation based on 3 replicate samples (avg±SD, n=3).
Figure 6:
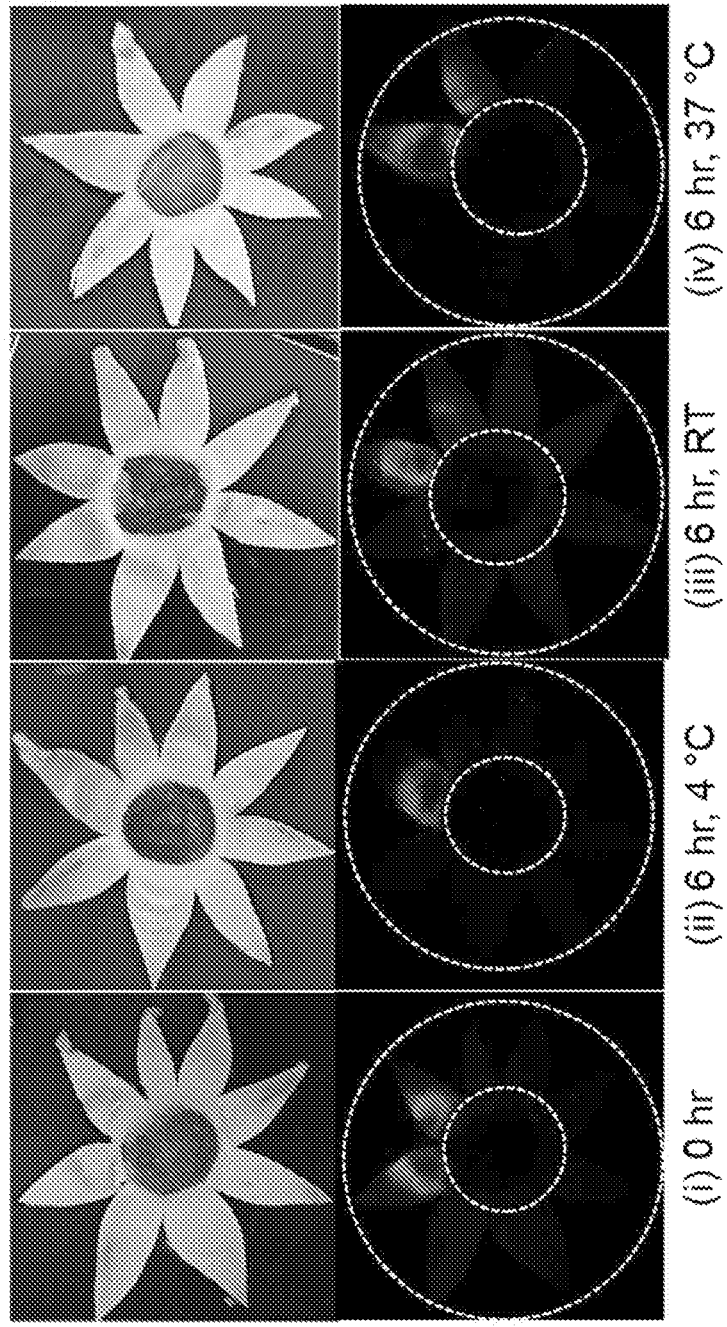
FIG. 6 shows the bright field (top row) and fluorescent (bottom row) images of ex vivo rabbit eyes after SCS injection of the 1%/4% formulation and no incubation (1$^{st}$ column), for 6 hours at 4° C.(2$^{nd}$ column), for 6 hours at room temperature (RT: 3$^{rd}$ column), or for 6 hours at 37° C. (4th column).

Next, the effects of incubation at different temperatures on the particle delivery toward the back of the eye was assessed. The 1%/4% formulation was injected in a 50 µL volume into the SCS of rabbit eyes ex vivo and eyes were incubated for 0 hr, 6 hrs at 4° C., 6 hrs at room temperature (RT), or 6 hrs at 37° C. Distributions of the red fluorescent particles in the SCS in each condition are shown in FIG. 5. Particle distribution was similar in the 0 hr (i) and 4° C. (ii) groups. At RT (iii), a small amount of the particles were moved to the back of the eye. When the incubation temperature was 37° C. (iv), the drug particle was localized around the optic nerve. The APT for the 0 hour incubation (i) was 4.0+0.4 mm: the APT for the incubation at 4° C., was 4.1±0).3 mm; the APT for the incubation at RT was 4.0+0.3 mm; and the APT for the incubation at 37° C., was 5.8+1.0 mm. FIG. 6 shows the bright field (top row) and fluorescent (bottom row) images of the rabbit eyes ex vivo with each of the incubation conditions. The particles were transferred to the back of the eye in the 6 hour, 37° C. incubation group.

The study showed that using the 1%/4% formulation, 14.1±5.4% of the particles was delivered toward the back of the eye (i.e., >6 mm posterior to the limbus) right after injection: and 54.3±10.2% of particles were delivered >6 mm posterior to the limbus after 6 h at 37° C. This demonstrated the ability of the pushing formulation to move more than half of the particles to the back part of the SCS. This pushing was facilitated not only by the increase in hydrogel volume upon contact with water in the eye, but also because the viscosity of the HA pushing hydrogel was decreased at 37° C.(relative to room temperature at which it was injected).

Figure 7A:
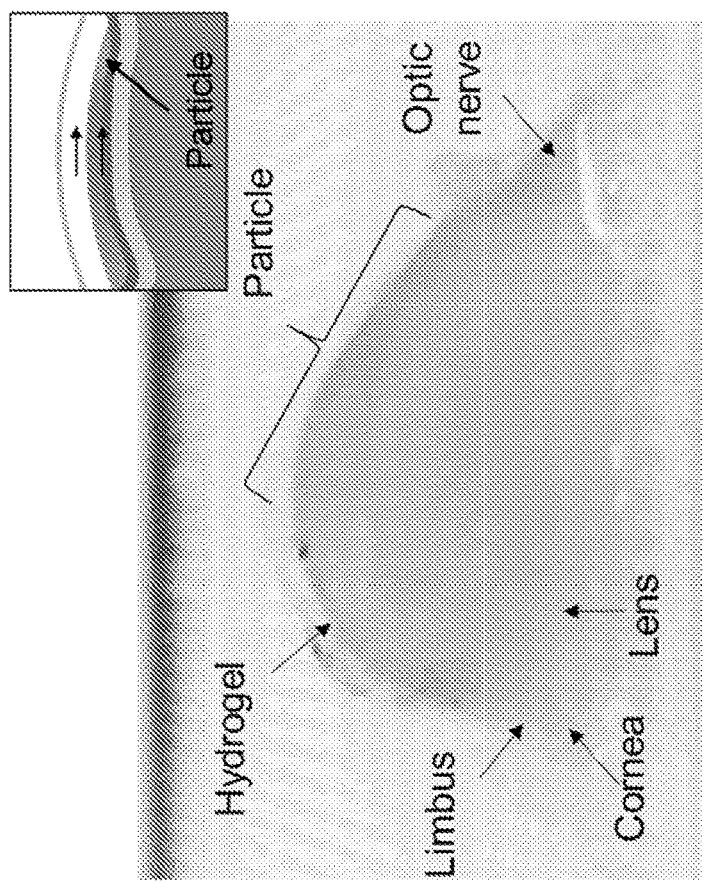
FIG. 7A shows a digital image of a dissected eye right after the injection of the 1%/4% formulation.
Figure 7B:
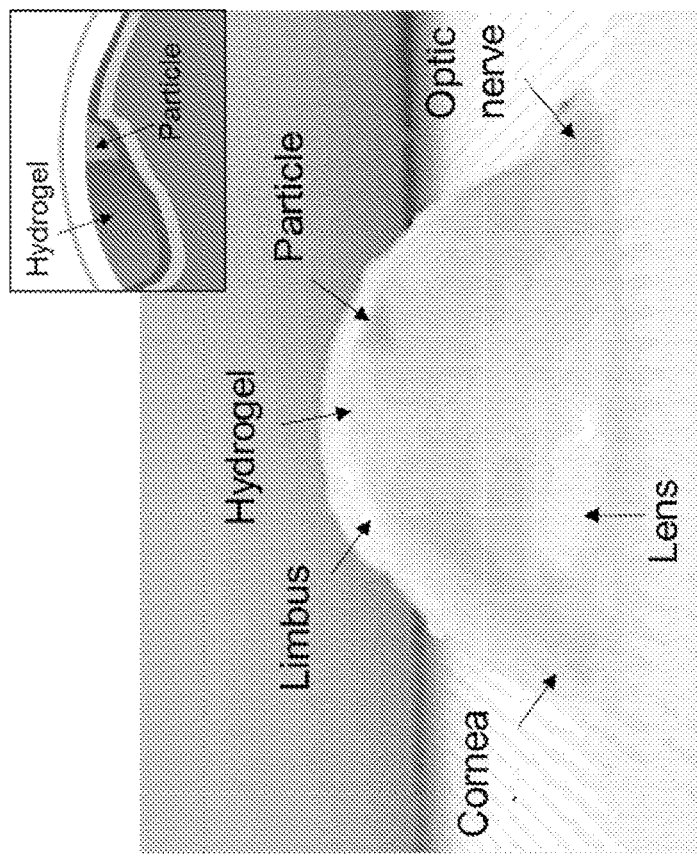
FIG. 7B shows a digital image of a dissected eye after a 6 hour incubation at 37° C., following the injection.

FIG. 7A shows a digital image of a dissected eye right after the injection of the 1%/4% formulation. The drug particle was localized at the end of the SCS by the pushing hydrogel. FIG. 7B shows a digital image of a dissected eye after a 6 hour incubation at 37° C. following the injection. The image shows that after the incubation, the particle was delivered around the optic nerve by the spreading of the hydrogel.

To further assess the effects of the pushing formulation, a study was conducted to observe the effect of injecting various drug particle formulations without a pushing formulation included. FIG. 8A shows the particle distribution (bar graph) and bright field and fluorescent images immediately following SCS injection of 50 μL of red fluorescent particles in HBSS buffer (no HA). This injection achieved only 7.1±1.1% of particles reaching around the back of the eye (9—mm from limbus). FIG. 8B shows the particle distribution (bar graph) and bright field and fluorescent images immediately following SCS injection of 20 μL of particle in 1% HA. FIG. 8C shows the particle distribution (bar graph) and bright field and fluorescent images following SCS injection of 20 μL of particle in 1% HA, after a 6 hour incubation at 37° C. Distributions of the 1% HA and the 1% HA with 6 hour incubation at 37° C., were similar, and there was no significant difference among the groups. Thus, the study showed that without the presence of the pushing formulation, there is no spreading of the drug particle formulation.

Figure 9A:
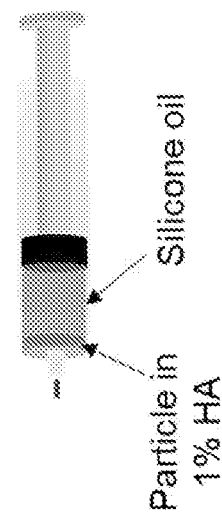
FIG. 9A is a schematic showing the 1% HA drug particle formulation and silicone oil in a microneedle.
Figure 9B:
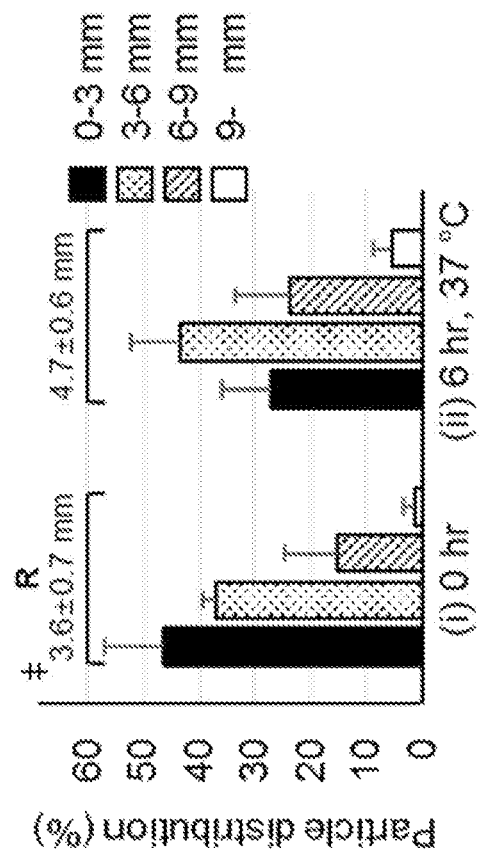
FIG. 9B shows the percent particle distribution at the indicated positions immediately after the injection (0 hr), or after a 6 hour incubation at 37° C., following the injection, using the silicone oil as the pushing formulation. The APT in the 0 hr group was 3.6+0.7 mm. The APT in the 6 hr incubation group was 4.7±0.6 mm.
Figure 9C:
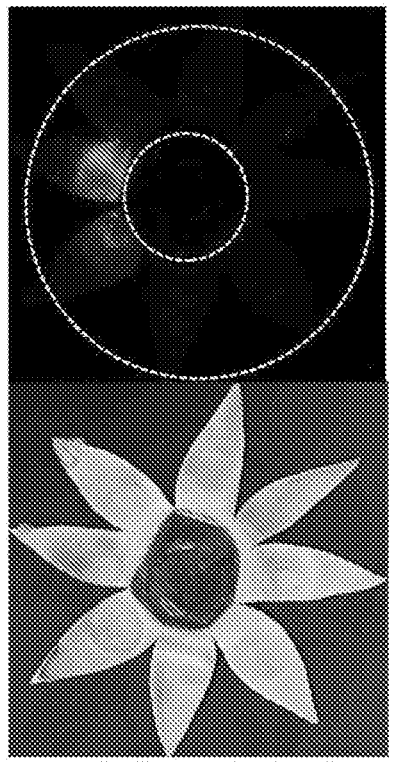
FIG. 9C shows the bright field and fluorescent images for the two groups. R is reference value. No Significance (One-way ANOVA) between the APT of the reference (R) and the APT of the formulations. Graphs (a) present average+standard deviation based on 3 replicate samples (avg±SD, n=3).

A further study was conducted to assess the ability of a silicone oil formulation to perform the pushing function. Silicone oil was used in place of the HA pushing hydrogel. FIG. 9A is a schematic showing the 1% HA drug particle formulation and silicone oil in the microneedle. FIG. 9B shows the percent particle distribution at the indicated positions immediately after the injection (0) hr) or after a 6 hour incubation at 37° C., following the injection. FIG. 9C shows the bright field and fluorescent images for the two groups. The study showed that the silicone oil did not exhibit the effective particle pushing achieved with the HA pushing formulation. Since the silicone oil is immiscible to the drug particle formulation, the drug was not mixed with the silicone oil in the SCS. However, silicone oil did not exhibit the swelling and pushing effect of the particle to back of the eye. Without wishing to be bound by theory, the lower density of the silicone oil relative to the particle solution may inhibit pushing of the particle solution.

Next, analysis of particle delivery toward the back of the eye using a high salt (9% sodium hydrochloride) HA as the pushing formulation was assessed, to determine whether a high salt HA hydrogel can increase osmotic flow of water into the hydrogel, to increase the pushing effect. 9% sodium chloride was added to the 4% HA pushing formulation, loaded into a microneedle with the red fluorescent drug particle formulation. The formulations were injected into the rabbit eyes ex vivo or in vivo.

Figure 10:
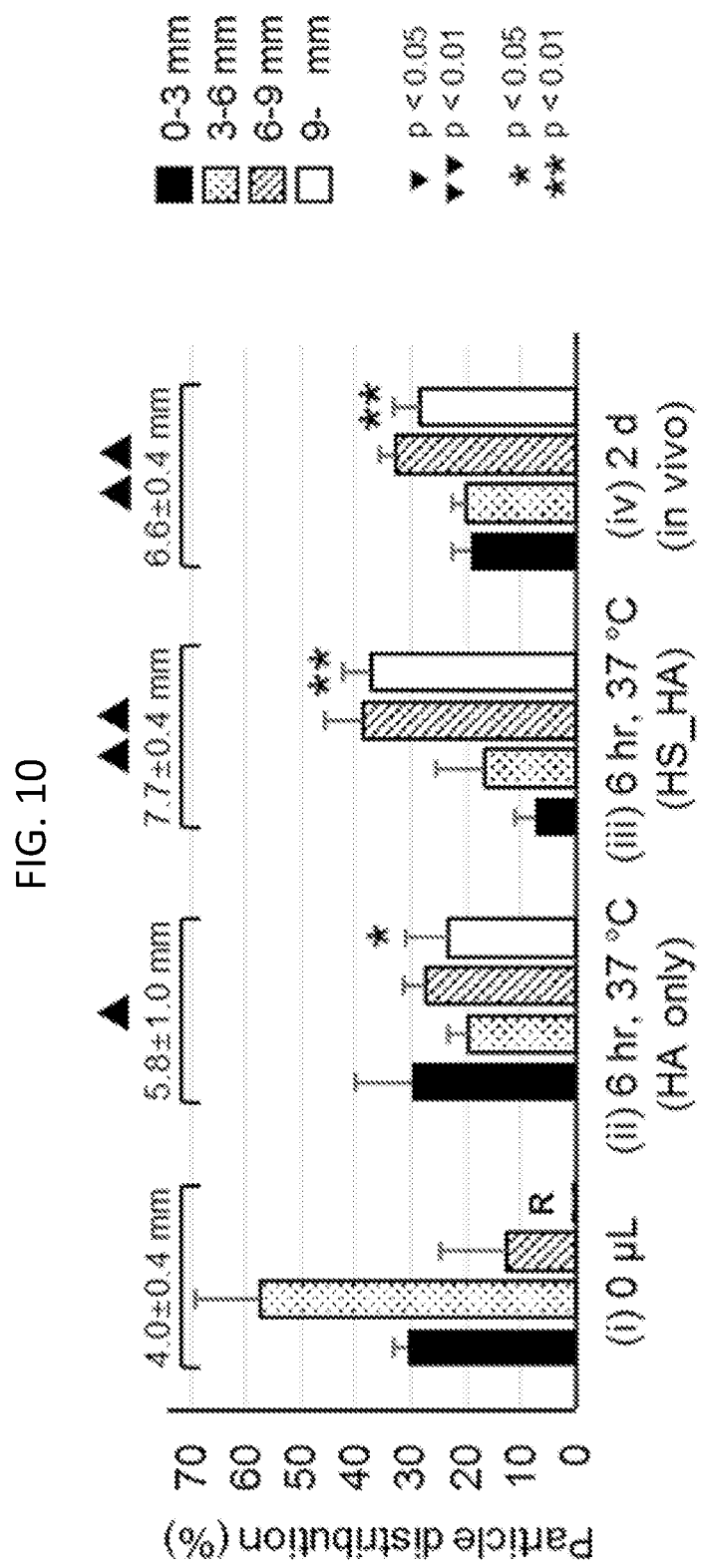
FIG. 10 shows the particle distribution of red fluorescent particles immediately after ex vivo injection (i), after incubation at 37° C. for 6 hours following the ex vivo injection of the HA hydrogel (without added salt) (ii), after incubation at 37° C., for 6 hours following ex vivo injection of the HA hydrogel with 9% sodium chloride added (iii: "HS_HA"), two days after in vivo injection into rabbit eyes using the high-salt (9% sodium chloride) HA formulation. The APT is shown above the bars for each group. R is reference value. ▼, ▼▼ Significance (One-way ANOVA) between the APT of the reference (R) and the APT of the formulations. *** Significance (One-way ANOVA) between the 9—mm distribution of the reference (R) and other formulations. Graphs (a) present average+standard deviation based on 3 replicate samples (aver±SD, n=3).

The results of the study are provided in FIG. 10 an FIG. 11A-11C. FIG. 10 shows the particle distribution of red fluorescent particles immediately after ex vivo injection (i), after incubation at 37° C. for 6 hours following the ex vivo injection of the HA hydrogel (without added salt) (ii), after incubation at 37° C. for 6 hours following ex vivo injection of the HA hydrogel with 9% sodium chloride added (iii: "HS_HA"), two days after in vivo injection into rabbit eyes using the high-salt (9% sodium chloride) HA formulation. The normal HA hydrogel delivered 54.3±10.2% of particles over 6 mm posterior to the limbus, and the APT for the normal HA hydrogel was 5.8+1.0 mm. The high-salt HA hydrogel pushed 80.7±6.1% of the particles >6 mm posterior to the limbus (and 38.0+2.1% of particles were >9 mm posterior to the limbus) 6 hours after injection at 37° C., and the APT for this group was 7.7±0.4 mm. Moreover, the in vivo SCS injection of the rabbit eye showed that 61.2+7.7% of the particle was delivered to over 6 mm posterior to the limbus 2 day after the injection, and the APT for this group was 6.6+4.4 mm. FIG. 11A shows the bright field and fluorescent images for the HS_HA group, and FIG. 11B shows the bright field and fluorescent images for the in vivo injection group.

Figure 12:
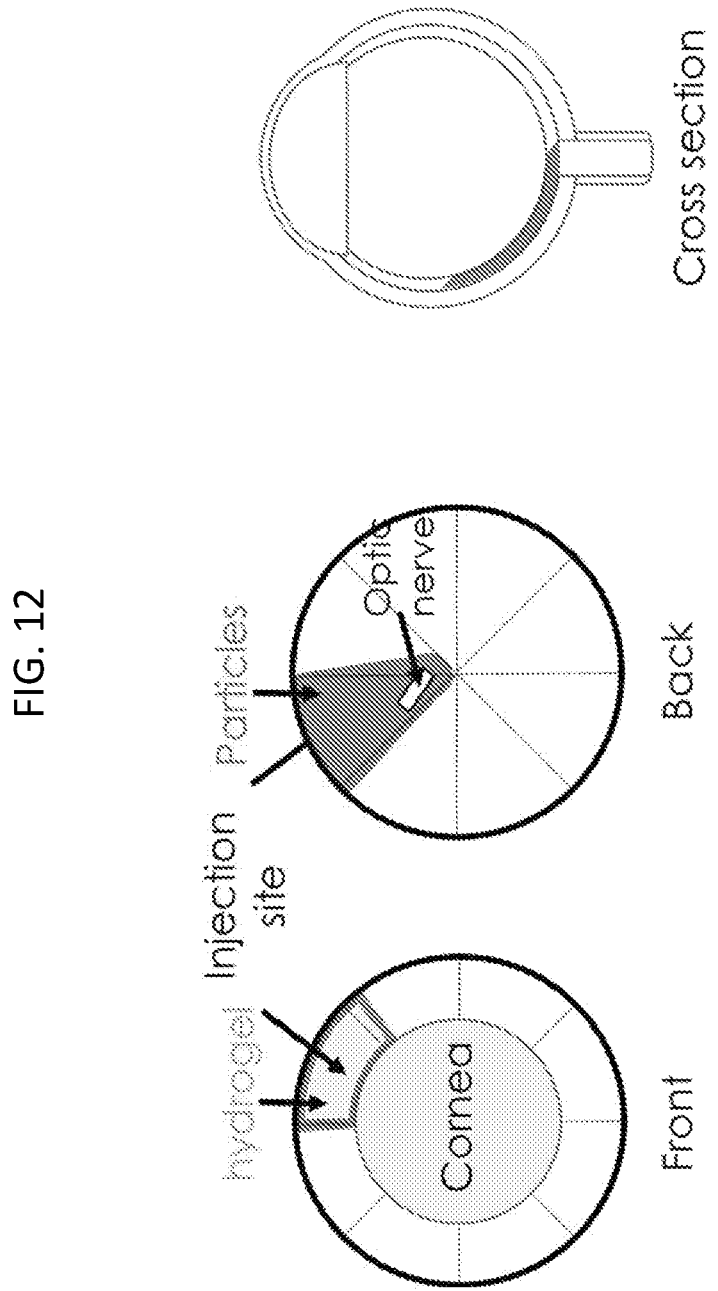
FIG. 12 is a schematic showing the concentration of drug particles at the back of the eye when the high-salt HA pushing formulation was used.

In summary, the study showed that the salts in the HA hydrogel drastically enhanced the pushing effect compared to the normal HA 4% hydrogel pushing formulation without added salt. The drug particles were pushed by the high-salt HA hydrogel formulation such that they were precisely targeted to the back of the eye, as shown schematically in FIG. 12.

Figure 13A:
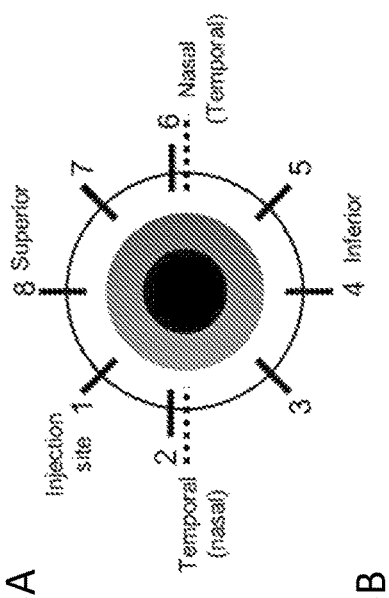
FIG. 13A is a schematic providing the locations at which SCS thickness was measured.
Figure 13B:
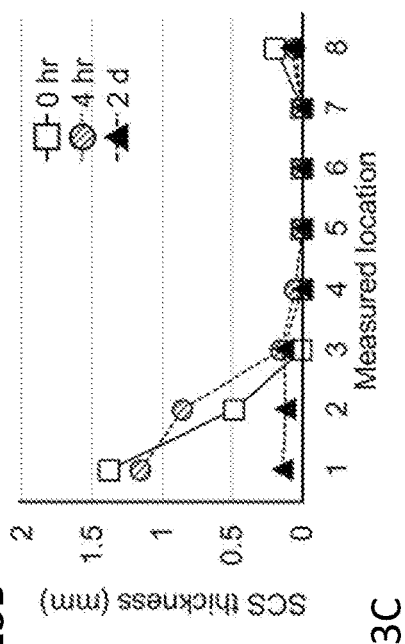
FIG. 13B shows the SCS thickness (mm) at each measured location and at 0 hr, 4 hr, or 2 days following injection of the HA hydrogel.
Figure 13C:
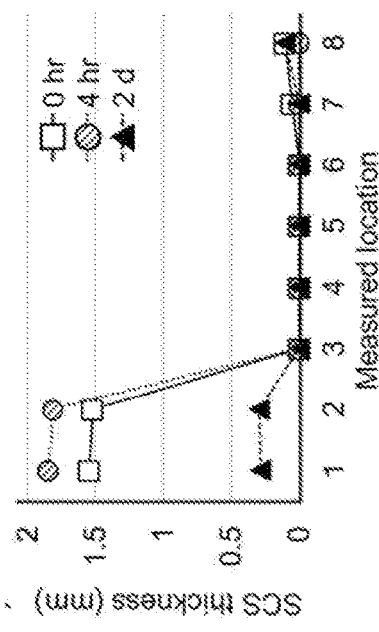
FIG. 13C shows the SCS thickness (mm) at each measured location and at 0 hr, 4 hr, or 2 days following injection of the high-salt HA hydrogel.

A study was conducted to assess the change in thickness of the SCS upon administration of hydrogel pushing formulations. HA hydrogel and high-salt HA hydrogel formulations were tested. FIG. 13A is a schematic showing the numerical identification of the locations within the eye. The SCS thickness was measured at 8 different areas as shown in FIG. 13A: The injection site is site (1), and the 7 other sites are as shown in the schematic figure. Thickness measurements were conducted using an ultrasound probe, and measurements were performed at three timepoints: 0 hr, 4 hr, and 2 days after the injection. FIG. 13B shows the thickness at each measured location of the SCS, and at each timepoint, after HA hydrogel injection. FIG. 13C shows the thickness at each measured location of the SCS, and at each timepoint, upon high-salt HA hydrogel injection.

The results of the study showed that both formulations resulted in increased thickness: high salt in the HA hydrogel resulted in increased thickness relative to the non-high salt HA hydrogel, particularly at 4 hours after injection. The high-salt HA hydrogel pushing formulation pushed the particles of the first formulation further from the injection site.

Example 2. Drug Delivery Targeted by Iontophoresis in the SCS of the Eye

Although SCS delivery improves targeting to sites of drug action, further control of drug distribution within the SCS would enable more precise targeting of drug to, for example, the posterior pole. In this Example, studies were conducted to assess whether application of an electric field within the SCS can drive charged molecules and particles, and thereby localize drug delivery to specific sites within the SCS of the eye.

Figure 14:
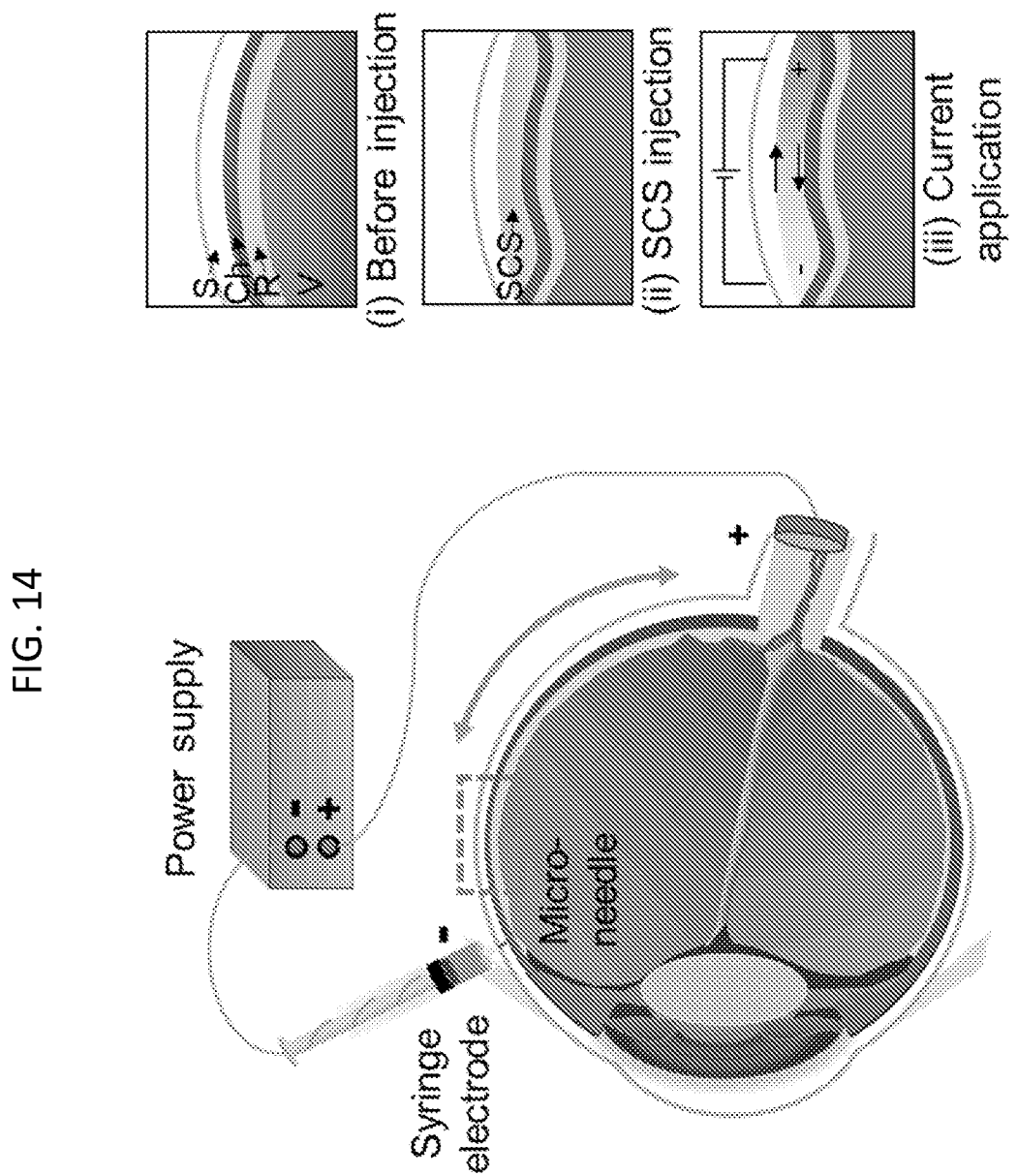
FIG. 14 is a schematic diagram of the SCS injection with iontophoresis application and its effects within the suprachoroidal space. Before injection (box (i)), the SCS is the potential space between the sclera (S) and the choroid (Ch). The retina (R) is located between the choroid and the vitreous (V). Box (ii) shows the suprachoroidal space after SCS injection of a particle formulation and before application of iontophoresis. Box (iii) shows the suprachoroidal space after the application of iontophoresis, wherein the applied current drives particle movement within the SCS toward the posterior segment of the eye.
Figure 15:
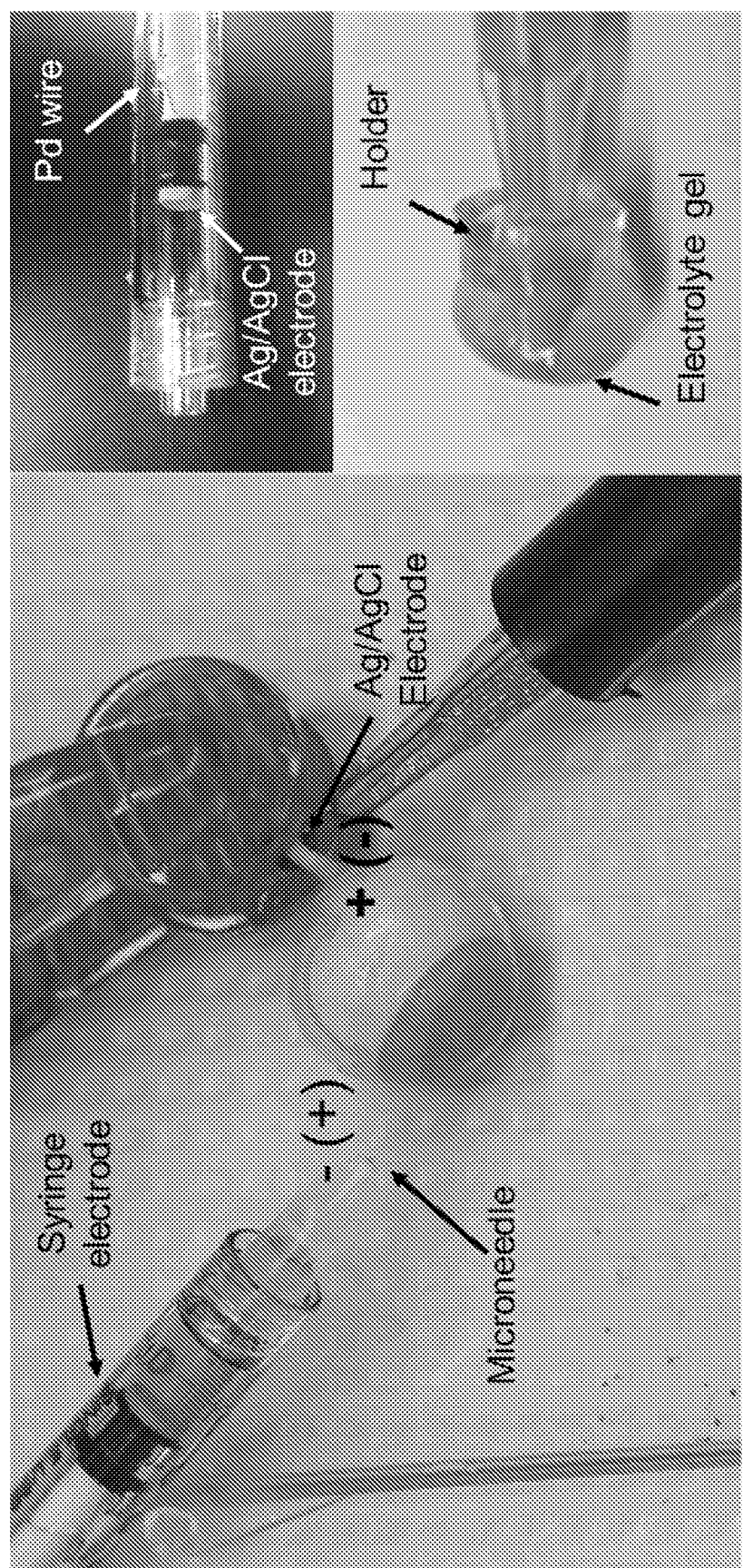
FIG. 15 provides photo images of exemplary materials for use in the iontophoretic microneedle system for injection, for example for injection into a rabbit eye ex vivo. The left panel and top right panel show an injection syringe with microneedle, wherein the injection syringe contains an electrode mounted on the end of the plunger and a Pd wire. The other electrode is attached at the end of the optic nerve as shown in the left panel image. The bottom right panel shows a microneedle holder with an electrolyte gel added to facilitate electrical connectivity between the microneedle device and the ocular tissue, and also to reduce the heat generated from the microneedle during iontophoresis application.

FIG. 14 provides a schematic representation of an exemplary method of iontophoretic targeting for ocular drug delivery via the SCS. A power supply is used to apply an electric field such that charged species delivered into the SCS concurrently or sequentially (e.g., by microneedle injection of a drug formulation into the SCS before, during, or after application of the electric field) move within the SCS by iontophoresis. As shown in box (i) of FIG. 14, before injection, the injection target for the drug formulation is between the sclera (S) and the choroid (Ch) (i.e., the SCS). Upon SCS injection, the SCS is filled with the drug formulation (box (ii) of FIG. 14). A current is applied to cause the charged species to move within the SCS (box (iii) of FIG. 14.). FIG. 15 provides photo images of exemplary materials for use in the iontophoretic microneedle system for injection, for example for injection into a rabbit eye ex vivo. For testing in rabbit eyes ex vivo, the injection syringe contained an electrode (cathode) mounted on the end of the plunger. The other electrode was attached at the end of the optic nerve (anode). A microneedle holder with electrolyte gel was added to facilitate electrical connectivity between the microneedle device and the ocular tissue, and also to reduce the heat generated from the microneedle during iontophoresis application.

New Zealand White rabbit eyes were injected ex vivo with 50 μL, 100 μL, or 200 μL of a formulation comprising red fluorescent particles. The particles were of 20 nm diameter and with a −50 mV zeta potential. The microneedle used was a hollow microneedle with a 30-gauge and 750 μm length. The syringe connected to the microneedle was modified by embedding a Ag/AgCl electrode in the chamber of the syringe, which was connected to a DC power supply. Either no current (i) or 0.14 mA for 3 minutes (ii) was applied. After injection, the eye was snap frozen and cut into 8 scleral petals. Fluorescent images of each eye were acquired, and particle extraction was performed for the distribution analysis. The percent particle distribution at 0-3 mm: 3-6 mm: 6-9 mm: or 9)+mm was assessed for each group.

Figure 16A:
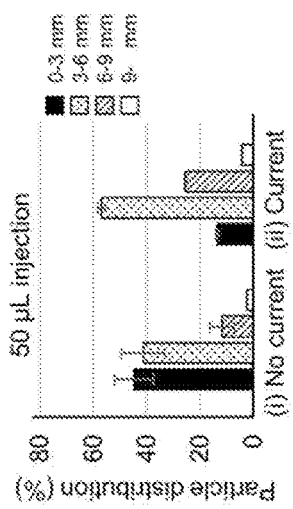
FIGS. 16A and 16B provide the fluorescence micrographs and % particle distribution, respectively, following 50 µL injection of the red fluorescent particle formulation, without (i) or with (ii) iontophoresis of 0.14 mA for 3 min following the injection.
Figure 16B:
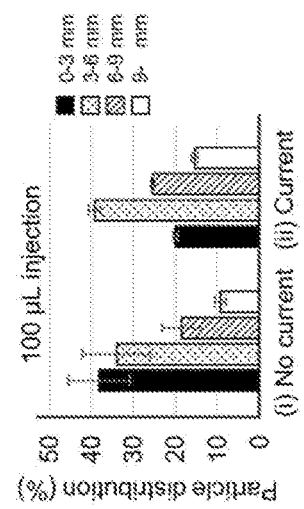
Figure 16C:
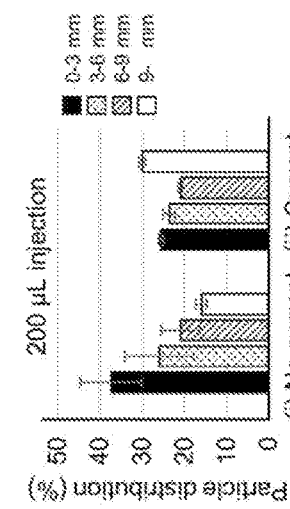
FIGS. 16C and 16D provide the fluorescence micrographs and % particle distribution, respectively, following 100 µL injection of the red fluorescent particle formulation, without (i) or with (ii) iontophoresis of 0.14 mA for 3 min following the injection.
Figure 16D:
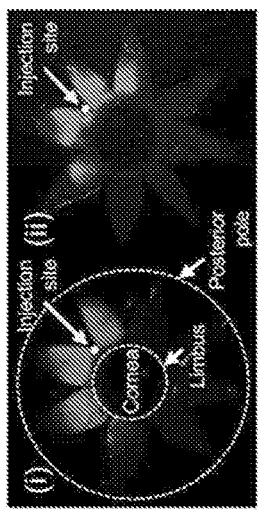
Figure 16E:
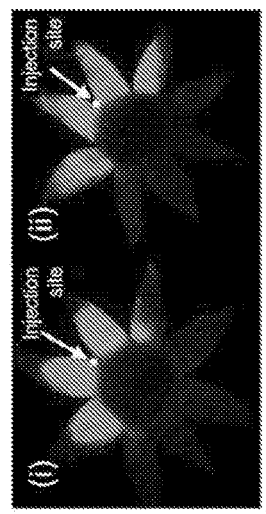
FIGS. 16E and 16F provide the fluorescence micrographs and % particle distribution, respectively, following 200 µL injection of the red fluorescent particle formulation, without (i) or with (ii) iontophoresis at 0.14 mA for 3 min following the injection. The fluorescence micrographs (FIGS. 16A, 16C, 16E) show representative flat mounts of the eye after dissection eye with radial cuts from the posterior pole to the limbus. The arrows point to sites of injection into the SCS. The average particle transfer (APT) for each group is provided in FIG. 16G. Total distance of the particle transfer was calculated based on the particle distribution profile, averaged particle transfer (APT). Averaged particle transfer (APT) (mm)=(1.5 mm×the particle distribution % of 0-3 mm area)+(4.5 mm×the particle distribution % of 3-6 mm area)+(7.5 mm×the particle distribution % of 6-9 mm area)+(10.5 mm×the particle distribution % of)–mm area). *, * Significance (One-way ANOVA, p<0.00024, 0.00070, and 0.03026, respectively) between without iontophoresis and with iontophoresis samples. Two-way ANOVA: 1) volume (p<0.000053), 2) current (p <0.00000043), and interaction of v and c (p<0.7547790). Graphs (FIG. 16B, 16D, 16F, 16G) present average+standard deviation based on 3 replicate samples (avg±SD, n=3).
Figure 16F:
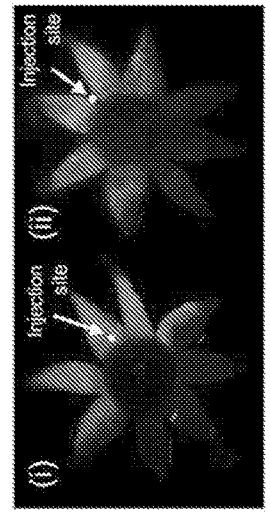
Figure 16G:
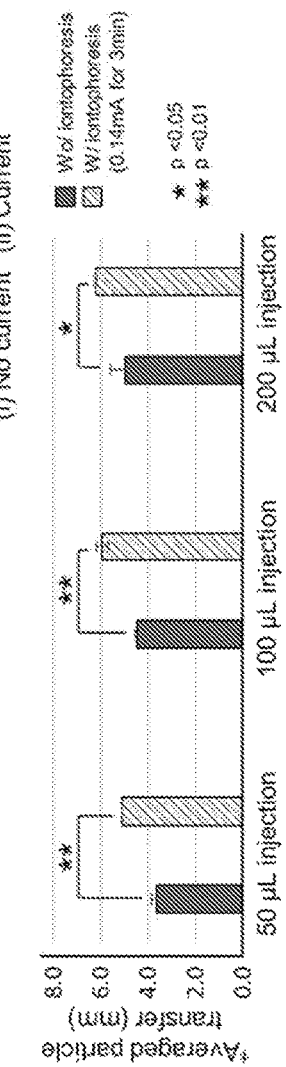

FIGS. 16A, 16C, and 16E show fluorescence micrographs of the distributions of the particles in the SCS after injection with 50 μL, 100 μL, or 100 μL volumes, respectively, and in either the absence (i) or the presence (ii) of iontophoresis. The particle distribution is provided graphically for the same groups in FIGS. 16B, 16D, and 16F for the same groups (50 μL, 100 μL, or 100 μL volumes, respectively, with or without iontophoresis. The average particle transfer (APT) for each group is provided in FIG. 16G. The profile of the APT clearly showed that the iontophoresis increased the particle localization to the posterior region of the eye. The portion of particles in the back of the eye was statistically significantly increased by the application of iontophoresis, as well as by increase in injection volume. With a 200 μL volume injection, 15.9% of particles were found in the most posterior quadrant (9 mm+) in the absence of current. However, when iontophoresis was applied (i.e., with current), 30% of the particles were found in the most posterior quadrant.

Next, the effect of altering the current on drug particle targeting was assessed. The time of iontophoresis was held at 3 min, and an injection volume of 200 μL was used. Iontophoresis currents of 0) mA, 0.14 mA, and 0.7 mA were tested. FIG. 17A provides the fluorescence micrographs showing the distribution of red-fluorescent particles in the SCS without iontophoresis (0) mA (i)), or with iontophoresis with a current of 0.14 mA (ii) or 0.7 mA (iii). FIG. 17B shows the particle distribution % for each group and FIG. 17C shows the APT for each group. The study showed that particle distribution to the 9+mm area was increased by increasing the current. In addition, the APT data showed that increased current increased the delivered distance of particles. However, added particle delivery was not as enhanced as the current was increased (i.e., 5 fold increase from 0.14 to 0.7 mA). In addition, there was some tissue burn after application of 0.7 m A iontophoresis. 0.14 mA iontophoresis was selected for further studies.

A study was conducted to determine the effect of the application time of iontophoresis. The iontophoresis current was held at 0.14 mA and the injection volume of 200 μL was used. Iontophoresis application times of 1.5 min, 3 min, and 5 min, were compared. FIG. 18A provides the fluorescence micrographs showing the distribution of red-fluorescent particles in the SCS without iontophoresis application times of 1.5 min (i), 3 min (ii), or 5 min (iii). FIG. 18B shows the particle distribution % for each group and FIG. 18C shows the APT for each group. The study showed that particle distribution to the back of the eye was clearly increased when the application time was increased from 1.5 min to 3 min. However, there was less of an increase or no significant increase when comparing 3 min to 5 min of application time. The APT for the 3 min and 5 min groups were similar. Without wishing to be bound by theory, since the SCS collapse of the rabbit eye ex vivo starts around 5 minutes, this may inhibit the particle delivery backward. In addition, with increased application time the particles aggregate, which may also inhibit posterior delivery.

Figure 19A:
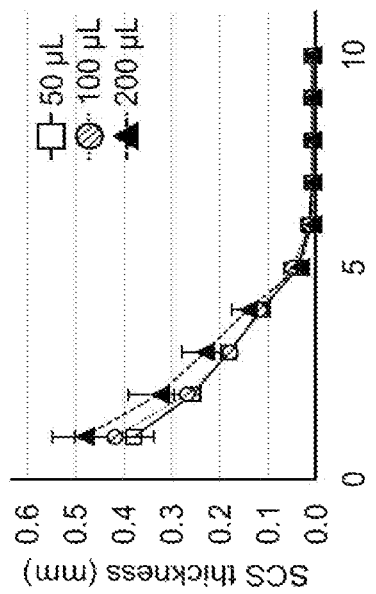
FIG. 19A is a line graph showing the thickness of the SCS over time with different injection volumes (50, 100, or 200 μL). The thickness was measured at 1 minute intervals from 0 min to 10 min.
Figure 19B:
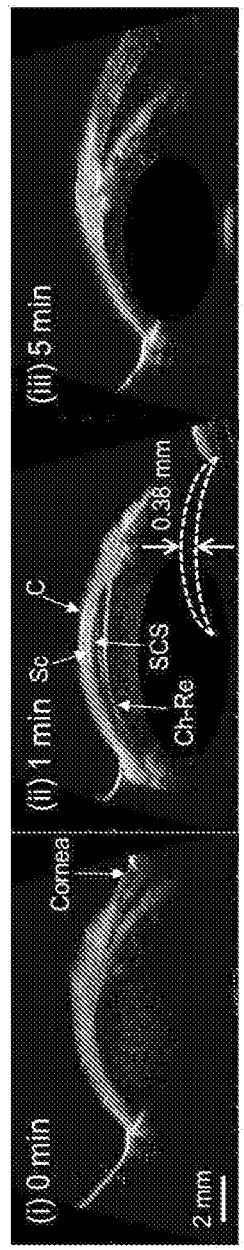
FIG. 19B shows ultrasound images of the rabbit eye ex vivo before injection (0 min, (i)), 1 minute after injection (ii), or 5 minutes after injection (iii) with an injection volume of 50 μL.
Figure 19C:
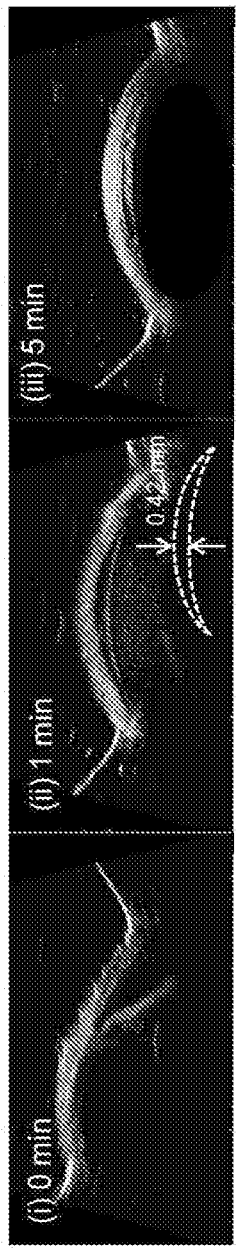
FIG. 19C shows ultrasound images of the rabbit eye ex vivo before injection (0 min, (i)), 1 minute after injection (ii), or 5 minutes after injection (iii) with an injection volume of 100 μL.
Figure 19D:
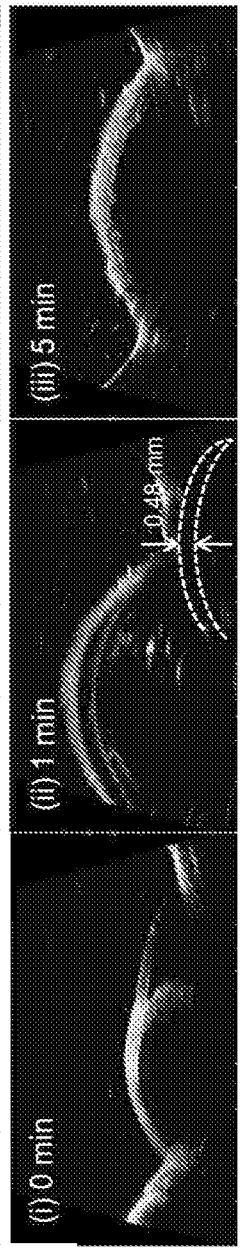
FIG. 19D shows ultrasound images of the rabbit eye ex vivo before injection (0 min, (i)), 1 minute after injection (ii), or 5 minutes after injection (iii) with an injection volume of 200 μL.
Figure 20A:
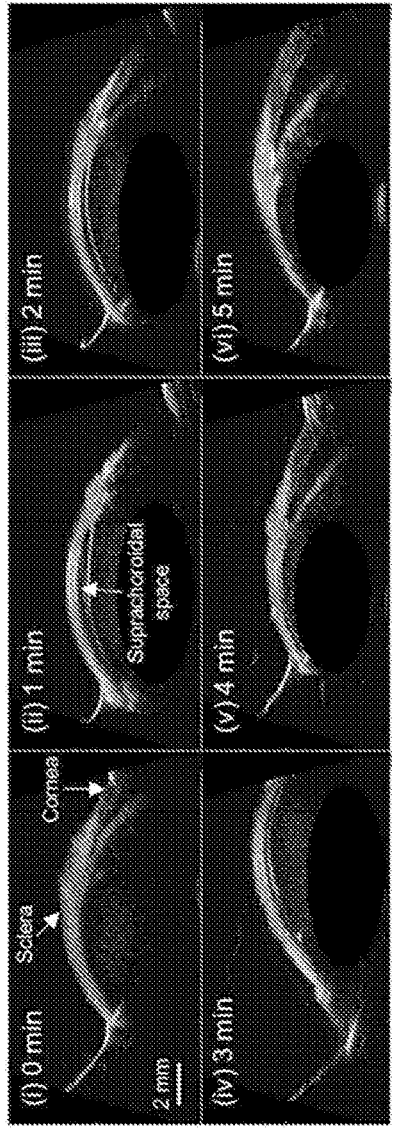
FIG. 20A shows ultrasound images of the rabbit eye ex vivo after SCS injection with 50 μL at 0 min (i), 1 min (ii), 2 min (iii), 3 min (iv), 4 min (v), or 5 min (vi).
Figure 20B:
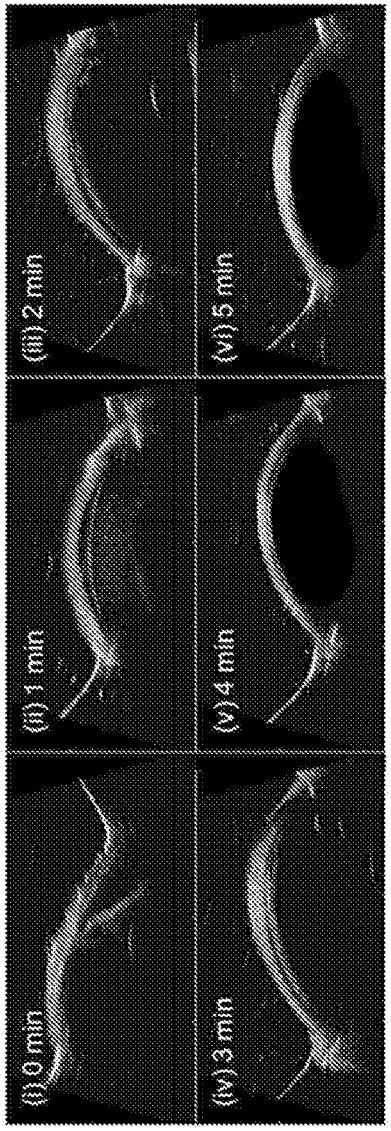
FIG. 20B shows ultrasound images of the rabbit eye ex vivo after SCS injection with 100 μL at 0 min (i), 1 min (ii), 2 min (iii), 3 min (iv), 4 min (v), or 5 min (vi).
Figure 20C:
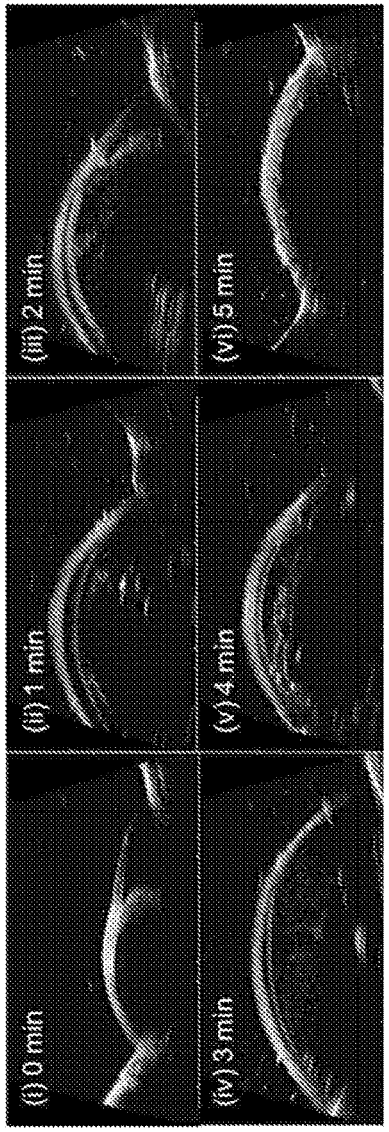
FIG. 20C shows ultrasound images of the rabbit eye ex vivo after SCS injection with 200 μL at 0 min (i), 1 min (ii), 2 min (iii), 3 min (iv), 4 min (v), or 5 min (vi).

To assess the SCS collapse of the rabbit eye ex vivo, thickness of the SCS was measured by an ultrasound probe. FIG. 19A shows the thickness of the SCS over time with different injection volumes (50, 100, or 200 μL). FIGS. 19B, 19C, and 19D show ultrasound images of the rabbit eyes ex vivo before injection (0) min, (i)), 1 minutes after injection (ii), or 5 minutes after injection (iii) with injection volumes of 50 μL (FIG. 19B) 100 μL (FIG. 19C) and 200 μL (FIG. 19D). The SCS collapse time was around 5 min regardless of the injection volume. Thus, the SCS collapse of the eye ex vivo affect the particle delivery to the back of the eye at around 5 min. Ultrasound images of the rabbit eyes ex vivo at 0 min, 1 min, 2 min, 3 min, 4 min, and 5 min are also shown in FIGS. 20A-20C for 50 μL (FIG. 20A), 100 μL (FIG. 20B), and 200 μL (FIG. 20C) injection volumes. The SCS thickness decreased gradually over time.

Figure 21B:
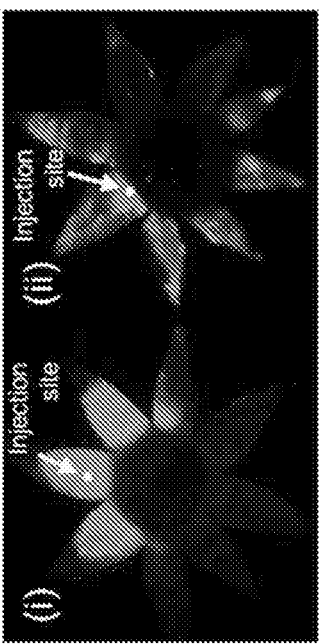
FIG. 21B shows the fluorescence micrographs providing the distributions of the red fluorescent particles in the SCS after no iontophoresis (i) or after the iontophoretic direction was reversed (−0.07 mA: (ii)). The fluorescence micrographs show representative flat mounts of the eye after dissection eye with radial cuts from the posterior pole to the limbus. The arrows point to sites of injection into the SCS.
Figure 21C:
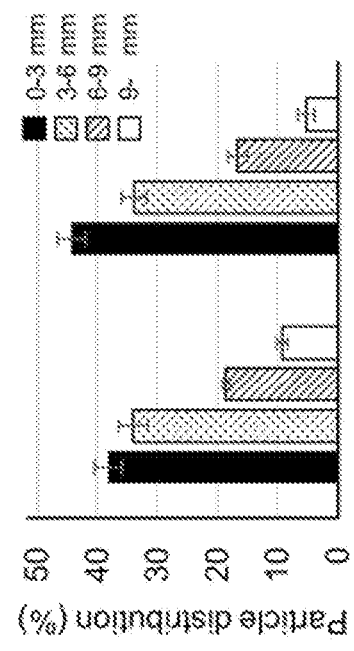
FIG. 21C provides the particle distribution %.
Figure 21D:
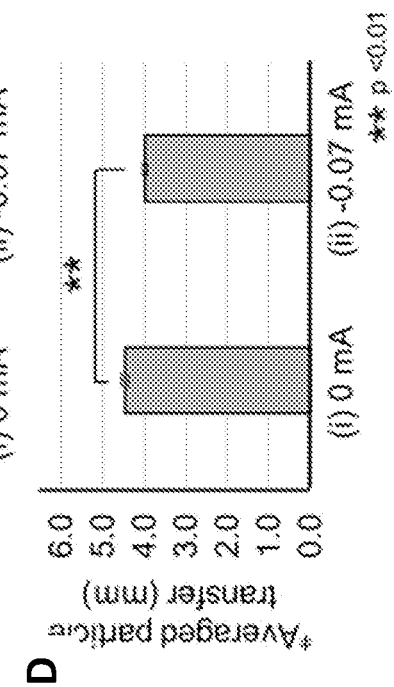
FIG. 21D shows the APT. ** Significance (One-way ANOVA, p<0.00131) between (i) 0 mA and (ii)—0.07 mA of the APT. For 21C and 21D, the graphs present average±standard deviation based on 3 replicate samples (avg±SD, n=3).
Figure 21A:
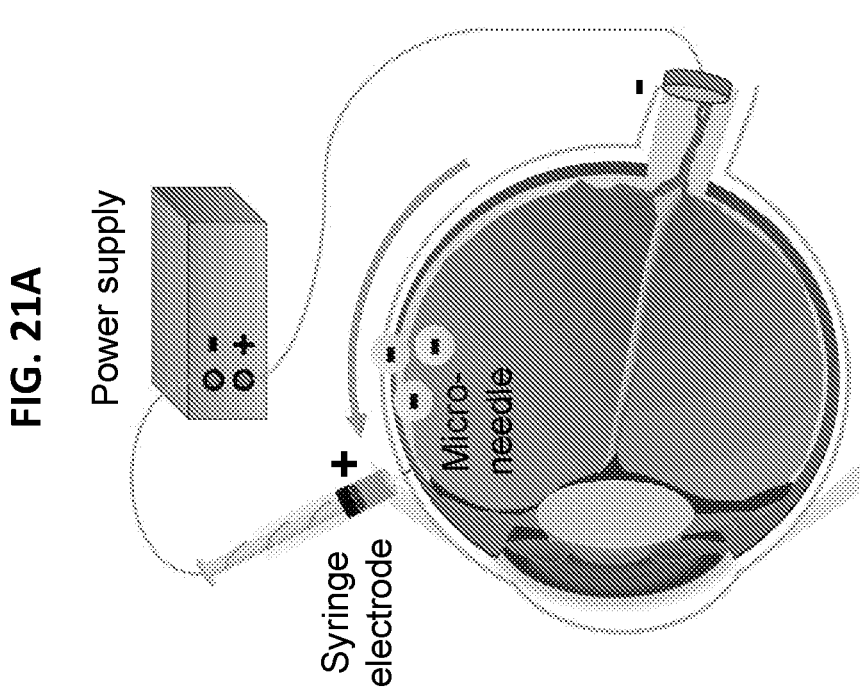
FIG. 21A is a schematic diagram depicting the reversed current study.

A study of the effect of the iontophoretic direction within the SCS was conducted, with the anode at the injection site and the cathode at the optic nerve. A schematic of the study is provided in FIG. 21A. For this study, particle distribution and transfer was assessed after injection of 100 μL of particle formulation followed by no iontophoresis (i) or reversed direction iontophoresis (−0.07 mA: (ii)). FIG. 21B shows the fluorescence micrographs providing the distributions of the red fluorescent particles in the SCS. The particles stayed around the injection site when the current direction was changed. FIG. 21C provides the particle distribution %, and FIG. 21D shows the APT. Particle distribution focused to the front rather than the back of the eye when the current direction was changed.

Together, the ex vivo studies showed that charged particles injected into the SCS were delivered more preferentially to the anterior or posterior portions of the SCS, depending on the electric current and its polarity. Accordingly, the iontophoresis method provided herein is a viable strategy for targeting drug delivery to specific regions within the SCS.

Figure 22:
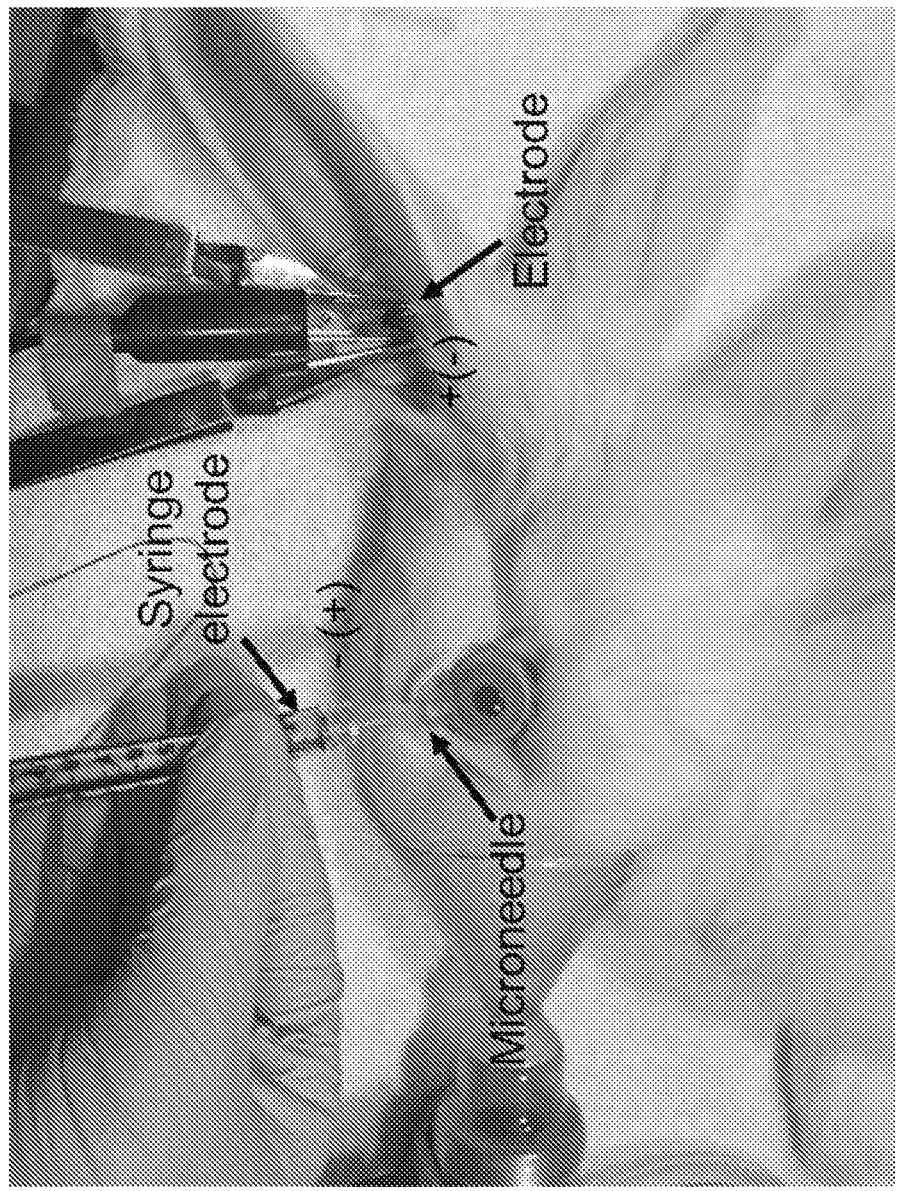
FIG. 22 is a photograph image of an exemplary in vivo delivery using the iontophoretic ocular drug delivery system. The microneedle embedding a Ag/AgCl electrode was injected to the SCS from supranasal location of the eye. The other Ag/AgCl electrode was attached on the ear of the rabbit.
Figure 23A:
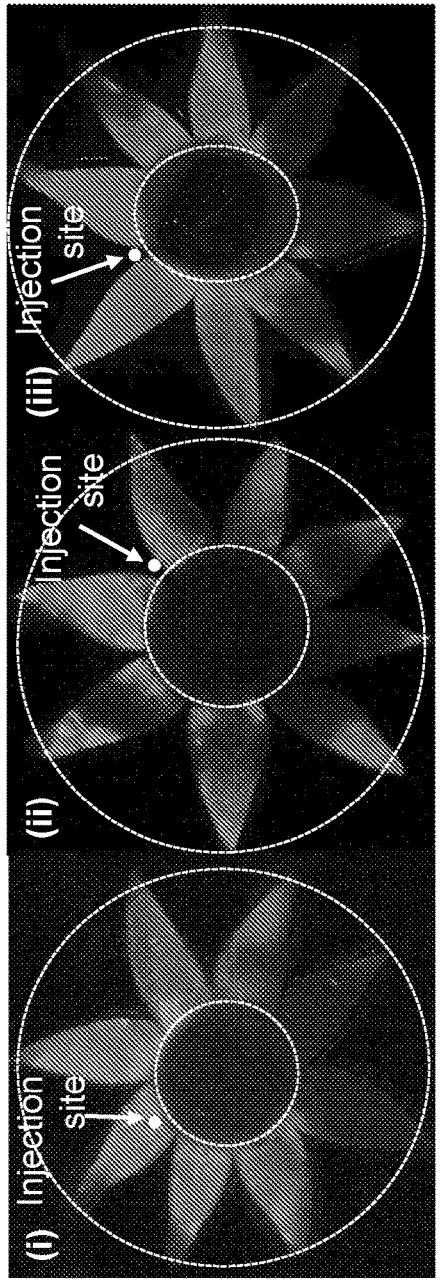
FIGS. 23A-23C provide the results of in vivo injection of 100 μL red fluorescent particles using iontophoresis. The iontophoresis condition was 0.14 mA for 3 minutes.
Figure 23C:
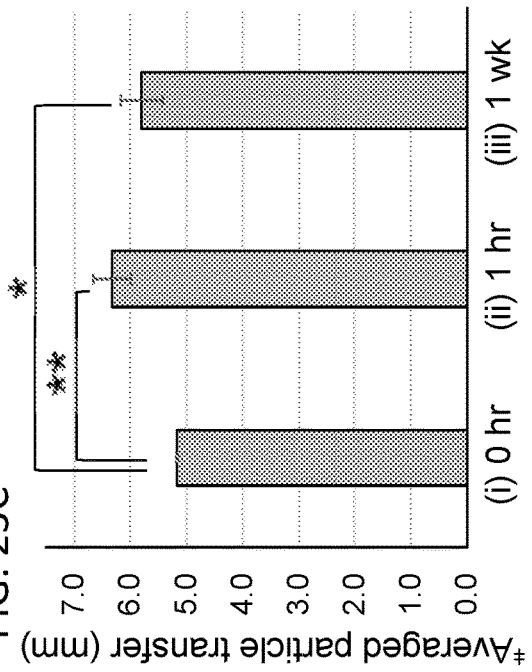
Figure 23B:
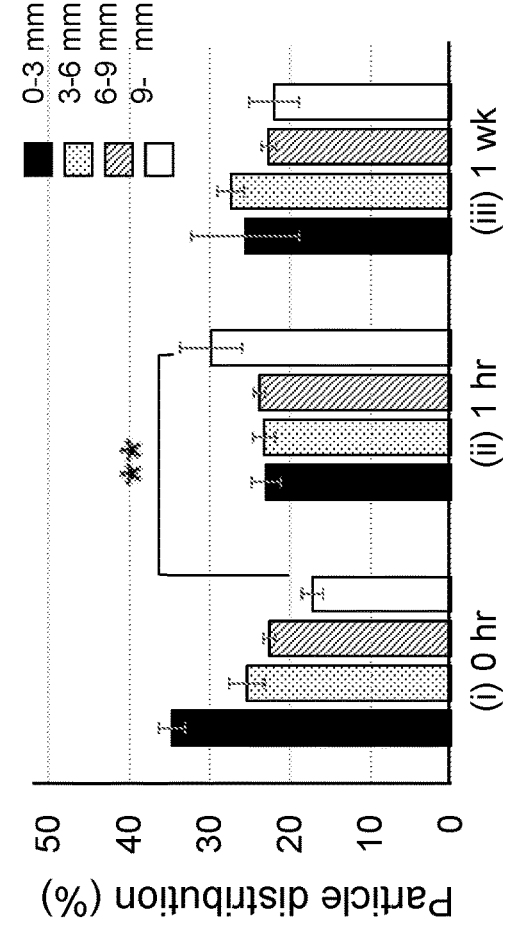

FIG. 22 is a photograph image of an exemplary in vivo delivery using the iontophoretic ocular drug delivery system. FIG. 23A provides fluorescent micrographs showing the distribution of the red-fluorescent particles in the SCS after in vivo injection of a volume of 100 µL red fluorescent particle formulation and iontophoresis of 0.14 mA for 3 minutes. FIG. 23B shows the particle distribution percent at 0 hr, 1 hr, and 1 week after injection. FIG. 23C shows the APT. Although the portion of the particles in the posterior was decreased from (ii) 1 hour to (iii) 1 week, the iontophoresis clearly enhanced the particle delivery to the back of the eye.

Figure 24B:
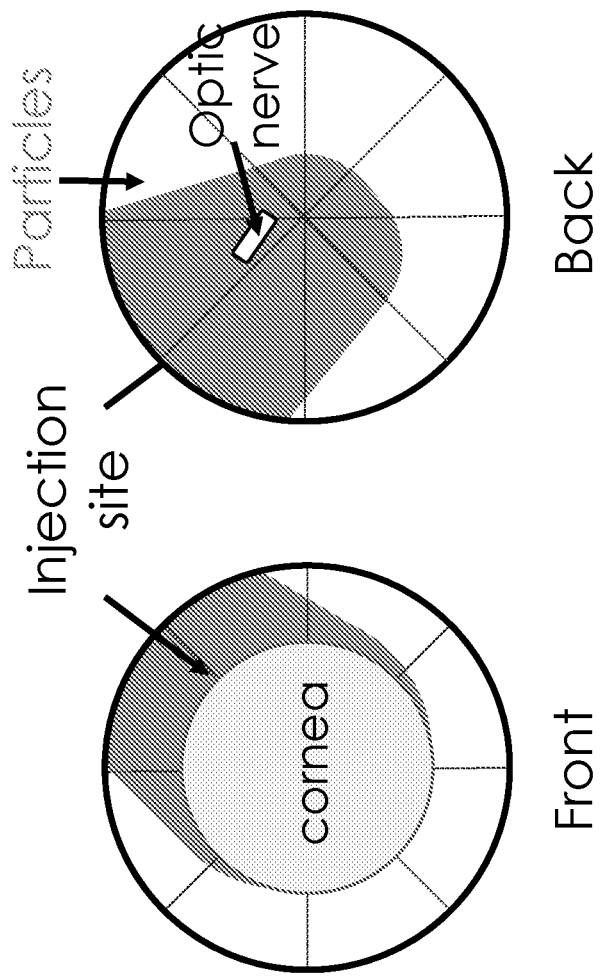
FIG. 24B is a schematic diagram showing the particle distribution to the back of the eye, if the eye were reconstructed.
Figure 24A:
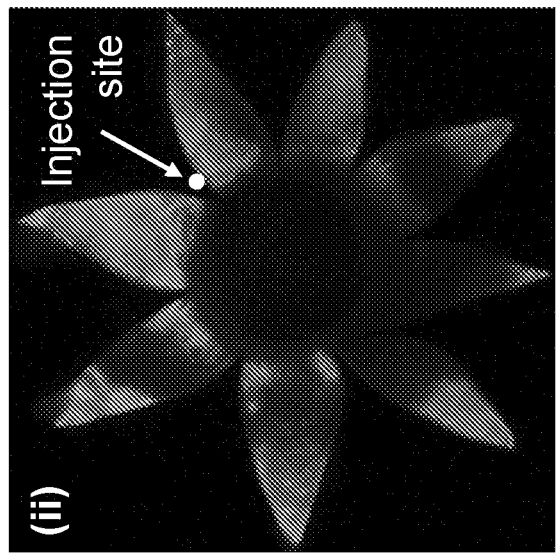
FIG. 24A shows the red particles by fluorescent micrograph 1 hour after in vivo injection of 100 μL red fluorescent particles and iontophoresis using a current of 0.14 mA for 3 minutes (as shown in FIG. 23A(ii).

FIG. 24A shows the red particles by fluorescent micrograph 1 hour after in vivo injection of 100 µL red fluorescent particles and iontophoresis using a current of 0.14 mA for 3 minutes (as shown in FIG. 23A(ii)). FIG. 24B is a schematic diagram showing the particle distribution to the back of the eye, if the same eye as shown in FIG. 24A eye were reconstructed. Notably, the discontinued regions in the middle of the petal are not caused from missing tissue. Rather, these regions show the particle delivery around optic nerve derived by iontophoresis. In contrast to the ex vivo studies, the localization of particles in the eye after in vivo administration showed the particles were attracted much more strongly by the iontophoresis.

Figure 25A:
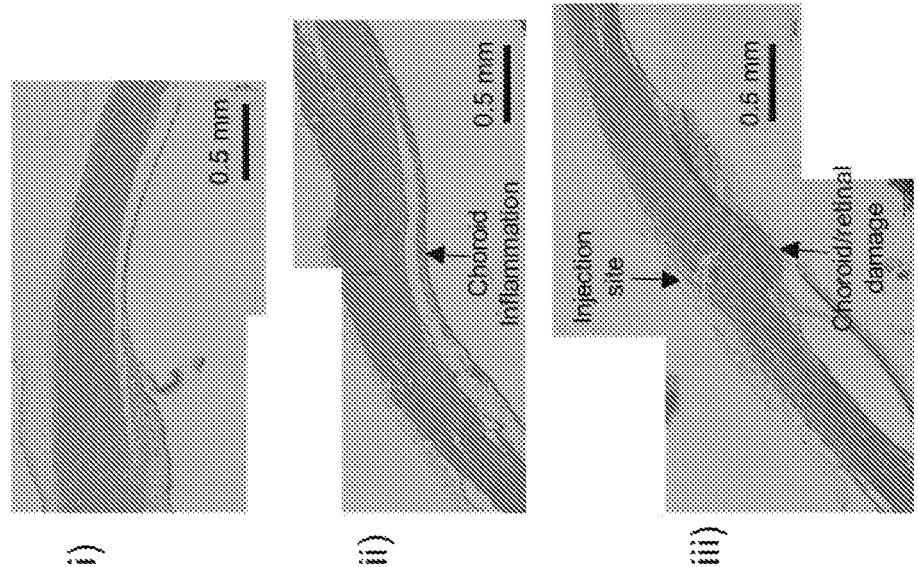
FIG. 25A shows a histological image of an untreated eye.
Figure 25B:
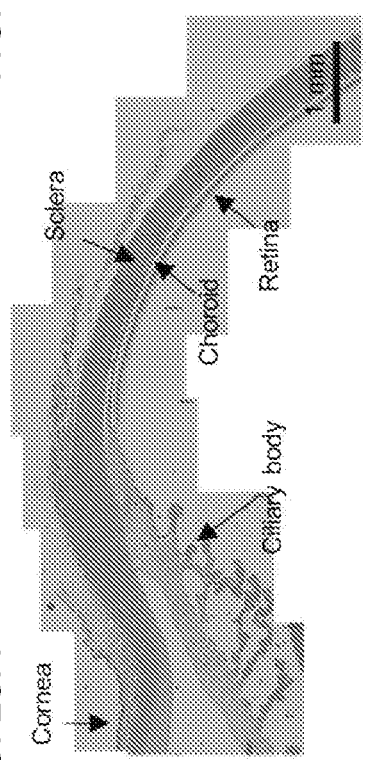
FIG. 25B shows three images of eyes 1 day after in vivo injection and iontophoresis application. One eye showed no symptoms (i). One eye showed choroid inflammation (ii). One eye showed choroid/retinal damage (iii).
Figure 25C:
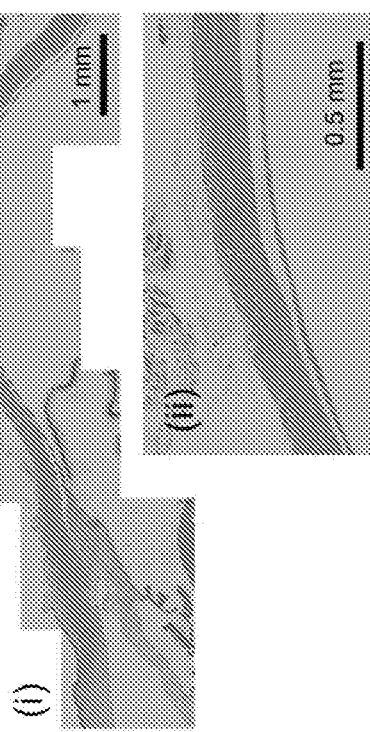
FIG. 25C shows an eye 1 week after in vivo injection and iontophoresis application. Image (ii) is a magnification of image (i). No symptoms were observed in the eyes 1 week after the injection and iontophoresis application.

Histology images of the rabbit eye after in vivo injection and iontophoresis were taken to determine if the procedure caused any damage to the eyes. FIG. 25A shows the intact, untreated eye. FIG. 25B shows three images of eyes 1 day after in vivo injection and iontophoresis application. FIG. 25C shows two images of an eye 1 week after in vivo injection and iontophoresis application. Although two of the three eyes after day 1 showed inflammation or choroid/retinal damage near the injection site, there were no symptoms observed in any eyes 1 week after injection. Thus, the study showed that there may be symptoms around 1 day after the iontophoresis procedure, but that eyes are fully recovered within 1 week. There were no other symptoms observed in the rabbits that received the treatment.

Example 3. Highly Targeted Ocular Drug Delivery by Iontophoresis and Hydrogel Pushing in the Suprachoroidal Space Suprachoroidal space (SCS) injection using a microneedle has been demonstrated as a means to better target drug delivery specifically to the posterior eye (e.g., macula and optic nerve). Injecting into the SCS, a potential space between the choroid and sclera, allows drug to flow circumferentially at the choroid-sclera interface typically from an anterior injection site to near the limbus with high bioavailability. The safety and tolerability of SCS injection using a microneedle have been shown in clinical trials. Although SCS injection targets drug delivery to choroid and retina, it does not specifically target the posterior pole. Moreover, typical SCS injection volumes (e.g., ≤100 µL in the rabbit eye) are insufficient to flow injected drugs around the macula or optic disk. Greater targeting efficiency within the SCS could provide still better safety and efficacy.

To advance drug targeting to posterior SCS, a previous study (e.g., described herein in Example 2) introduced iontophoresis-mediated drug delivery methods wherein charged drug model particles were delivered to the back of the eye via the SCS. Although over 50% of the drug particle was delivered further posteriorly to the posterior segment of the SCS (i.e., >6 mm posterior to the limbus), there was still around 25% of the drug particles around injection sites (i.e., <3 mm posterior to the limbus).

Figure 26:
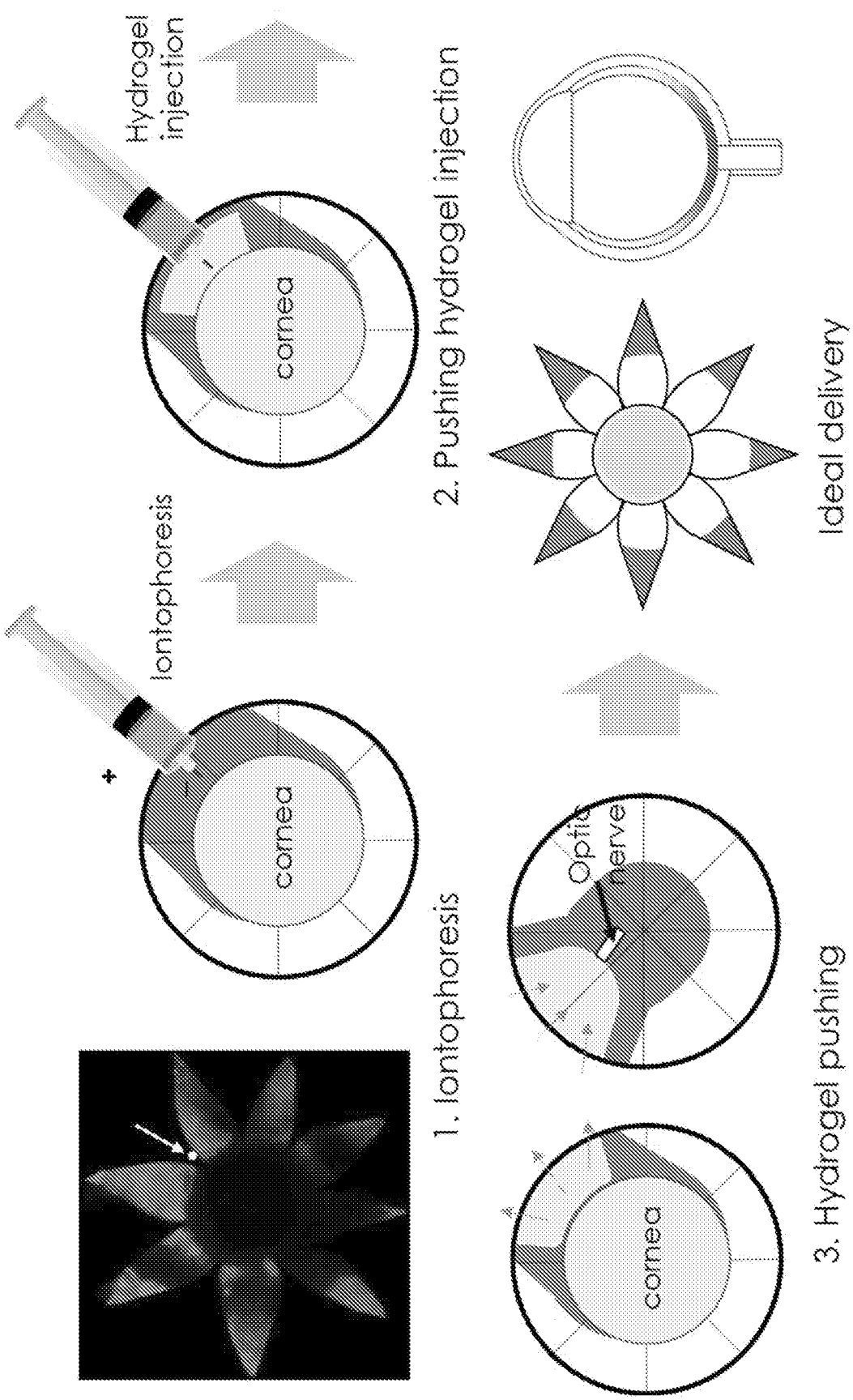
FIG. 26 provides a fluorescent image and a schematic depiction of one embodiment of the combination of iontophoresis with pushing hydrogel injection for delivery of formulations to the back of the eye.
Figure 27:
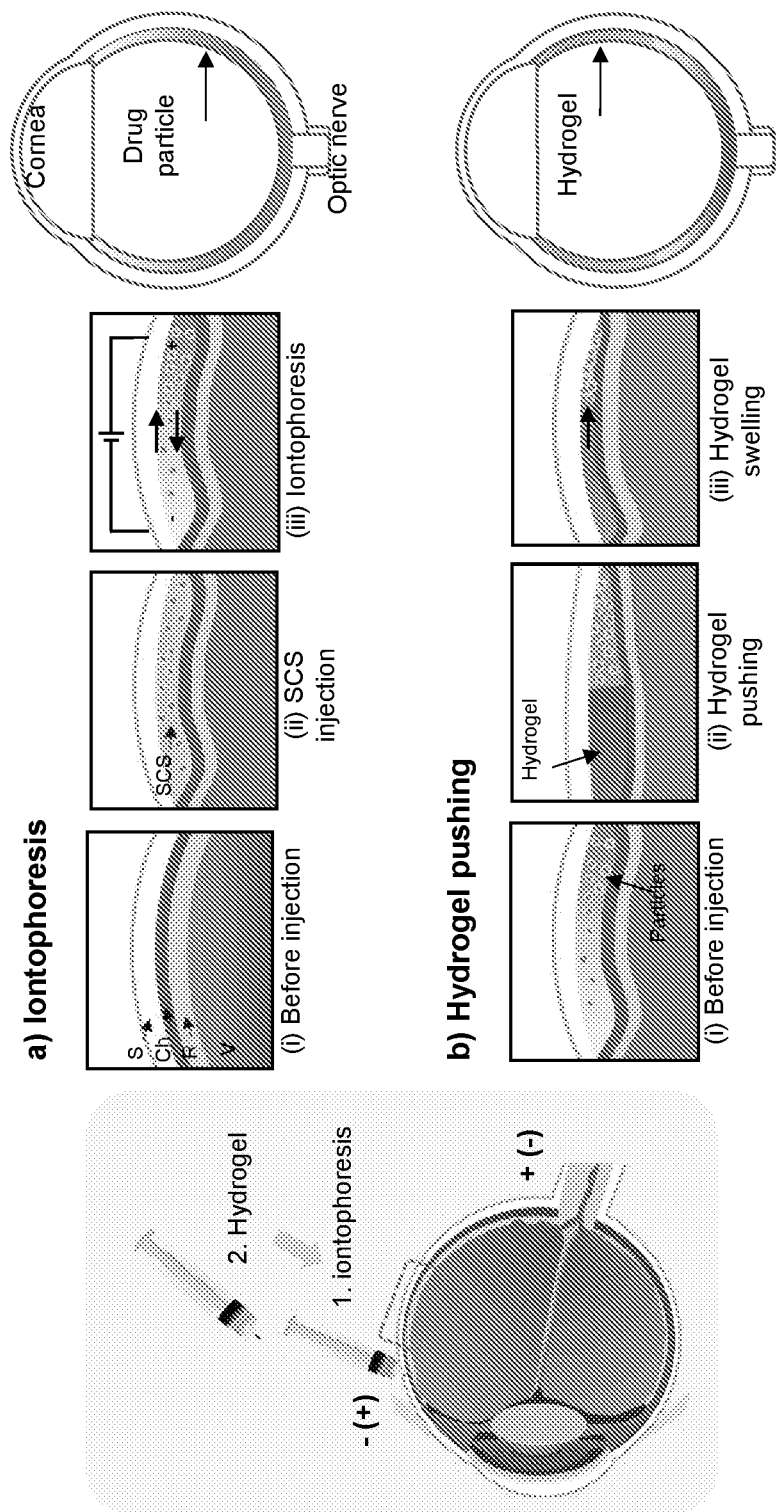
FIG. 27 is an additional schematic depiction of one embodiment of the combination of iontophoresis with pushing hydrogel injection for delivery of formulations to the back of the eye.

Thus, the present study was conducted to determine if the addition of hyaluronic acid (HA) hydrogel pushing formulation into the SCS, administered right before or after the iontophoresis, would further deliver the drugs around the injection site to the posterior. The HA hydrogel injection not only pushes the particles round the injection site, but also transfer the particles further toward the posterior by hydrogel swelling. Schematic diagrams of the process are provided in FIGS. 26 and 27. FIG. 28A shows the results of different current conditions and injection of 50 µL drug particle formulation (without pushing formulation). Current conditions of 0.15 mA, 0.3 mA, and 0.5 mA were tested, and 0.5 mA was selected for the combination study. FIG. 28B shows the results of different HA formulations for the pushing formulation (tested in the absence of iontophoresis). 1% HA, 2% HA, 3% HA, and 4% HA formulations were tested. 4% HA pushed the particles without mixing, and this concentration was selected for the combination study.

Figure 29A:
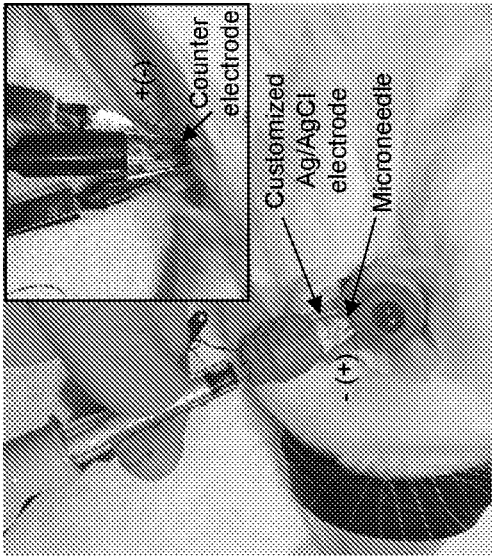
FIG. 29A shows the ex vivo setup for the combined iontophoresis and hydrogel pushing study.
Figure 29B:
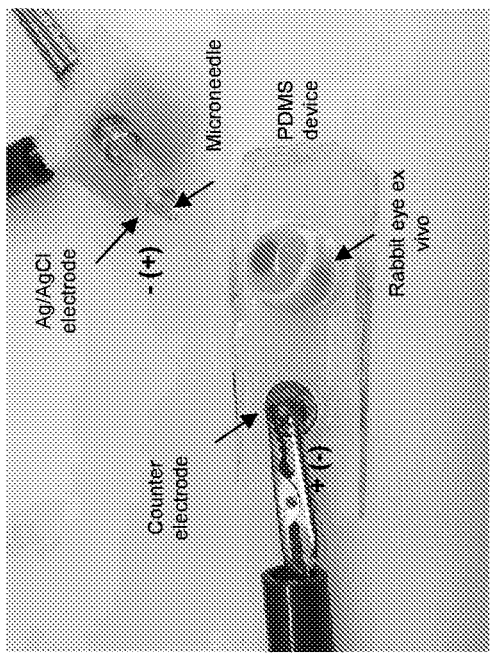
FIG. 29B shows the in vivo setup for the combined iontophoresis and hydrogel pushing study.

In the combination drug delivery system, a customized Ag/AgCl electrode was located to around a microneedle for iontophoresis. The system was applied to rabbit eyes ex vivo (FIG. 29A) and in vivo (FIG. 29B) to provide an assessment of the delivery and safety of this iontophoretic SCS injection system.

A 30 gauge hollow microneedle, 750 µm in length, was used to inject negatively charged fluorescent particles into the SCS of the rabbit eye ex vivo. A customized ring type Ag/AgCl electrode was attached around a microneedle and the electrode was connected to a DC power supply. A polydimethylsiloxane (PDMS) microdevice was fabricated to apply iontophoresis to the rabbit eye ex vivo and provide similar injection conditions to in vivo injection. Two 0.75 inch diameter holes were made and connected by a single channel, 0.75×0.2×2.2 inch. A rabbit eye and a disk typed Ag/AgCl electrode (0.5 inch diameter) were placed in the holes. The channel was filled with Hank's balanced salt solution (HBSS) buffer. 50 µL of the particle solution was infused into the SCS through the microneedle, simultaneously with application of electric current (0.5 mA) for 3 minutes from the injection site to another Ag/AgCl electrode. To deliver the particles around the injection site (anterior SCS) to the back of the eye, 50 µL of 4% (w/v) hyaluronic acid hydrogel was infused into the SCS right after the iontophoresis. To confirm the effect of the HA hydrogel swelling, the injected rabbit eyes were incubated in HBSS buffer at 37° C., for 6 h. After the injection and the incubation, particle distribution in the SCS was analyzed.

Figure 30:
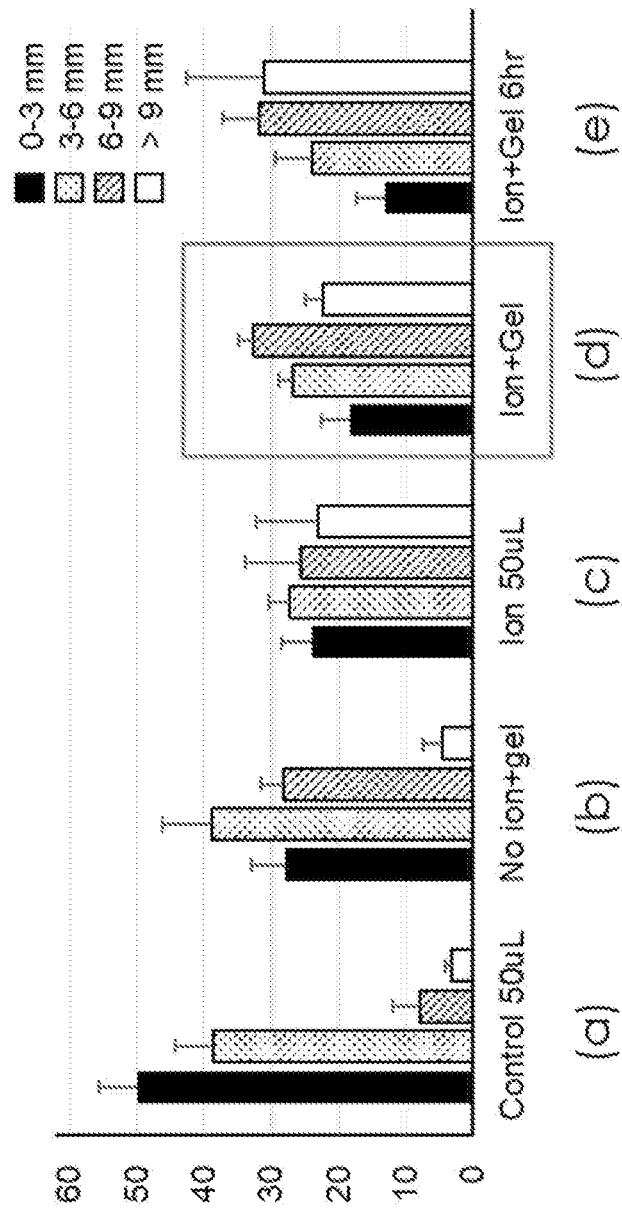
FIG. 30 shows the ex vivo results of a control injection (particles are preferentially distributed in the anterior area): 4% hydrogel pushing after particle injection, without iontophoresis (b): iontophoresis only after particle injection (no hydrogel injection: (c)): the combination of iontophoresis and pushing formulation administration (iontophoresis was applied first, followed by hydrogel injection: (d)); or the combination of iontophoresis and pushing formulation administration and an incubation for 6 h at 37° C. to induce hydrogel swelling (e).

The results of the study are provided in FIG. 30. Particles (50 µL) injected into the SCS of the rabbit eyes ex vivo in the absence of an electric field were distributed more toward the anterior region, ~50% of the particle formulation was found in the anterior quadrant of the SCS (i.e., <3 mm posterior to the limbus) and only ~10% of the particle formulation was found in the posterior quadrant of the SCS (i.e., >6 mm posterior to the limbus). The particle injection with hydrogel injection (50 µL), without iontophoresis, delivered ~28% of particles in the anterior SCS and ~32% of particles in the posterior SCS. When the iontophoresis was applied only (no hydrogel pushing), ~24% of particles were delivered to the anterior SCS and ~49% of particles located in the posterior SCS. Where the iontophoresis was applied first and then hydrogel pushing followed, ~18% of particles were distributed in the anterior SCS and ~55% of particles were in the posterior SCS. After 6 h incubation of the eye which was applied iontophoresis first and injected HA hydrogel second, ~13% of particles were distributed in the anterior SCS and ~63% of particles in the posterior SCS. Therefore, the study showed that the combination of iontophoresis with hydrogel pushing, including incubation time ex vivo to allow hydrogel swelling, resulted in an increase in the delivery of particles to the further posterior positions in the posterior segment of the eye.

Figure 31:
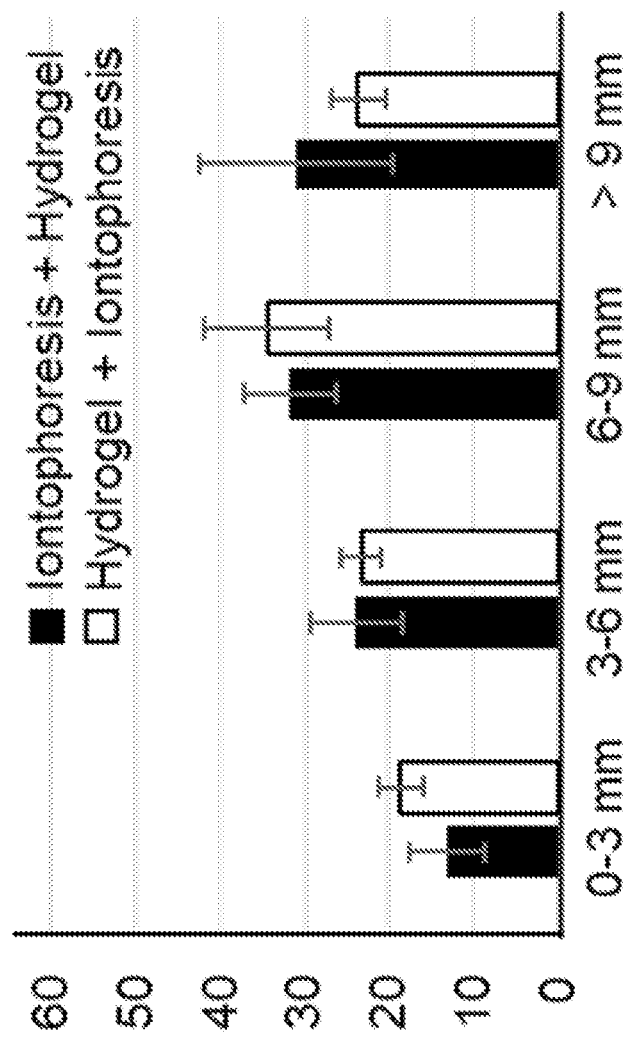
FIG. 31 shows the results of a comparison of the order of iontophoresis and gel pushing. The black squares show the results of application of iontophoresis prior to hydrogel injection. The white squares show the results of iontophoresis application after hydrogel injection.

An additional study was conducted to determine if applying iontophoresis after hydrogel pushing, rather than immediately before hydrogel pushing, would increase or decrease particle delivery to the posterior SCS. FIG. 31 shows the comparison of the localization of the particles within the eye when the iontophoresis was applied before or after the administration of the hydrogel pushing formulation. There was no significant difference between the two groups.

Figure 32:
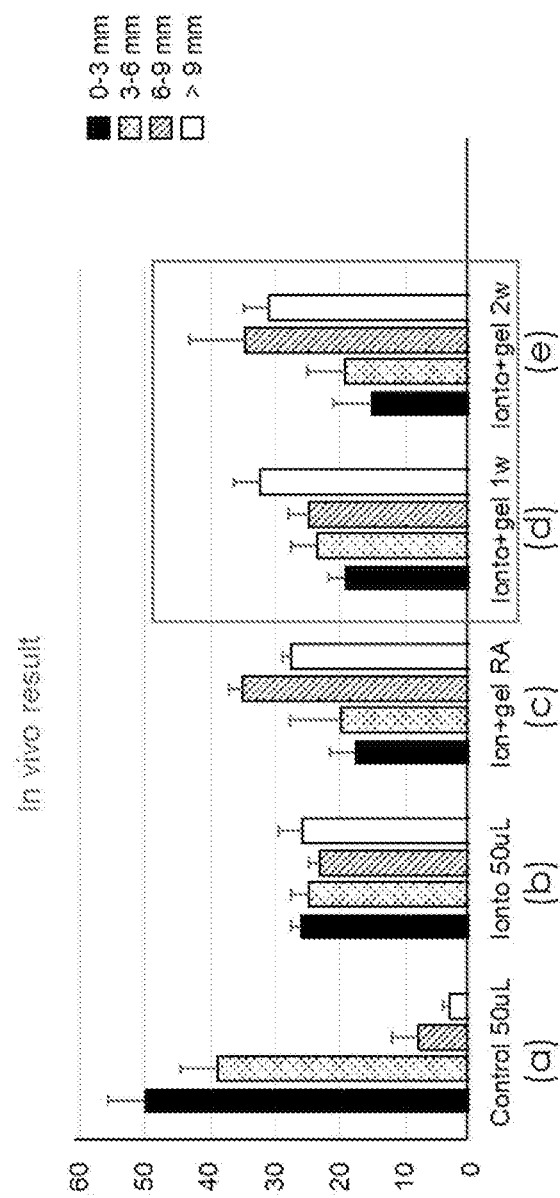
FIG. 32 shows the results of the in vivo combination study. (a) is the control (50 μL particles only). (b) is iontophoresis only. (c) is iontophoresis+gel administration right after injection. (d) is iontophoresis+gel administration 1 week after the injection. (e) is iontophoresis+gel administration 2 weeks after the injection.

Based on the ex vivo results, SCS injection into the New Zealand White rabbit eyes was tested in vivo. The results are provided in FIG. 32, and correlated with the ex vivo results. Red fluorescent particles were injected to the SCS, then iontophoresis was applied for 3 minutes. Subsequently, the hydrogel formulation was injected at the same injection site. Two weeks after the injection, the particle distribution was analyzed. ~ 15% of particles were in the anterior SCS and ~65% of particles were in the posterior SCS. Thus, the charged particles injected into the SCS were delivered more preferentially to the posterior of the SCS by iontophoresis. HA hydrogel pushing delivered the particles further to the posterior. 2 weeks after the injection, even more particles were delivered to the back compared to the results at 1 week, indicating that hydrogel swelling was still working even an additional week after injection.

Together, the results of the study showed that iontophoresis and hydrogel pushing in the suprachoroidal space can target delivery of particles to the back of the eye, which may be of use for drug delivery of posterior ocular diseases.

Figure 33:
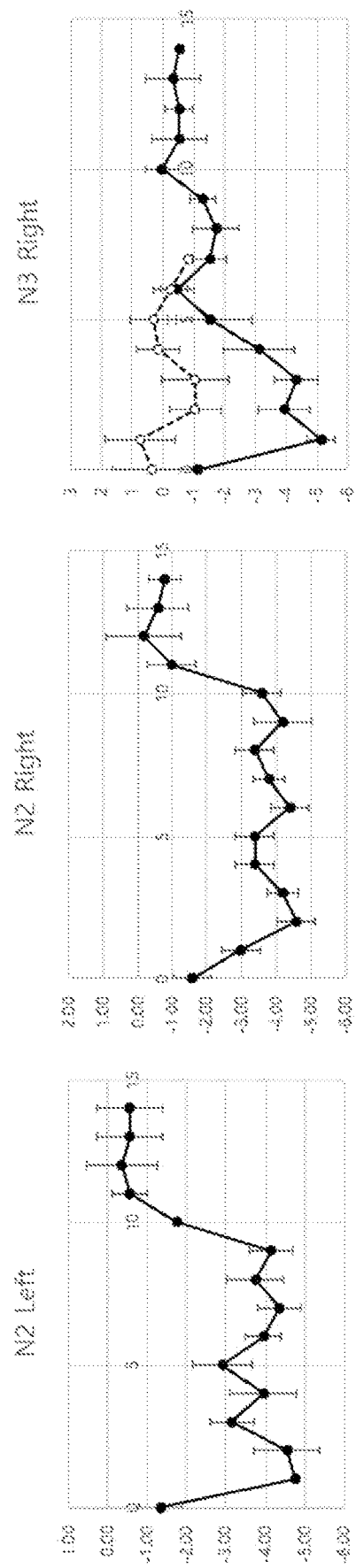
FIG. 33 shows the intraocular pressure (IOP) after the combination iontophoresis+hydrogel injection in three animals (N1, N2, and N3). IOP was reduced to around −4 mmHg after treatment. In N3, the TOP of the injected eye was reduced after the injection, but the IOP in the other eye (dashed line) was normal. In each animal, IOP recovered to the normal range around 9~10 days after the injection.
Figure 34:
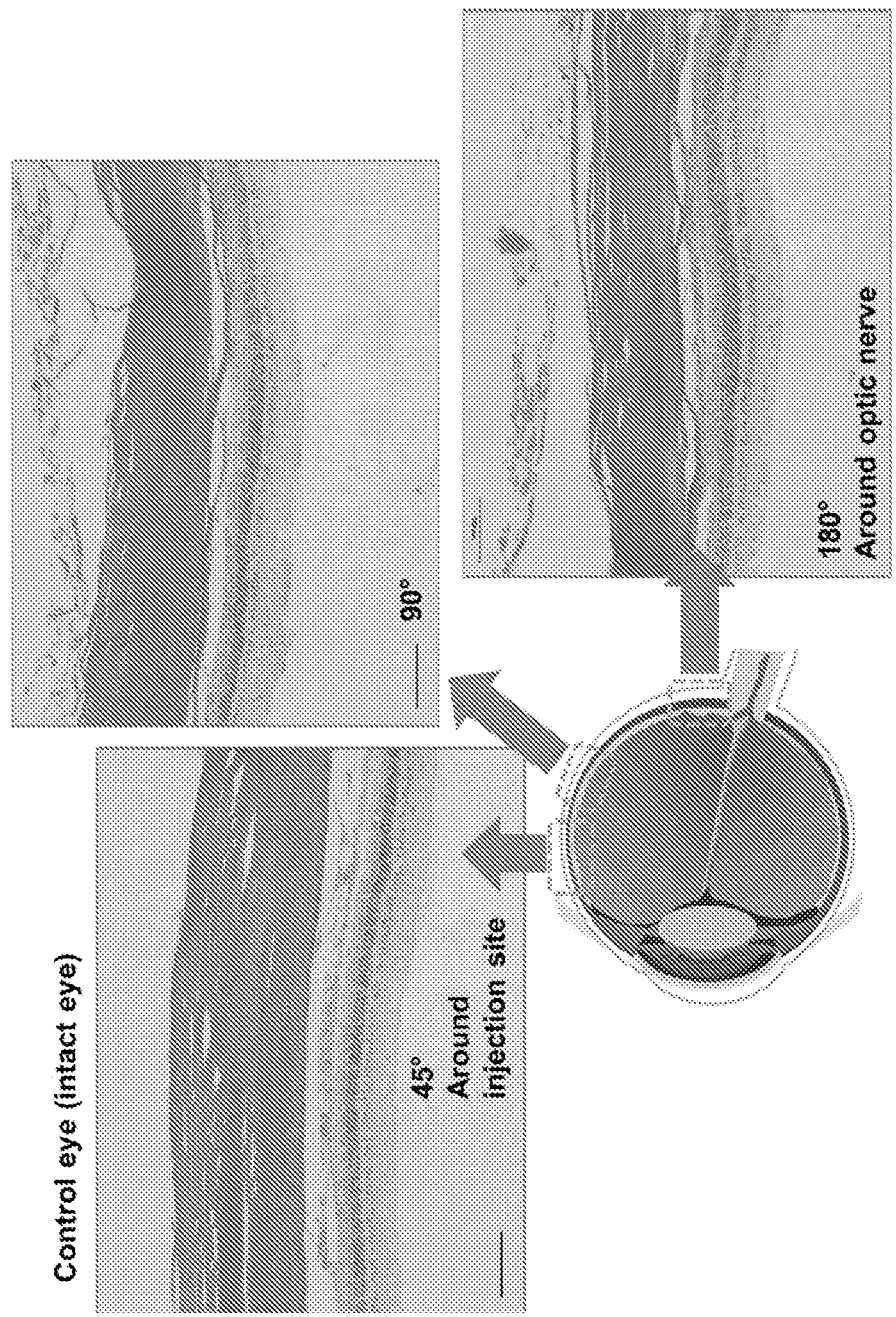
FIG. 34 provides histology of a control (untreated) eye.
Figure 35:
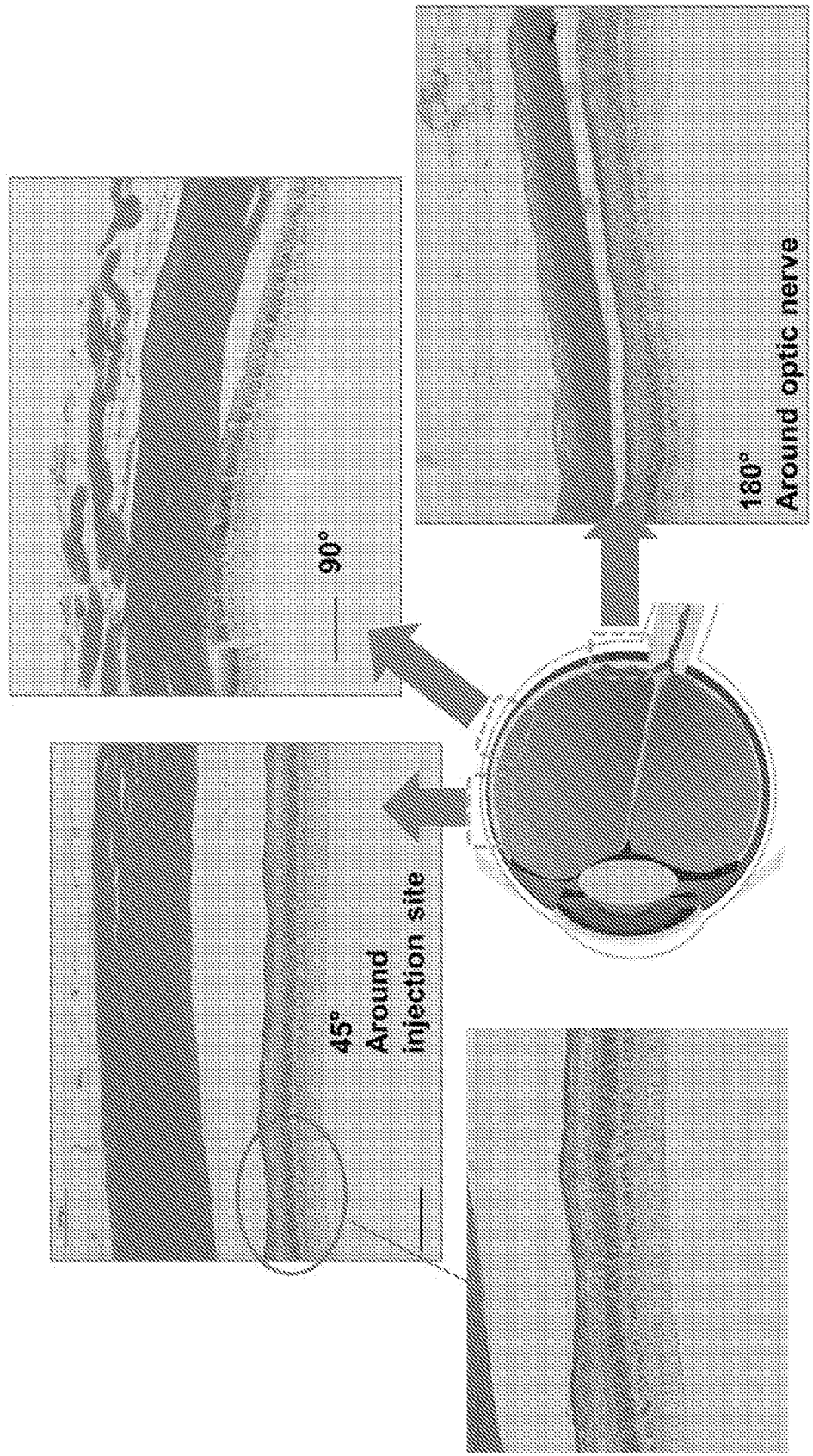
FIG. 35 provides histology of a treated eye (iontophoresis+hydrogel injection) 2 days after the injection. Although there was a slight inflammatory response, generally the retina and choroid, and other areas did not show significant damage.
Figure 36:
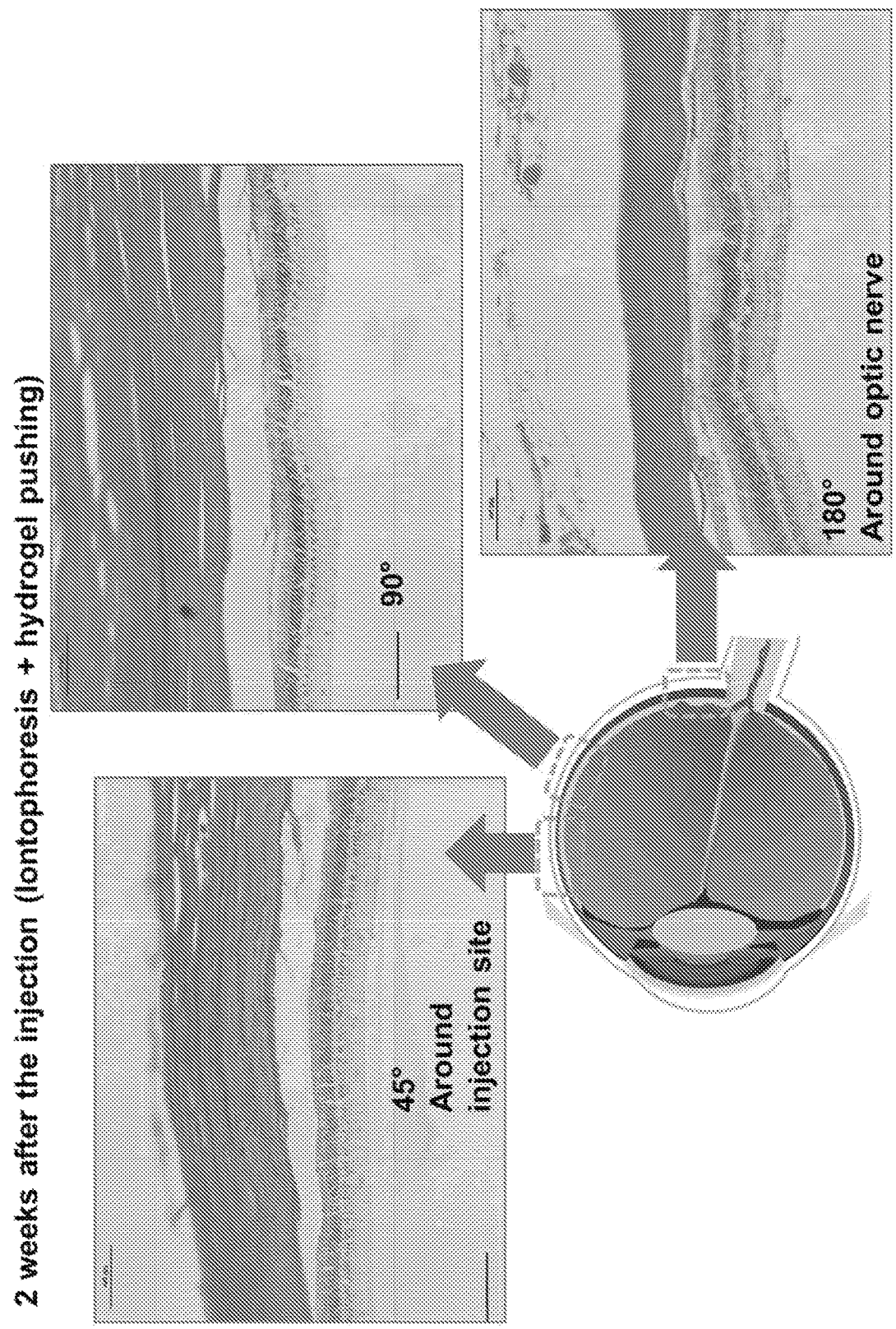
FIG. 36 provides histology of a treated eye (iontophoresis+hydrogel injection) 2 weeks after the injection. Generally the retina, choroid, and other areas did not show significant damage.

In addition, to confirm the safety of this drug delivery system, intraocular pressure (IOP) was measured after the injection for 2 weeks and the injected rabbit eyes were analyzed in vivo 2 days and 2 weeks after the injection by histology. Although the IOP was lowered about 4 mmHg right after the injection, it recovered around 9 days after the injection (FIG. 33). FIG. 34 shows the histology of a control eye. FIGS. 35 and 36 show the histology of the eyes 2 days or 2 weeks, respectively, after iontophoresis and hydrogel pushing. Although there was a slight inflammatory response 2 days after the injection, there was not significant damage to the retina, choroid, or other areas at 2 days or at 2 weeks after injection. Accordingly, the combination treatment of iontophoresis with hydrogel pushing in SCS drug delivery was safe as well as effective.

Publications, patents and patent applications cited herein are specifically incorporated by reference in their entireties. While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

The invention claimed is:

1. A method for delivery of a drug formulation to a target tissue in the eye of a subject, the method comprising administering to the suprachoroidal space (SCS) of the subject a first formulation and a second formulation, wherein the first formulation comprises an active agent useful in the treatment of a disease or disorder and the second formulation is a pushing formulation.

2. The method of claim 1, wherein the first formulation and the second formulation are administered to the SCS using a microneedle.

3. The method of claim 1, wherein the first formulation and the second formulation are administered to the SCS using a device containing both the first and second formulation.

4. The method of claim 1, wherein the first formulation is administered to the SCS prior to administration to the SCS of the second formulation.

5. The method of claim 1, wherein the first formulation has a lower viscosity than the second formulation.

6. The method of claim 1, wherein the second formulation further comprises high-salt.

7. The method of claim 1, wherein the second formulation further comprises 9% sodium chloride.

8. The method of claim 1, wherein the first formulation comprises particles.

9. The method of claim 1, wherein the first formulation further comprises about 1% (w/v) HA and the second formulation comprises about 4% (w/v) HA.

10. The method of claim 1, wherein the target tissue of the eye is selected from the group consisting of the posterior pole, optic nerve, choroid, retina, vitreous humor, macula, iris, and ciliary body.

11. The method of claim 2, wherein the microneedle is a hollow microneedle, wherein the hollow microneedle is between about 600 µm and about 1200 µm in length.

12. The method of claim 1, wherein the method results in localization of at least 30% of the first formulation to a location in the eye that is at least about 6 mm posterior to the limbus.

13. The method of claim 1, wherein the second formulation swells over time for at least 1 hour after injection.

14. The method of claim 12, wherein 61.2±7.7% of the first formulation remains over 6 mm posterior to the limbus for 2 days after administration.

15. A method for treating an ocular disease or disorder in a subject in need thereof, the method comprising administering to the suprachoroidal space (SCS) of the subject a first formulation and a second formulation, wherein the first formulation comprises an active agent useful in the treatment of an ocular disease or disorder and the second formulation is a pushing formulation.

16. A method for delivery of a drug formulation to a target tissue in the eye of a subject, the method comprising
  (i) administering to the suprachoroidal space (SCS) of the eye of the subject a first formulation and a second formulation, wherein the first formulation comprises an active agent useful in the treatment of an ocular disease or disorder and the second formulation is a pushing formulation; and
  (ii) applying iontophoresis to the eye of the subject to localize the active agent to a target tissue in the eye.

\* \* \* \* \*

UNITED STATES PATENT AND TRADEMARK OFFICE
CERTIFICATE OF CORRECTION

| | | |
|---|---|---|
| PATENT NO. | : 12,090,294 B2 | Page 1 of 1 |
| APPLICATION NO. | : 16/609583 | |
| DATED | : September 17, 2024 | |
| INVENTOR(S) | : Jung et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 944 days.

Signed and Sealed this
Thirtieth Day of September, 2025

John A. Squires
*Director of the United States Patent and Trademark Office*